United States Patent
Pal et al.

(10) Patent No.: US 12,337,196 B2
(45) Date of Patent: Jun. 24, 2025

(54) SYSTEMS AND METHODS FOR SHUTTLE MODE RADIATION DELIVERY

(71) Applicant: RefleXion Medical, Inc., Hayward, CA (US)

(72) Inventors: Debashish Pal, Sunnyvale, CA (US); Ayan Mitra, Dublin, CA (US); Christopher Eric Brown, Morgan Hill, CA (US); Peter Demetri Olcott, Los Gatos, CA (US); Yevgen Voronenko, San Jose, CA (US); Rostem Bassalow, Lacey, WA (US)

(73) Assignee: RefleXion Medical, Inc., Hayward, CA (US)

( * ) Notice: Subject to any disclaimer, the term of this patent is extended or adjusted under 35 U.S.C. 154(b) by 12 days.

(21) Appl. No.: 18/480,900

(22) Filed: Oct. 4, 2023

(65) Prior Publication Data

US 2024/0173568 A1     May 30, 2024

Related U.S. Application Data

(63) Continuation of application No. 17/877,719, filed on Jul. 29, 2022, now Pat. No. 11,813,481, which is a
(Continued)

(51) Int. Cl.
     *A61N 5/10*               (2006.01)

(52) U.S. Cl.
     CPC ......... *A61N 5/1031* (2013.01); *A61N 5/1001* (2013.01); *A61N 5/1045* (2013.01);
(Continued)

(58) Field of Classification Search
     CPC .. A61N 5/1031; A61N 5/1001; A61N 5/1045; A61N 5/1049; A61N 5/1065;
(Continued)

(56) References Cited

U.S. PATENT DOCUMENTS

| | | |
|---|---|---|
| 3,794,840 A | 2/1974 | Scott |
| 5,394,452 A | 2/1995 | Swerdloff et al. |

(Continued)

FOREIGN PATENT DOCUMENTS

| | | |
|---|---|---|
| CN | 1681436 A | 10/2005 |
| CN | 1824342 A | 8/2006 |

(Continued)

OTHER PUBLICATIONS

Extended European Search Report mailed on Jan. 24, 2024, for EP Application No. 23 160 060.2, filed on Mar. 9, 2009, 12 pages.
(Continued)

*Primary Examiner* — Kiho Kim
(74) *Attorney, Agent, or Firm* — Cooley LLP

(57) ABSTRACT

Systems and methods for shuttle mode radiation delivery are described herein. One method for radiation delivery comprises moving the patient platform through the patient treatment region multiple times during a treatment session. This may be referred to as patient platform or couch shuttling (i.e., couch shuttle mode). Another method for radiation delivery comprises moving the therapeutic radiation source jaw across a range of positions during a treatment session. The jaw may move across the same range of positions multiple times during a treatment session. This may be referred to as jaw shuttling (i.e., jaw shuttle mode). Some methods combine couch shuttle mode and jaw shuttle mode. Methods of dynamic or pipelined normalization are also described.

20 Claims, 29 Drawing Sheets

Related U.S. Application Data continuation of application No. 17/150,977, filed on Jan. 15, 2021, now Pat. No. 11,439,844, which is a continuation of application No. 16/814,867, filed on Mar. 10, 2020, now Pat. No. 10,912,950, which is a continuation of application No. 16/138,631, filed on Sep. 21, 2018, now Pat. No. 10,617,888.

(60) Provisional application No. 62/562,212, filed on Sep. 22, 2017.

(52) U.S. Cl.
CPC ......... *A61N 5/1049* (2013.01); *A61N 5/1065* (2013.01); *A61N 5/1067* (2013.01); *A61N 5/1069* (2013.01); *A61N 5/107* (2013.01); *A61N 5/1081* (2013.01); *A61N 2005/1019* (2013.01); *A61N 5/1036* (2013.01); *A61N 5/1039* (2013.01); *A61N 2005/1041* (2013.01); *A61N 5/1075* (2013.01)

(58) Field of Classification Search
CPC .... A61N 5/1067; A61N 5/1069; A61N 5/107; A61N 5/1081; A61N 5/1036; A61N 5/1039; A61N 5/1075; A61N 2005/1019; A61N 2005/1041
See application file for complete search history.

(56) References Cited

U.S. PATENT DOCUMENTS

| | | |
|---|---|---|
| 5,511,549 A | 4/1996 | Legg et al. |
| 5,813,985 A | 9/1998 | Carroll |
| 6,023,494 A | 2/2000 | Senzig et al. |
| 6,038,283 A | 3/2000 | Carol et al. |
| 6,393,096 B1 | 5/2002 | Carol et al. |
| 6,438,202 B1 | 8/2002 | Olivera et al. |
| 6,455,856 B1 | 9/2002 | Gagnon |
| 6,459,762 B1 | 10/2002 | Wong et al. |
| 6,459,769 B1 | 10/2002 | Cosman |
| 6,504,899 B2 | 1/2003 | Pugachev et al. |
| 6,661,870 B2 | 12/2003 | Kapatoes et al. |
| 6,700,949 B2 | 3/2004 | Susami et al. |
| 6,735,277 B2 | 5/2004 | McNutt et al. |
| 7,015,490 B2 | 3/2006 | Wang et al. |
| 7,020,233 B1 | 3/2006 | Tybinkowski et al. |
| 7,085,347 B2 | 8/2006 | Mihara et al. |
| 7,177,386 B2 | 2/2007 | Mostafavi et al. |
| 7,191,100 B2 | 3/2007 | Mostafavi |
| 7,265,356 B2 | 9/2007 | Pelizzari et al. |
| 7,266,175 B1 | 9/2007 | Romesberg |
| 7,302,033 B2 | 11/2007 | Carrano et al. |
| 7,302,038 B2 | 11/2007 | Mackie et al. |
| 7,343,030 B2 | 3/2008 | Sawyer |
| 7,356,112 B2 | 4/2008 | Brown et al. |
| 7,367,955 B2 | 5/2008 | Zhang et al. |
| 7,453,984 B2 | 11/2008 | Chen et al. |
| 7,469,035 B2 | 12/2008 | Keall et al. |
| 7,496,181 B2 | 2/2009 | Mazin et al. |
| 7,508,967 B2 | 3/2009 | Harari et al. |
| 7,513,861 B2 | 4/2009 | Klein et al. |
| 7,522,779 B2 | 4/2009 | Fu et al. |
| 7,611,452 B2 | 11/2009 | Allison et al. |
| 7,620,444 B2 | 11/2009 | Le et al. |
| 7,623,623 B2 | 11/2009 | Raane et al. |
| 7,639,853 B2 | 12/2009 | Olivera et al. |
| 7,649,981 B2 | 1/2010 | Seppi et al. |
| 7,657,304 B2 | 2/2010 | Mansfield et al. |
| 7,693,257 B2 | 4/2010 | Allison |
| 7,711,087 B2 | 5/2010 | Mostafavi |
| 7,715,606 B2 | 5/2010 | Jeung et al. |
| 7,769,430 B2 | 8/2010 | Mostafavi |
| 7,783,335 B2 | 8/2010 | Le Corre |
| 7,820,989 B2 | 10/2010 | Sommer |
| 7,831,073 B2 | 11/2010 | Fu et al. |
| 7,869,862 B2 | 1/2011 | Seppi et al. |
| 7,906,770 B2 | 3/2011 | Otto |
| 7,945,021 B2 | 5/2011 | Shapiro et al. |
| 7,949,095 B2 | 5/2011 | Ning et al. |
| 7,983,380 B2 | 7/2011 | Guertin et al. |
| 8,017,915 B2 | 9/2011 | Mazin |
| 8,019,042 B2 | 9/2011 | Shukla et al. |
| 8,060,177 B2 | 11/2011 | Hamill |
| 8,063,376 B2 | 11/2011 | Maniawski et al. |
| 8,086,004 B2 | 12/2011 | Kuduvalli et al. |
| 8,090,074 B2 | 1/2012 | Filiberti et al. |
| 8,148,703 B2 | 4/2012 | Sommer |
| 8,149,991 B2 | 4/2012 | Moreau |
| 8,193,508 B2 | 6/2012 | Shchory et al. |
| 8,260,013 B2 | 9/2012 | Pekar et al. |
| 8,295,430 B2 | 10/2012 | Zhu et al. |
| 8,295,435 B2 | 10/2012 | Wang et al. |
| 8,295,906 B2 | 10/2012 | Saunders et al. |
| 8,303,505 B2 | 11/2012 | Webler et al. |
| 8,311,185 B2 | 11/2012 | Seppi et al. |
| 8,331,532 B2 | 12/2012 | Nord et al. |
| 8,442,287 B2 | 5/2013 | Fordyce, II et al. |
| 8,457,372 B2 | 6/2013 | Fu et al. |
| 8,461,538 B2 | 6/2013 | Mazin |
| 8,509,383 B2 | 8/2013 | Lu et al. |
| 8,536,547 B2 | 9/2013 | Maurer, Jr. et al. |
| 8,559,596 B2 | 10/2013 | Thomson et al. |
| 8,571,639 B2 | 10/2013 | Mostafavi |
| 8,588,367 B2 | 11/2013 | Busch et al. |
| 8,594,769 B2 | 11/2013 | Mostafavi |
| 8,699,664 B2 | 4/2014 | Otto et al. |
| 8,716,669 B2 | 5/2014 | Myaoka et al. |
| 8,748,825 B2 | 6/2014 | Mazin |
| 8,767,917 B2 | 7/2014 | Ruchala et al. |
| 8,788,020 B2 | 7/2014 | Mostafavi et al. |
| 8,824,630 B2 | 9/2014 | Maurer, Jr. et al. |
| 8,831,706 B2 | 9/2014 | Fu et al. |
| 8,841,628 B2 | 9/2014 | Kitano et al. |
| 8,861,672 B2 | 10/2014 | Maltz et al. |
| 8,874,187 B2 | 10/2014 | Thomson et al. |
| 8,917,813 B2 | 12/2014 | Maurer, Jr. |
| 9,155,909 B2 | 10/2015 | Ishikawa |
| 9,205,281 B2 | 12/2015 | Mazin |
| 9,232,928 B2 | 1/2016 | Mostafavi |
| 9,248,312 B2 | 2/2016 | Li et al. |
| 9,456,764 B2 | 10/2016 | Burke et al. |
| 9,616,251 B2 | 4/2017 | Filiberti et al. |
| 9,731,148 B2 | 8/2017 | Olivera et al. |
| 9,820,700 B2 | 11/2017 | Mazin |
| 9,849,308 B2 | 12/2017 | Berlinger et al. |
| 9,990,711 B2 | 6/2018 | Lugosi et al. |
| 10,065,049 B2 | 9/2018 | Lugosi et al. |
| 10,279,196 B2 | 5/2019 | West et al. |
| 10,327,716 B2 | 6/2019 | Mazin |
| 10,406,382 B2 | 9/2019 | Humber et al. |
| 10,449,389 B2 | 10/2019 | Ollila et al. |
| 10,617,888 B2 | 4/2020 | Pal et al. |
| 10,646,188 B2 | 5/2020 | Mostafavi et al. |
| 10,688,320 B2 | 6/2020 | Voronenko et al. |
| 10,695,586 B2 | 6/2020 | Harper et al. |
| 10,737,118 B2 | 8/2020 | Mostafavi |
| 10,799,716 B2 | 10/2020 | Morgas et al. |
| 10,806,368 B2 | 10/2020 | Hebert |
| 10,835,761 B2 | 11/2020 | Beriault et al. |
| 10,912,950 B2 | 2/2021 | Pal et al. |
| 10,918,885 B2 | 2/2021 | Haas et al. |
| 10,959,686 B2 | 3/2021 | Mazin |
| 11,033,757 B2 | 6/2021 | Voronenko et al. |
| 11,083,913 B2 | 8/2021 | Lachaine et al. |
| 11,154,269 B2 | 10/2021 | Shea et al. |
| 11,173,324 B2 | 11/2021 | Paysan et al. |
| 11,278,737 B2 | 3/2022 | Peltola et al. |
| 11,291,858 B2 | 4/2022 | MacDonald et al. |
| 11,309,072 B2 | 4/2022 | Carmi |
| 11,358,008 B2 | 6/2022 | Voronenko et al. |
| 11,369,805 B2 | 6/2022 | Maltz |
| 11,369,806 B2 | 6/2022 | Laurence, Jr. et al. |
| 11,439,844 B2 | 9/2022 | Pal et al. |

(56) References Cited

U.S. PATENT DOCUMENTS

| | | | |
|---|---|---|---|
| 11,478,662 B2 | 10/2022 | Sayeh et al. |
| 11,504,548 B2 | 11/2022 | Fong de los Santos et al. |
| 11,504,550 B2 | 11/2022 | Maolinbay |
| 11,520,415 B2 | 12/2022 | Douglas et al. |
| 11,596,807 B2 | 3/2023 | Maurer et al. |
| 11,617,903 B2 | 4/2023 | Lamb et al. |
| 11,627,920 B2 | 4/2023 | Mazin |
| 11,633,626 B2 | 4/2023 | Voronenko et al. |
| 11,642,027 B2 | 5/2023 | Otto |
| 11,684,801 B2 | 6/2023 | Schadewaldt et al. |
| 11,801,398 B2 | 10/2023 | Voronenko et al. |
| 11,813,481 B2 | 11/2023 | Pal et al. |
| 11,896,848 B2 | 2/2024 | Janardhanan et al. |
| 12,115,386 B2 | 10/2024 | Voronenko et al. |
| 12,167,922 B2 | 12/2024 | Mazin |
| 12,233,286 B2 | 2/2025 | Voronenko et al. |
| 2002/0191734 A1 | 12/2002 | Kojima et al. |
| 2003/0036700 A1 | 2/2003 | Weinberg |
| 2003/0058984 A1 | 3/2003 | Susami et al. |
| 2003/0128801 A1 | 7/2003 | Eisenberg et al. |
| 2003/0219098 A1 | 11/2003 | McNutt et al. |
| 2004/0024300 A1 | 2/2004 | Graf |
| 2004/0030246 A1 | 2/2004 | Townsend et al. |
| 2004/0037390 A1 | 2/2004 | Mihara et al. |
| 2004/0057557 A1 | 3/2004 | Nafstadius |
| 2004/0096033 A1 | 5/2004 | Seppi et al. |
| 2004/0116804 A1 | 6/2004 | Mostafavi |
| 2004/0120452 A1 | 6/2004 | Shapiro et al. |
| 2004/0184579 A1 | 9/2004 | Mihara et al. |
| 2004/0218719 A1 | 11/2004 | Brown et al. |
| 2004/0264640 A1 | 12/2004 | Myles |
| 2005/0089135 A1 | 4/2005 | Toth et al. |
| 2005/0109939 A1 | 5/2005 | Engler et al. |
| 2005/0111621 A1 | 5/2005 | Riker et al. |
| 2005/0111757 A1 | 5/2005 | Brackett et al. |
| 2005/0113961 A1 | 5/2005 | Sabol et al. |
| 2005/0197564 A1 | 9/2005 | Dempsey |
| 2005/0201509 A1 | 9/2005 | Mostafavi et al. |
| 2005/0201510 A1 | 9/2005 | Mostafavi |
| 2005/0207531 A1 | 9/2005 | Dempsey et al. |
| 2006/0002511 A1 | 1/2006 | Miller et al. |
| 2006/0058637 A1 | 3/2006 | Sommer |
| 2006/0113482 A1 | 6/2006 | Pelizzari et al. |
| 2006/0159220 A1 | 7/2006 | Heuscher |
| 2006/0182326 A1 | 8/2006 | Schildkraut et al. |
| 2006/0193435 A1 | 8/2006 | Hara et al. |
| 2006/0237652 A1 | 10/2006 | Kimchy et al. |
| 2006/0241332 A1 | 10/2006 | Klein et al. |
| 2006/0293583 A1 | 12/2006 | Saracen et al. |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0025496 A1 | 2/2007 | Brown et al. |
| 2007/0025524 A1 | 2/2007 | Yue |
| 2007/0075273 A1 | 4/2007 | Birgy et al. |
| 2007/0133749 A1 | 6/2007 | Mazin et al. |
| 2007/0153969 A1 | 7/2007 | Maschke |
| 2007/0165779 A1 | 7/2007 | Chen et al. |
| 2007/0167801 A1 | 7/2007 | Webler et al. |
| 2007/0237290 A1 | 10/2007 | Mostafavi |
| 2007/0242801 A1 | 10/2007 | Mackie et al. |
| 2007/0265528 A1 | 11/2007 | Xu et al. |
| 2008/0002811 A1 | 1/2008 | Allison |
| 2008/0031406 A1 | 2/2008 | Yan et al. |
| 2008/0071131 A1 | 3/2008 | Rietzel |
| 2008/0095416 A1 | 4/2008 | Jeung et al. |
| 2008/0128631 A1 | 6/2008 | Suhami |
| 2008/0156993 A1 | 7/2008 | Weinberg et al. |
| 2008/0205588 A1 | 8/2008 | Kim |
| 2008/0230705 A1 | 9/2008 | Rousso et al. |
| 2008/0273659 A1 | 11/2008 | Guertin et al. |
| 2009/0088622 A1 | 4/2009 | Mostafavi |
| 2009/0116616 A1 | 5/2009 | Lu et al. |
| 2009/0169082 A1 | 7/2009 | Mizuta et al. |
| 2009/0296886 A1 | 12/2009 | Maltz et al. |
| 2010/0049030 A1 | 2/2010 | Saunders et al. |
| 2010/0054411 A1 | 3/2010 | Nord et al. |
| 2010/0150309 A1 | 6/2010 | Nord et al. |
| 2010/0266099 A1 | 10/2010 | Busch et al. |
| 2011/0073763 A1 | 3/2011 | Subbarao |
| 2011/0122997 A1 | 5/2011 | Lu et al. |
| 2011/0150186 A1* | 6/2011 | Ziegler ............... A61N 5/1081 378/196 |
| 2011/0291015 A1 | 12/2011 | Mazin |
| 2011/0301449 A1 | 12/2011 | Maurer, Jr. |
| 2012/0020449 A1 | 1/2012 | Yan et al. |
| 2012/0043481 A1 | 2/2012 | Mansfield et al. |
| 2012/0053961 A1 | 3/2012 | Wang et al. |
| 2012/0189102 A1 | 7/2012 | Maurer, Jr. et al. |
| 2012/0230464 A1 | 9/2012 | Ling et al. |
| 2013/0083004 A1 | 4/2013 | Nord et al. |
| 2013/0158382 A1 | 6/2013 | Chao |
| 2013/0188856 A1 | 7/2013 | Adler, Jr. et al. |
| 2013/0279658 A1 | 10/2013 | Mazin |
| 2013/0336449 A1 | 12/2013 | Tanabe |
| 2014/0105355 A1 | 4/2014 | Toimela et al. |
| 2014/0321615 A1 | 10/2014 | Carlsson |
| 2014/0348297 A1 | 11/2014 | Burshtein et al. |
| 2014/0371581 A1 | 12/2014 | Mostafavi et al. |
| 2015/0043709 A1 | 2/2015 | Shapiro et al. |
| 2016/0023019 A1 | 1/2016 | Filiberti et al. |
| 2016/0038767 A1 | 2/2016 | Wiersma et al. |
| 2016/0140300 A1* | 5/2016 | Purdie ............... G16H 20/40 705/2 |
| 2016/0331997 A1 | 11/2016 | Vilsmeier |
| 2016/0361566 A1 | 12/2016 | Larkin et al. |
| 2017/0028221 A1 | 2/2017 | Kontaxis et al. |
| 2017/0084025 A1 | 3/2017 | Lyu |
| 2017/0087385 A1 | 3/2017 | Miettinen et al. |
| 2017/0209715 A1 | 7/2017 | Ruebel et al. |
| 2017/0252579 A1 | 9/2017 | Kilby |
| 2018/0133508 A1 | 5/2018 | Pearce et al. |
| 2018/0133518 A1 | 5/2018 | Harper et al. |
| 2018/0154179 A1 | 6/2018 | Ollila et al. |
| 2019/0001152 A1 | 1/2019 | O'Connor et al. |
| 2019/0054315 A1 | 2/2019 | Isola et al. |
| 2019/0070436 A1 | 3/2019 | Willcut et al. |
| 2019/0255362 A1 | 8/2019 | Voronenko et al. |
| 2019/0381338 A1 | 12/2019 | Voronenko et al. |
| 2021/0128947 A1 | 5/2021 | Pal et al. |
| 2021/0196212 A1 | 7/2021 | Mazin |
| 2021/0236854 A1 | 8/2021 | Voronenko et al. |
| 2021/0327560 A1 | 10/2021 | Carmi |
| 2022/0126117 A1 | 4/2022 | Voronenko et al. |
| 2023/0087425 A1 | 3/2023 | Pal et al. |
| 2023/0337991 A1 | 10/2023 | Mazin |
| 2024/0316363 A1 | 9/2024 | Voronenko et al. |
| 2025/0032818 A1 | 1/2025 | Voronenko et al. |

FOREIGN PATENT DOCUMENTS

| | | |
|---|---|---|
| CN | 1960780 A | 5/2007 |
| CN | 101267767 A | 9/2008 |
| CN | 103180014 A | 6/2013 |
| CN | 104284697 A | 1/2015 |
| CN | 105658279 A | 6/2016 |
| CN | 106563211 A | 4/2017 |
| CN | 107072595 A | 8/2017 |
| CN | 107072628 A | 8/2017 |
| EP | 0 212 135 B1 | 9/1991 |
| EP | 1 454 653 B1 | 9/2007 |
| EP | 3 175 886 B1 | 6/2018 |
| JP | 2905995 B2 | 6/1999 |
| JP | H-11-290466 A | 10/1999 |
| JP | 2005-261941 A | 9/2005 |
| JP | 2007-502166 A | 2/2007 |
| JP | 2007-507246 A | 3/2007 |
| JP | 2009-502249 A | 1/2009 |
| JP | 2011-528977 A | 12/2011 |
| JP | 2016-174674 A | 10/2016 |
| JP | 2017-199876 A | 11/2017 |
| WO | WO-94/28971 A2 | 12/1994 |
| WO | WO-94/28971 A3 | 12/1994 |
| WO | WO-03/018132 A1 | 3/2003 |

(56) References Cited

FOREIGN PATENT DOCUMENTS

| | | |
|---|---|---|
| WO | WO-03/076003 A2 | 9/2003 |
| WO | WO-03/076003 A3 | 9/2003 |
| WO | WO-2004/017832 A2 | 3/2004 |
| WO | WO-2004/017832 A3 | 3/2004 |
| WO | WO-2004/105574 A2 | 12/2004 |
| WO | WO-2004/105574 A3 | 12/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/031629 A1 | 4/2005 |
| WO | WO-2005/110495 A1 | 11/2005 |
| WO | WO-2006/051531 A2 | 5/2006 |
| WO | WO-2006/051531 A3 | 5/2006 |
| WO | WO-2006/086765 A2 | 8/2006 |
| WO | WO-2006/086765 A3 | 8/2006 |
| WO | WO-2007/082126 A2 | 7/2007 |
| WO | WO-2007/082126 A3 | 7/2007 |
| WO | WO-2007/120674 A2 | 10/2007 |
| WO | WO-2007/120674 A3 | 10/2007 |
| WO | WO-2008/011725 A1 | 1/2008 |
| WO | WO-2008/024463 A2 | 2/2008 |
| WO | WO-2008/024463 A3 | 2/2008 |
| WO | WO-2008/127368 A2 | 10/2008 |
| WO | WO-2008/127368 A3 | 10/2008 |
| WO | WO-2009/114117 A2 | 9/2009 |
| WO | WO-2009/114117 A3 | 9/2009 |
| WO | WO-2016/023786 A1 | 2/2016 |
| WO | WO-2016/064750 A1 | 4/2016 |
| WO | WO-2017/048852 A1 | 3/2017 |
| WO | WO-2017/156316 A1 | 9/2017 |
| WO | WO-2018/093933 A1 | 5/2018 |
| WO | WO-2018/183748 A1 | 10/2018 |
| WO | WO-2018/222751 A1 | 12/2018 |
| WO | WO-2019/060764 A1 | 3/2019 |
| WO | WO-2019/160958 A1 | 8/2019 |

OTHER PUBLICATIONS

Non-Final Office Action mailed on Jan. 16, 2024, for U.S. Appl. No. 18/178,431, filed Mar. 3, 2023, 16 pages.
Notice of Allowance mailed on Dec. 13, 2023, for U.S. Appl. No. 17/375,586, filed Jul. 14, 2021, 12 pages.
Black, Q.C. et al. (2004). "Defining a Radiotherapy Target with positron emission tomography," Int. J. Radiation Oncology Biol. Phys. 60:1272-1282.
Bortfield, T. et al. (2002). "Effects of intra-fraction motion on IMRT dose delivery: Statistical analysis and simulation," Phys. Med. Biol. 47:2203-2220.
Chen, Y. et al. (2011). "Dynamic tomotherapy delivery," Am. Assoc. Phys. Med. 38:3013-3024.
Corrected Notice of Allowability mailed on Mar. 10, 2020, for U.S. Appl. No. 16/138,631, filed Sep. 21, 2018, 4 pages.
Corrected Notice of Allowability mailed on Mar. 13, 2023, for U.S. Appl. No. 17/235,812, filed Apr. 20, 2021, 4 pages.
Corrected Notice of Allowability mailed on Mar. 16, 2023, for U.S. Appl. No. 17/203,532, filed Mar. 16, 2021, 2 pages.
Dieterich, S. et al. (2003). "Skin respiratory motion tracking for stereotactic radiosurgery using the CyberKnife," Elsevier Int'l Congress Series 1256:130-136.
Erdi, Y.E. (2007). "The use of PET for radiotherapy," Curr. Medical Imaging Reviews 3(1):3-16.
Extended European Search Report mailed on Mar. 31, 2017, for European Application No. 09 719 473.2, filed on Mar. 9, 2009, 8 pages.
Extended European Search Report mailed on Oct. 30, 2020, for EP Application No. 20 179 036.7, filed on Mar. 9, 2009, 12 pages.
Extended European Search Report mailed on May 19, 2021, for European Application No. 18 857 863.7, filed on Sep. 21, 2018, 7 pages.
Extended European Search Report mailed on Feb. 3, 2021, for European Application No. 18810297.4, filed on May 30, 2018, 4 pages.
Extended European Search Report mailed on Oct. 15, 2021, for European Application No. 19 754 923.1, filed on Feb. 13, 2019, 11 pages.
Extended European Search Report mailed on Jun. 23, 2023, for EP Application No. 20 840 804.7, filed on Jul. 2, 2020, 7 pages.
Final Office Action mailed on Aug. 15, 2012, for U.S. Appl. No. 13/209,275, filed Aug. 12, 2011, 8 pages.
Hunt, M.A. et al. (2003). "Treatment Planning Considerations using IMRT," pp. 103-121.
International Search Report mailed on May 4, 2009, for PCT Application No. PCT/US2009/01500, filed on Mar. 9, 2009, 3 pages.
International Search Report mailed on Oct. 3, 2018, for PCT Application No. PCT/US2018/035188, filed on May 30, 2018, 4 pages.
International Search Report mailed on Apr. 23, 2020, for PCT Application No. PCT/US2020/013927, filed on Jan. 16, 2020, 3 pages.
International Search Report mailed on Jan. 18, 2019, for PCT Application No. PCT/US2018/052272, filed on Sep. 21, 2018, 4 pages.
International Search Report mailed on Jun. 14, 2019, for PCT Application No. PCT/US2019/017855, filed on Feb. 13, 2019, 4 pages.
Kapatoes, J. M. (2001). "On the accuracy and effectiveness of dose reconstruction for tomotherapy," Physics in Med. Biol. 46:943-966.
Kim, B. et al. (2009). "Motion-induced dose artifacts in helical tomotherapy," Phys. Med. Biol. 54:5707-5734.
Kissick, M.W. et al. (2008). "On the impact of longitudinal breathing motion randomness for tomotherapy delivery," Phys. Med. Biol. 53:4855-4873.
Lu, W. (2008). "Real time motion-adaptive delivery (MAD) using binary MLC: II. Rotation beam (tomotherapy) delivery," Phys. Med. Biol. 53:6513-6531.
Manikandan et al. (2013). "Role of step size and max dwell time in anatomy based inverse optimization for prostate implants," J. Med. Phys. 38:148-154.
Moratal, D. et al. (2008). "$k$-Space tutorial: An MRI educational tool for a better understanding of $k$-space," Biomed. Imaging Interv. J. 4:e15, 8 total pages.
Netherton, T. et al. (2017). "The Interplay effect when treating moving tumors using high-dose rate and increased MLC and Gantry Rotation speeds," AAPM 59th Annual Meeting & Exhibition, 1 total page.
Non-Final Office Action mailed on Jan. 10, 2011, for U.S. Appl. No. 12/367,679, filed Feb. 9, 2009, 9 pages.
Non-Final Office Action mailed on Feb. 28, 2012, for U.S. Appl. No. 13/209,275, filed Aug. 12, 2011, 8 pages.
Non-Final Office Action mailed on Sep. 19, 2013, for U.S. Appl. No. 13/895,255, filed May 15, 2013, 8 pages.
Non-Final Office Action mailed on Dec. 6, 2019, for U.S. Appl. No. 15/993,325, filed May 30, 2018, 8 pages.
Non-Final Office Action mailed on Mar. 3, 2022, for U.S. Appl. No. 17/150,977, filed Jan. 15, 2021, 8 pages.
Non-Final Office Action mailed on Mar. 3, 2022, for U.S. Appl. No. 16/274,962, filed Feb. 13, 2019, 12 pages.
Non-Final Office Action mailed on Jul. 5, 2022, for U.S. Appl. No. 17/203,532, filed Mar. 16, 2021, 13 pages.
Non-Final Office Action mailed on Aug. 30, 2022, for U.S. Appl. No. 17/235,812, filed Apr. 20, 2021, 8 pages.
Non-Final Office Action mailed on May 26, 2023, for U.S. Appl. No. 17/877,719, filed Jul. 29, 2022, 7 pages.
Notice of Allowance mailed on Jul. 25, 2011, for U.S. Appl. No. 12/367,679, filed Feb. 9, 2009, 7 pages.
Notice of Allowance mailed on Apr. 9, 2014, for U.S. Appl. No. 13/895,255, filed May 15, 2013, 7 pages.
Notice of Allowance mailed on Oct. 27, 2015, for U.S. Appl. No. 14/278,973, filed May 15, 2014, 8 pages.
Notice of Allowance mailed on Mar. 27, 2013, for U.S. Appl. No. 13/209,275, filed Aug. 12, 2011, 9 pages.

(56) References Cited

OTHER PUBLICATIONS

Notice of Allowance mailed on Oct. 5, 2017, for U.S. Appl. No. 14/951,194, filed Nov. 24, 2015, 11 pages.
Notice of Allowance mailed on Apr. 4, 2019, for U.S. Appl. No. 15/807,383, filed Nov. 8, 2017, 11 pages.
Notice of Allowance mailed on Jan. 21, 2020, for U.S. Appl. No. 16/138,631, filed Sep. 21, 2018, 11 pages.
Notice of Allowance mailed on Apr. 20, 2020, for U.S. Appl. No. 15/993,325, filed May 30, 2018, 7 pages.
Notice of Allowance mailed on Nov. 19, 2020, for U.S. Appl. No. 16/814,867, filed Mar. 10, 2020, 10 pages.
Notice of Allowance mailed on Apr. 12, 2022, for U.S. Appl. No. 16/274,962, filed Feb. 13, 2019, 8 pages.
Notice of Allowance mailed on Jun. 15, 2022, for U.S. Appl. No. 17/150,977, filed Jan. 15, 2021, 8 pages.
Notice of Allowance mailed on Dec. 15, 2022, for U.S. Appl. No. 17/203,532, filed Mar. 16, 2021, 8 pages.
Notice of Allowance mailed on Feb. 1, 2023, for U.S. Appl. No. 17/235,812, filed Apr. 20, 2021, 7 pages.
Notice of Allowance mailed on Apr. 4, 2023, for U.S. Appl. No. 17/831,105, filed Jun. 2, 2022, 9 pages.
Notice of Allowance mailed on Jul. 5, 2023, for U.S. Appl. No. 17/831,105, filed Jun. 2, 2022, 7 pages.
Notice of Allowance mailed on Sep. 6, 2023, for U.S. Appl. No. 17/877,719, filed Jul. 29, 2022, 7 pages.
Salter, B.J. (2001). "NOMOS Peacock IMRT utilizing the Beak™ post collimation device," Med. Dosim. 26:37-45.
Wang, D. et al. (2006). "Initial experience of FOG-PET/CT guided IMRT of head-and-neck carcinoma," Int. J. Radiation Oncology Biol. Phys. 65:143-151.
Written Opinion of the International Searching Authority mailed on May 4, 2009, for PCT Application No. PCT/US2009/01500, filed on Mar. 9, 2009, 5 pages.
Written Opinion of the International Searching Authority mailed on Oct. 3, 2018, for PCT Application No. PCT/US2018/035188, filed on May 30, 2018, 28 pages.
Written Opinion of the International Searching Authority mailed on Jan. 18, 2019, for PCT Application No. PCT/US2018/052272, filed on Sep. 21, 2018, 14 pages.
Written Opinion of the International Searching Authority mailed on Jun. 14, 2019, for PCT Application No. PCT/US2019/017855, filed on Feb. 13, 2019, 10 pages.
Written Opinion of the International Searching Authority mailed on Apr. 23, 2020, for PCT Application No. PCT/US2020/013927, filed on Jan. 16, 2020, 4 pages.
Extended European Search Report mailed on Sep. 10, 2024, for EP Application No. 24 164 232.1, filed on Sep. 21, 2018, 8 pages.
Notice of Allowance mailed on May 9, 2024, for U.S. Appl. No. 17/571,273, filed Jan. 7, 2022, 15 pages.
Notice of Allowance mailed on Aug. 13, 2024, for U.S. Appl. No. 18/178,431, filed Mar. 3, 2023, 9 pages.
Supplemental Notice of Allowability mailed on Aug. 8, 2024, for U.S. Appl. No. 17/571,273, filed Jan. 7, 2022, 2 pages.

* cited by examiner

|  | Planned Dose | Tumor POV Dose Using 1 Pass | Tumor POV Dose Using 8 Pass |
|---|---|---|---|
| Max Dose in CTV | 52.8712 Gy | 61.2086 Gy | 55.3709 Gy |
| Min Dose in CTV | 48.7647 Gy | 37.5361 Gy | 47.0843 Gy |
| Coverage in CTV | 99.7% | 25.15% | 86.3% |

FIG. 3C

| 802 | Moving a patient from a first location to a second location such that the patient passes through a radiation treatment beam plane while acquiring imaging data |

| 804 | Applying a first quantity of radiation as the patient passes through the radiation beam plane |

| 806 | Moving the patient from the second location to the first location such that the patient passes through the radiation treatment beam plane while acquiring imaging data |

| 808 | Applying a second quantity of radiation as the patient passes through the radiation beam plane, where the second quantity of radiation is different from the first quantity of radiation |

| 810 | Repeating 802-804 and/or 806-808 as many times as desired or specified |

FIG. 8A

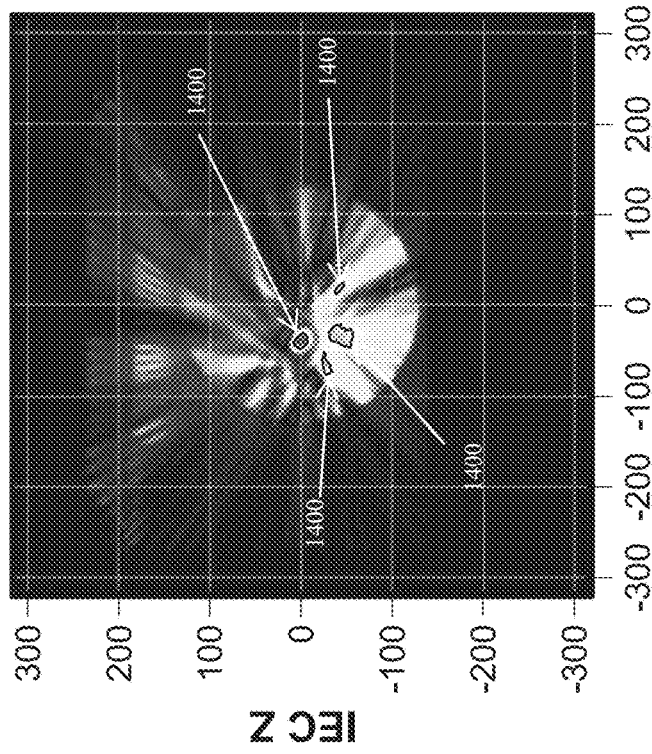
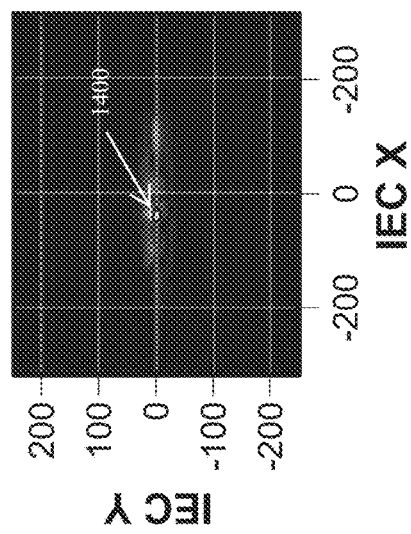
FIG. 14A
FIG. 14B
FIG. 14C

SYSTEMS AND METHODS FOR SHUTTLE MODE RADIATION DELIVERY

CROSS-REFERENCE TO RELATED APPLICATIONS

This application is a continuation of U.S. patent application Ser. No. 17/877,719, filed Jul. 29, 2022, which is a continuation of U.S. patent application Ser. No. 17/150,977, filed Jan. 15, 2021, which is a continuation of U.S. patent application Ser. No. 16/814,867, filed Mar. 10, 2020, now issued as U.S. Pat. No. 10,912,950, which is a continuation of U.S. patent application Ser. No. 16/138,631, filed Sep. 21, 2018, now issued as U.S. Pat. No. 10,617,888, which claims priority to U.S. Provisional Patent Application No. 62/562,212, filed Sep. 22, 2017, each of which is hereby incorporated by reference in its entirety.

BACKGROUND

Tumor motion modulates dose delivery in radiation therapy, often resulting in uneven dose distribution across a target region. Dose modulation may be caused by an interplay between the moving parts in a radiation therapy system (e.g., the multi-leaf collimator (MLC), the movable gantry upon which the therapeutic radiation source and the MLC are mounted, the patient platform, etc.) and the motion of the tumor. For example, because lung tumors are subject to a large range of motion that result in the tumors moving into and out of the treatment plane unpredictably, it can be challenging to deliver the prescribed radiation dose to the tumor.

Several solutions have been proposed to mitigate unwanted dose modulation. One solution for a tomotherapy machine with a rotatable gantry is called dose painting and involves arcing the therapeutic radiation source over the patient treatment region twice at a particular couch location. That is, first moving therapeutic radiation source in the clockwise and then in the anti-clockwise direction. Dose painting methods may reduce the variability in the dose delivered, but at the cost of increased treatment time. Other solutions for motion management and dose artifact reduction include coached breathing, breath hold, and respiratory gating. Instructing the patient to hold their breath during a radiation beam pulse may help limit the range of motion for the tumor, but depending on the health of the patient, it may not be possible to ensure consistent breath hold. Improved systems and methods for ensuring the uniform delivery of radiation dose to a moving target region are desirable.

SUMMARY

Disclosed herein are systems and methods for shuttle mode radiation delivery. Shuttle mode radiation delivery may be used in helical tomotherapy, with or without continuous platform motion or stepped platform motion. A radiation therapy system for helical tomotherapy may comprise a rotatable gantry that rotates about a patient treatment region, a therapeutic radiation source mounted on the rotatable gantry, and a patient platform or couch movable within the patient treatment region. In some variations, the system may further comprise beam-shaping elements disposed in the beam path of the therapeutic radiation source, including a jaw that is movable (e.g., along the direction of movement of the patient platform) and a dynamic multi-leaf collimator (MLC) that shapes the radiation emitted by the therapeutic radiation source. Some variations of a radiation therapy system may further comprise one or more PET detectors. A radiation delivery system may be configured to move the patient platform through the same segments of the patient treatment region multiple times during a treatment session. This may be referred to as patient platform or couch shuttling (i.e., couch shuttle mode). A system for radiation dose delivery may be configured to move the jaw across a range of positions while the patient platform moves through (continuously or in steps) the patient treatment region during a treatment session. The jaw may move across the same range of positions multiple times during a treatment session. This may be referred to as jaw shuttling (i.e., jaw shuttle mode), which may help provide uniform jaw dwell time over a patient target region. Some radiation delivery systems may be configured to perform both couch shuttling and jaw shuttling. The systems and methods described herein may help to mitigate dose modulation due to tumor movement and promote homogenous dose delivery to target regions. For example, the systems and methods described herein may help to mitigate dose modulation due to tumor movement and jaw/MLC interplay artifacts, and may also compensate for dose modulation due to low-frequency motion of tumors (e.g., tumor motion having a period on the order of tens of seconds, tumor shifts over multiple seconds).

One variation of a radiation delivery system may comprise a gantry, a therapeutic radiation source mounted on the gantry and configured to apply radiation in a radiation treatment beam plane, a platform movable relative to the gantry, and a controller in communication with the gantry, the radiation source, and the platform. The controller may be configured to move a patient located on the platform from a first location to a second location such that the patient passes through the radiation treatment beam plane while acquiring a first set of imaging data, and apply a first quantity of radiation with the radiation source as the patient passes through the radiation treatment beam plane, where the first quantity of radiation is derived from the first set of imaging data. The controller may be further configured to move the patient from the second location to the first location such that the patient passes through the radiation treatment beam plane while acquiring a second set of imaging data, and apply a second quantity of radiation with the radiation source as the patient passes through the radiation treatment beam plane, where the second quantity of radiation is derived from the second set of imaging data and the second quantity of radiation is different from the first quantity of radiation.

The first quantity of radiation may be determined based on the first set of imaging data, and the second quantity of radiation may be determined based on the second set of imaging data. The first and/or second sets of imaging data may include, for example, positron annihilation emission data, kV X-ray data, or MRI sub-samplings in k space. The controller may be further configured to calculate a normalization factor $k_2$ based on the first quantity of radiation, and the second quantity of radiation may be determined at least in part using the normalization factor and the second set of imaging data. The controller may be further configured to acquire a pre-scan image ($X_{prescan}$) of a target region of the patient located on a radiation therapy system platform, and to calculate a first normalization factor $k_1$ based on the pre-scan image ($X_{prescan}$), where the normalization factor k2 is a second normalization factor. Moving the patient from the first location to a second location may define a first shuttle pass, and moving the patient from the second location to the first location may define a second shuttle pass, where the controller may be configured to select a number of shuttle passes (N) and a cumulative dampening factor ($\alpha$), and calculate a normalized dampening factor ($\beta$), where $$\beta_i = \frac{\alpha^{i-1}}{\sum_{j=1}^{N} \alpha^{j-1}} \text{ for } i = 1, \ldots, N.$$

Furthermore, the first quantity of radiation ($D_{1,calculated}$) may be calculated based on the first set of imaging data and scaled by the first normalization factor $k_1$. The first quantity of radiation ($D_{1,calculated}$) may be calculated by multiplying the first set of imaging data with a radiation-firing matrix (RFM) of a treatment plan, spatially-filtered with a bitmask BFZ that corresponds to a spatial location of the target region, and multiplied by the first normalization factor $k_1$. Calculating the second normalization factor $k_2$ may comprise calculating a predicted cumulative dose by summing the dose delivered $D_{1,calculated}$ over (N−1) passes of radiation delivery ($D_{1,predicted\ cumulative}$) and calculating the difference between a planned dose ($D_{plan}$) and the first quantity of radiation ($D_{1,calculated}$), and taking the ratio of the dose difference over the predicted cumulative dose ($D_{1,predicted\ cumulative}$). The second quantity of radiation ($D_{2,calculated}$) may be calculated by multiplying the second set of imaging data with the RFM of the treatment plan, spatially-filtered with a bitmask BFZ that corresponds to a spatial location of the target region, and multiplied by the first normalization factor $k_2$. In some variations, the first normalization factor $k_1$ may be determined by $$k_1 = \frac{D_{plan}}{D_{0,raw}}$$

where $D_{plan}$ is a radiation dose or fluence as specified in the treatment plan, and $D_{0,raw}$ is a radiation fluence given by $$\left(D_{prescan} \times \frac{\text{treatment time}}{\text{prescan imaging time}}\right),$$

where $$D_{prescan} = A \cdot (X_{prescan} * RFM) \circ BFZ,$$

$D_{prescan}$ is the radiation fluence calculated by multiplying the pre-scan image ($X_{prescan}$) with a radiation-firing matrix (RFM) of a treatment plan, spatially-filtered with a bitmask BFZ that corresponds to a spatial location of the target region, and multiplied by a dose calculation matrix. Calculating the predicted cumulative dose ($D_{1,predicted\ cumulative}$) may comprise adding any negative radiation fluences resulting from multiplying the first set of imaging data with a radiation-firing matrix (RFM) of a treatment plan, spatially-filtered with a bitmask BFZ that corresponds to a spatial location of the target region.

Another variation of a radiation delivery system for delivering radiation during a treatment session may comprise a gantry, a therapeutic radiation source mounted on the gantry, an imaging system mounted on the gantry, and a controller in communication with the gantry, the radiation source, and the imaging system. The controller may be configured to acquire imaging data of a patient located on a platform with the imaging system, and apply a quantity of radiation to the patient with the radiation source to deliver a treatment planned amount of radiation $D_{plan}$, where the quantity of radiation is derived from the acquired imaging data. The controller may be further configured to stop the application of radiation to the patient, store the amount of radiation applied to the patient prior to stopping the application of radiation $D_{delivered,pre-interrupt}$ and the location of the platform when the radiation application was stopped, and resume radiation application to the patient while acquiring additional imaging data, where a second quantity of radiation applied to the patient is derived from the additional imaging data and adjusted according to a difference between $D_{plan}$ and $D_{delivered,pre-interrupt}$.

Resuming radiation application may comprise moving the patient platform back to the location of the platform when the application of radiation was stopped. The quantity of applied before stopping the application of radiation may be a first quantity of radiation and may be derived from imaging data $x_i$ acquired during the treatment session before stopping the application of radiation. Furthermore, the first quantity of radiation may be derived by multiplying acquired imaging data $x_i$ with a radiation-firing matrix RFM and applying a biological firing zone bitmask BFZ, where the RFM and the BFZ are calculated during a treatment planning session. In some variatinos, applying a quantity of radiation to the patient may comprise applying a first pass of radiation when moving the patient platform from a first location to a second location through a therapeutic radiation beam plane while acquiring a first set of imaging data $x_1$, where the quantity of radiation emitted during the first pass ($D_{1,calc}$) may be derived by multiplying the first set of imaging data $x_1$ with the radiation-firing matrix RFM and applying the biological firing zone bitmask BFZ to obtain $D_{1,raw}$ and scaling $D_{1,raw}$ by a first normalization factor $k_1$. Furthermore, in some variations the first normalization factor $k_1$ may be calculated by calculating a radiation quantity $D_{0,raw}$ by multiplying a pre-scan image of the patient acquired during the treatment session with the radiation-firing matrix RFM and applying the biological firing zone bitmask BFZ, calculating a cumulative predicted dose $D_{0,predicted\ cumulative}$ by multiplying $D_{0,raw}$ by a total number radiation passes N in the treatment session; and taking a ratio between $D_{plan}$ and the cumulative predicted dose $D_{0,predicted\ cumulative}$. In some variations, applying a quantity of radiation to the patient may further comprise applying a second pass of radiation when moving the patient platform from the second location to the first location through the therapeutic radiation beam plane while acquiring a second set of imaging data $x_2$, where the quantity of radiation emitted during the second pass ($D_{2,calc}$) is derived by multiplying the second set of imaging data $x_2$ with the radiation-firing matrix RFM and applying the biological firing zone bitmask BFZ to obtain $D_{2,raw}$, and scaling $D_{2,raw}$ by a second normalization factor $k_2$. Stopping the application of radiation to the patient may comprise stopping the application of radiation during the second pass of radiation. Additionally or alternatively, resuming radiation application to the patient may comprise acquiring a resumed set of imaging data $X_{2,resumed}$, and emitting a quantity of radiation, where the quantity of radiation may be derived by multiplying the resumed set of imaging data $X_{2,resumed}$ with the radiation-firing matrix RFM and applying the biological firing zone bitmask BFZ to obtain $D_{2,raw,post-interrupt}$, and scaling $D_{2,raw,post-interrupt}$ by the second normalization factor $k_2$, where the quantity of radiation may be applied before stopping the application of radiation is $D_{2,raw,pre-interrupt}$. Furthermore, resuming radiation application to the patient may further comprise applying a third pass of radiation when moving the patient platform from the first location to the second location through the therapeutic radiation beam plane while acquiring a third set of imaging data $x_3$, where the quantity of radiation emitted during the third pass may be derived by multiplying the third set of imaging data $x_3$ with the radiation-firing matrix RFM, applying the biological firing zone bitmask BFZ and scaling by a third normalization factor $k_3$. In some variations, the third normalization factor $k_3$ may be calculated by calculating a difference between $D_{plan}$ and a cumulative quantity of radiation applied in the first pass $D_{1,calc}$ and the second pass $D_{2,calc}$, calculating a cumulative predicted dose $D_{2,predicted\ cumulative}$ by multiplying $(D_{2,raw,pre-interrupt} + D_{2,raw,post-interrupt})$ by N−3, and taking a ratio between $(D_{plan}-(D_{1,calc}+D_{2,calc}))$ and the cumulative predicted dose $D_{2,predicted\ cumulative}$. In some variations, stopping the application of radiation to the patient may comprise stopping the application of radiation during the second pass of radiation and resuming radiation application to the patient may comprise acquiring a second pre-scan image of the patient, moving the patient platform back to the location of the patient platform when the application radiation was stopped, and acquiring a resumed set of imaging data $X_{2,resumed}$ and emitting a quantity of radiation derived by multiplying the resumed set of imaging data $X_{2,resumed}$ with the radiation-firing matrix RFM and applying the biological firing zone bitmask BFZ to obtain $D_{2,raw,post-interrupt}$, and scaling $D_{2,raw,post-interrupt}$ by a resumed normalization factor $k_{2\_resumed}$, where the quhdntity of radiation applied before stopping the application of radiation is $D_{2,raw,pre-interrupt}$. Furthermore, the resumed normalization factor $k_{2\_resumed}$ may be calculated by calculating a radiation quantity $D_{2,raw,post-interrupt}$ by multiplying the second pre-scan image of the patient with the radiation-firing matrix RFM and applying the biological firing zone bitmask BFZ, calculating a cumulative predicted dose $D_{2,predicted\ cumulative}$ by multiplying $(D_{2,raw,pre-interrupt}+D_{2,raw,post-interrupt})$ by N−2, and taking a ratio between $D_{plan}$ and the cumulative predicted dose $D_{2,predicted\ cumulative}$. Resuming radiation application to the patient may further comprise applying a third pass of radiation when moving the patient platform from the first location to the second location through the therapeutic radiation beam plane while acquiring a third set of imaging data $x_3$, where the quantity of radiation emitted during the third pass is derived by multiplying the third set of imaging data $x_3$ with the radiation-firing matrix RFM, applying the biological firing zone bitmask BFZ and scaling by a third normalization factor $k_3$. The third normalization factor $k_3$ may be calculated by calculating a difference between $D_{plan}$ and a cumulative quantity of radiation applied in the first pass $D_{1,calc}$ and the second pass $D_{2,calc}$, calculating a cumulative predicted dose $D_{2,predicted\ cumulative}$ by multiplying $(D_{2,raw,pre-interrupt}+D_{2,raw,post-interrupt})$ by N−3; and taking a ratio between $(D_{plan}-(D_{1,calc}+D_{2,calc}))$ and the cumulative predicted dose $D_{2,predicted\ cumulative}$.

Another variation of a radiation delivery system may comprise a gantry, a therapeutic radiation source mounted on the gantry and configured to apply radiation in a radiation treatment beam plane, a plurality of PET detectors mounted on the gantry, a platform movable relative to the gantry, and a controller in communication with the gantry, the therapeutic radiation source, and the platform. The controller may be configured to acquire an image of a patient on the platform, calculate a normalization factor based on the image of the patient, and deliver radiation to the patient across a pre-selected number of shuttle passes. In each shuttle pass, the controller may be configured to update a radiation-firing matrix of a treatment plan with the calculated normalization factor, move the platform from a first pre-determined location to a second pre-determined location and back to the first pre-determined location such that a target region in the patient crosses the radiation treatment beam plane at least twice, acquire PET data using the PET detectors, deliver radiation to the patient based on the updated radiation-firing matrix and acquired PET data, calculate fluence delivered to the patient when the platform has moved back to the first pre-determined location, calculate a fluence difference between the fluence delivered to the patient and a treatment plan fluence and calculate an updated normalization factor based on the fluence difference.

The PET detectors may be co-planar with the radiation treatment beam plane, and in some variations the acquired image may be a PET image. For example, the calculation of the normalization factor may comprise calculating a mean of a PET intensity of the target region in the acquired PET image. The pre-selected number of shuttle passes may be even. For example, the pre-selected number of shuttle passes may be two or more. In some variatinos, calculating an updated normalization factor may comprise calculating a mean fluence value of the radiation emitted by the therapeutic radiation source. Additionally or alternatively, calculating an updated normalization factor may comprise calculating a ratio of a mean planned dose value of radiation to the target region and a mean delivered dose value of the radiation. Delivering radiation based on the updated radiation-firing matrix and acquired PET data may comprise multiplying the updated radiation-firing matrix with one or more lines-of-response (LORs) of the acquired PET data to derive a delivery fluence map and generating radiation using the therapeutic radiation source according to the delivery fluence map. In some variations, the radiation delivery system may further comprise a movable jaw disposed over the therapeutic radiation source and a multi-leaf collimator coupled to the jaw, where the treatment plane is defined by a position of the movable jaw and a configuration of the multi-leaf collimator relative to the therapeutic radiation source. In these variations, the controller may be configured to move the movable jaw from a first jaw location to a second jaw location back to the first jaw location when radiation is delivered to the patient. In some variations, the controller may be configured to calculate a predicted dose and dose value histogram by adjusting the image by the calculated normalization factor.

Another variation of a radiation delivery system may comprise a gantry, a therapeutic radiation source, a radiation therapy system platform, and a controller. A movable jaw and a multi-leaf collimator may both be disposed in a radiation beam path of the radiation source, and a position of the movable jaw and a configuration of the multi-leaf collimator relative to the radiation source may define a treatment plane. Additionally, the controller may be in communication with the gantry, the radiation source, and the radiation therapy system platform. The controller may be configured to (a) move a patient located on the platform by moving the platform from a first pre-determined location to a second pre-determined location such that one or more target regions in the patient crosses the treatment plane; and (b) deliver radiation to the patient with the radiation source when a portion of the one or more target regions crosses the treatment plane, wherein delivery of the radiation comprises moving the movable jaw from a first jaw location to a second location back to the first jaw location while emitting radiation from the radiation source before moving to the next platform location.

Moving the platform may comprise moving the platform in a series of pre-defined incremental patient platform locations, and delivering radiation to the patient may comprise delivering radiation at each platform location where the target regions cross the treatment plane. Moving the platform comprises translating the platform along a longitudinal axis and wherein moving the movable jaw comprises moving the jaw such that the treatment plane shifts along the longitudinal axis. Moving the movable jaw may shift the treatment plane from about 3 cm to about 6 cm along the longitudinal axis and/or at a speed of about 0.5 cm/s. Furthermore, the controller may be configured to acquire an image of the patient before radiation is delivered to the patient. For example, the system may comprise a plurality of PET detectors configured to acquire PET data including lines-of-response (LORs), where delivering radiation to the patient may comprise multiplying a radiation-firing matrix of a treatment plan with one or more LORs to derive a delivery fluence map and generating radiation using the therapeutic radiation source according to the delivery fluence map. THe acquired image may be a PET image. In some variations, the controller may be configured to repeat steps (a) and (b) a pre-selected number of shuttle passes. For example, the pre-selected number of shuttle passes may be two or more.

Another variation of a radiation delivery system may comprise a gantry, a therapeutic radiation source, and a controller in communication with the gantry and the radiation source. The controller may be configured to calculate a radiation fluence delivered to a patient target region during a previous radiation delivery session, compare the delivered radiation fluence to the target region with treatment plan fluence to the target region and calculate a fluence difference, calculate a radiation-firing matrix based on the calculated fluence difference; and deliver radiation to the patient in a subsequent radiation delivery session based on the calculated radiation-firing matrix and PET data acquired during the subsequent radiation delivery session. Comparing the delivered radiation fluence and the planned radiation fluence may comprise comparing a mean radiation fluence delivered to the target region with a mean treatment plan fluence to the target region and calculating a fluence difference by taking the difference between the mean delivered radiation fluence and the mean treatment plan fluence. In some variations, PET data may comprise line-of-response (LOR) data.

One variation of a method for radiation delivery may comprise acquiring an image of a patient on a radiation therapy system platform, where the radiation therapy system further comprises a therapeutic radiation source configured to apply radiation in a treatment plane and a plurality of PET detectors, calculating a normalization factor based on the image of the patient, and delivering radiation to the patient across a pre-selected number of shuttle passes. Each shuttle pass may comprise updating a radiation-firing matrix of a treatment plan with the calculated normalization factor, moving the patient platform from a first pre-determined location to a second pre-determined location such that a target region in the patient crosses the treatment plane once, acquiring PET data using the PET detectors, delivering radiation to the patient based on the updated radiation-firing matrix and acquired PET data. When the platform has moved to the second pre-determined location, the radiation therapy system may calculate the fluence delivered to the patient, calculate a fluence difference between the fluence delivered to the patient and a treatment plan fluence, and calculate a fluence difference between the fluence delivered to the patient and a treatment plan fluence. The PET detectors may be co-planar with the treatment plane. Acquiring an image may comprise acquiring a PET image. The pre-selected number of shuttle passes may be even, e.g., two or more. Calculating the normalization factor may comprise calculating a mean of a PET intensity of the target region in the acquired PET image. Calculating an updated normalization factor may comprise calculating a mean fluence value of the radiation emitted by the therapeutic radiation source. Alternatively or additionally, calculating an updated normalization factor may comprise calculating a ratio of a mean planned dose value of radiation to the target region and a mean delivered dose value of the radiation. Delivering radiation based on the updated radiation-firing matrix and acquired PET data may comprise multiplying the updated radiation-firing matrix with one or more lines-of-response (LORs) of the acquired PET data to derive a delivery fluence map and generating radiation using the therapeutic radiation source according to the delivery fluence map. The radiation therapy system may further comprise a movable jaw disposed over the therapeutic radiation source and a multi-leaf collimator coupled to the jaw, where the treatment plane may be defined by a position of the movable jaw and a configuration of the multi-leaf collimator relative to the therapeutic radiation source. The method may further comprise moving the movable jaw from a first jaw location to a second jaw location back to the first jaw location while delivering radiation to the patient. Some variations may further comprise calculating a predicted dose and dose value histogram by adjusting the image by the calculated normalization factor.

Another variation of a method for radiation delivery may comprise (a) moving a patient on a radiation therapy system platform from a first pre-determined location to a second pre-determined location where the radiation therapy system may further comprise a therapeutic radiation source, a movable jaw and a multi-leaf collimator both disposed in a radiation beam path of the therapeutic radiation source, where a position of the movable jaw and a configuration of the multi-leaf collimator relative to the therapeutic radiation define a treatment plane, and where moving the patient from the first location to the second location causes one or more target regions in the patient to cross the treatment plane, and (b) delivering radiation to the patient when a portion of the one or more target regions crosses the treatment plane. Delivering radiation may comprise moving the movable jaw from a first jaw location to a second jaw location back to the first jaw location while emitting radiation from the therapeutic radiation source before moving to the next platform location. Moving the patient platform may comprise moving the platform in a series of pre-defined incremental patient platform locations, and where delivering radiation to the patient comprises delivering radiation at each platform location where the target regions cross the treatment planc. Moving the platform may comprise translating it along a longitudinal axis and where moving the movable jaw comprises moving the jaw such that the treatment plane shifts along the longitudinal axis. Moving the movable jaw may shift the treatment plane from about 3 cm to about 6 cm along the longitudinal axis. Moving the movable jaw shifts the treatment plane at a speed of about 0.5 cm/s. The method may further comprise acquiring an image of the patient before delivering radiation to the patient. The radiation therapy system may further comprise a plurality of PET detectors configured to acquire PET data including lines-of-response (LORs), and where delivering radiation to the patient comprises multiplying a radiation-firing matrix of a treatment plan with one or more LORs to derive a delivery fluence map and generating radiation using the therapeutic radiation source according to the delivery fluence map. The acquired image may be a PET image. The method may further comprise repeating steps (a) and (b) a pre-selected number of shuttle passes, where the pre-selected number of shuttle passes is two or more.

Another variation of a method for radiation delivery may comprise calculating a radiation fluence delivered to a patient target region during a previous radiation delivery session, comparing the delivered radiation fluence to the target region with treatment plan fluence to the target region and calculate a fluence difference, calculating a radiation-firing matrix based on the calculated fluence difference, and delivering radiation to the patient in a subsequent radiation delivery session based on the calculated radiation-firing matrix and PET data acquired during the subsequent radiation delivery session. Comparing the delivered radiation fluence and the planned radiation fluence may comprise comparing a mean radiation fluence delivered to the target region with a mean treatment plan fluence to the target region and calculating a fluence difference by taking the difference between the mean delivered radiation fluence and the mean treatment plan fluence. In some variations, PET data may comprise line-of-response (LOR) data.

BRIEF DESCRIPTION OF THE DRAWINGS

FIG. 3C depicts a table representing delivered dose to a target region after one shuttle pass and after eight shuttle passes.

FIG. 8A depicts one variation of a method for radiation delivery.

FIG. 9A depicts DVH curves after one shuttle pass, FIG. 9B depicts DVH curves after two shuttle passes, FIG. 9C depicts DVH curves after three shuttle passes, and FIG. 9D depicts DVH curves after four shuttle passes.

FIG. 11A depicts DVH plots when negative fluence values are incorporated as part of radiation delivery.

FIG. 11B depicts DVH plots when negative fluence values are not incorporated as part of radiation delivery.

FIG. 12A depicts the projection of the planned dose distribution on the IEC-Z/IEC-X plane, FIG. 12B depicts the projection of the planned dose distribution on the IEC-Z/IEC-Y plane, and FIG. 12C depicts the projection of the planned dose distribution on the IEC-Y/IEC-X plane.

FIG. 13A depicts the projection of the delivered dose distribution on the IEC-Z/IEC-X plane, FIG. 13B depicts the projection of the delivered dose distribution on the IEC-Z/IEC-Y plane, and FIG. 13C depicts the projection of the delivered dose distribution on the IEC-Y/IEC-X plane.

FIGS. 14A-14C depict multiple views of the γ (gamma) metric distribution. FIG. 14A depicts the projection of the γ (gamma) metric distribution on the IEC-Z/IEC-X plane, FIG. 14B depicts the projection of the γ (gamma) metric distribution on the IEC-Z/IEC-Y plane, and FIG. 14C depicts the projection of the γ (gamma) metric distribution on the IEC-Y/IEC-X plane.

DETAILED DESCRIPTION

Radiation Therapy System

Figure 1A:
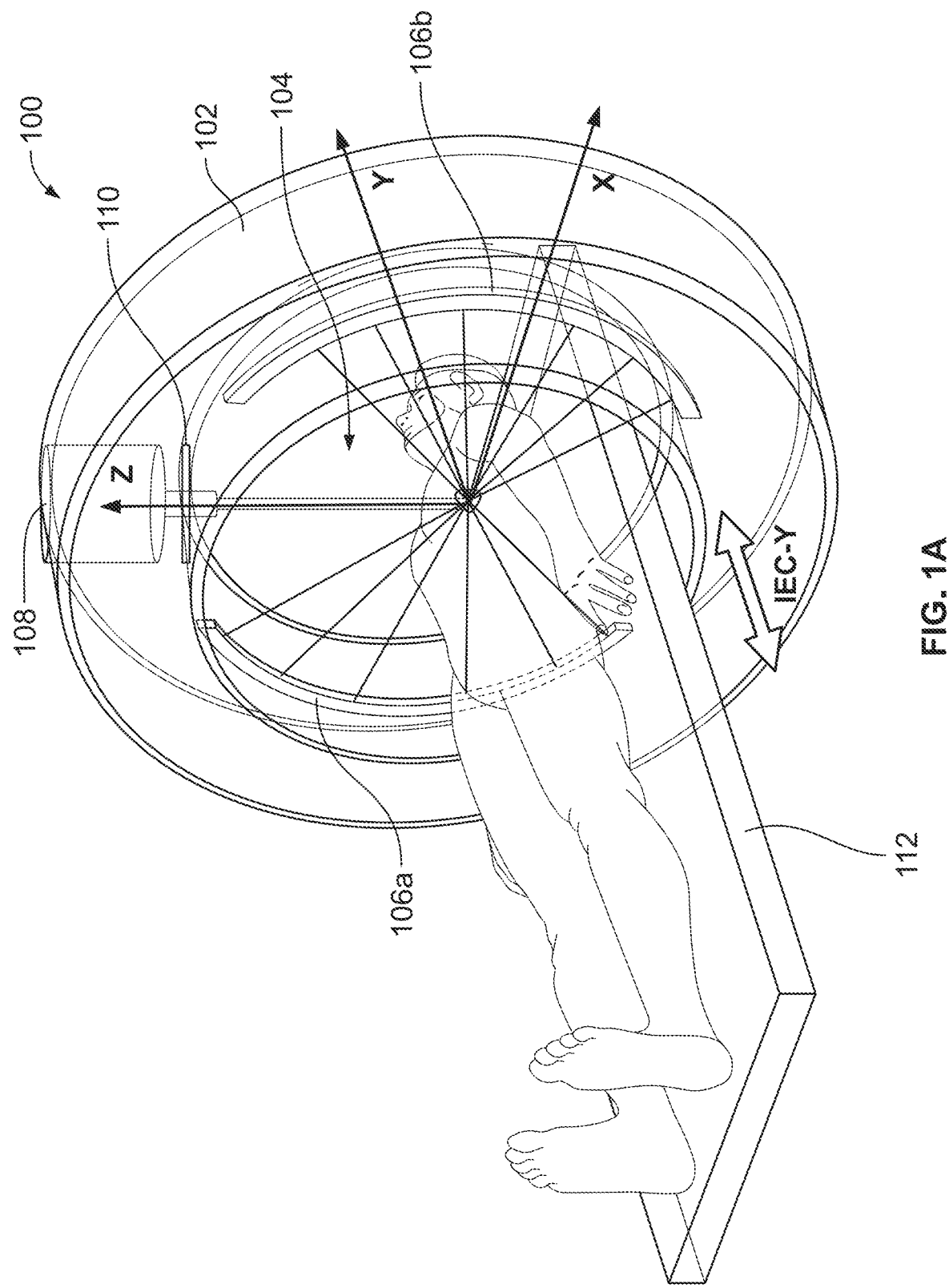
FIG. 1A depicts one variation of a radiation therapy system.

A radiation therapy system that may be used in shuttle mode radiation delivery may comprise a rotatable gantry that rotates about a patient treatment region, a therapeutic source mounted on the rotatable gantry, and a patient platform movable within or through the patient treatment region. The rotatable gantry may be configured to rotate 0°-360° (e.g., a continuously rotatable gantry) or to only rotate along arc segments that sweep a subset of angles (e.g., 0°-180°, 0°-270°, etc.). One example of a therapeutic radiation source is a linear accelerator (linac). One or more beam-shaping elements may be disposed in the beam path of the therapeutic radiation source to define a treatment plane. For example, beam-shaping elements may comprise a jaw and a dynamic multi-leaf collimator (MLC). The jaw may be located between the therapeutic radiation source and the MLC, or may be located below the MLC. Alternatively, a jaw may be a split jaw where a first portion of the jaw is located between the therapeutic radiation source and the MLC. and a second portion of the jaw is located below the MLC and coupled to the first portion of the jaw such that both portions move together. The jaw may be movable within the beam of the therapeutic radiation source such that a treatment plane defined by the jaw may shift in a direction that is parallel to the motion of the patient platform. For example, if the patient platform moves through the patient treatment region in the IEC-Y direction, the jaw and MLC may define a treatment plane in the IEC-XZ plane, and moving the jaw may shift the treatment plane along the IEC-Y direction. The MLC and the jaw may be separate or de-coupled such that shifting or moving the jaw does not move the MLC, but in other variations, the MLC and the jaw may be coupled together such that shifting or moving the jaw also causes a corresponding shift or movement of the MLC. Some variations of a radiation therapy system may comprise a radiation detector mounted on the gantry opposite the therapeutic radiation source. For example, some variations may comprise a MV radiation detector located opposite a linac.

Furthermore, some radiation therapy systems may comprise one or more PET detectors, which may be mounted on the same rotatable gantry or on a separate/second gantry that may or may not be rotatable about the patient treatment region. Lines-of-response (LORs) defined by a pair of coincident 511 keV photons emitted by a positron annihilation event may be detected by the PET detectors and transmitted to a system controller. In some variations, a patient may be injected with a PET tracer prior to a treatment session, and LORs from the PET tracer may be detected by the PET detectors. For example, the PET tracer may accumulate at patient regions with elevated metabolic rates, such as tumor regions. The system controller may be in communication with all of the components of a radiation therapy system, and may, for example, generate commands to the therapeutic radiation source, and/or gantry, and/or beam-shaping elements, and/or patient platform based on the data acquired by the PET detectors and/or MV detector. The system controller may also comprise one or more processors that may be programmed or configured to perform any of the calculations and methods described herein. The controller may also comprise one or more memories that may store data associated with any of the calculations and methods described herein, including, but not limited to, imaging data (e.g., LORs data as detected by the PET detectors), radiation delivery parameters and/or adjustment factors, machine commands, machine configurations, sensor data, and any other data as described herein.

Figure 1B:
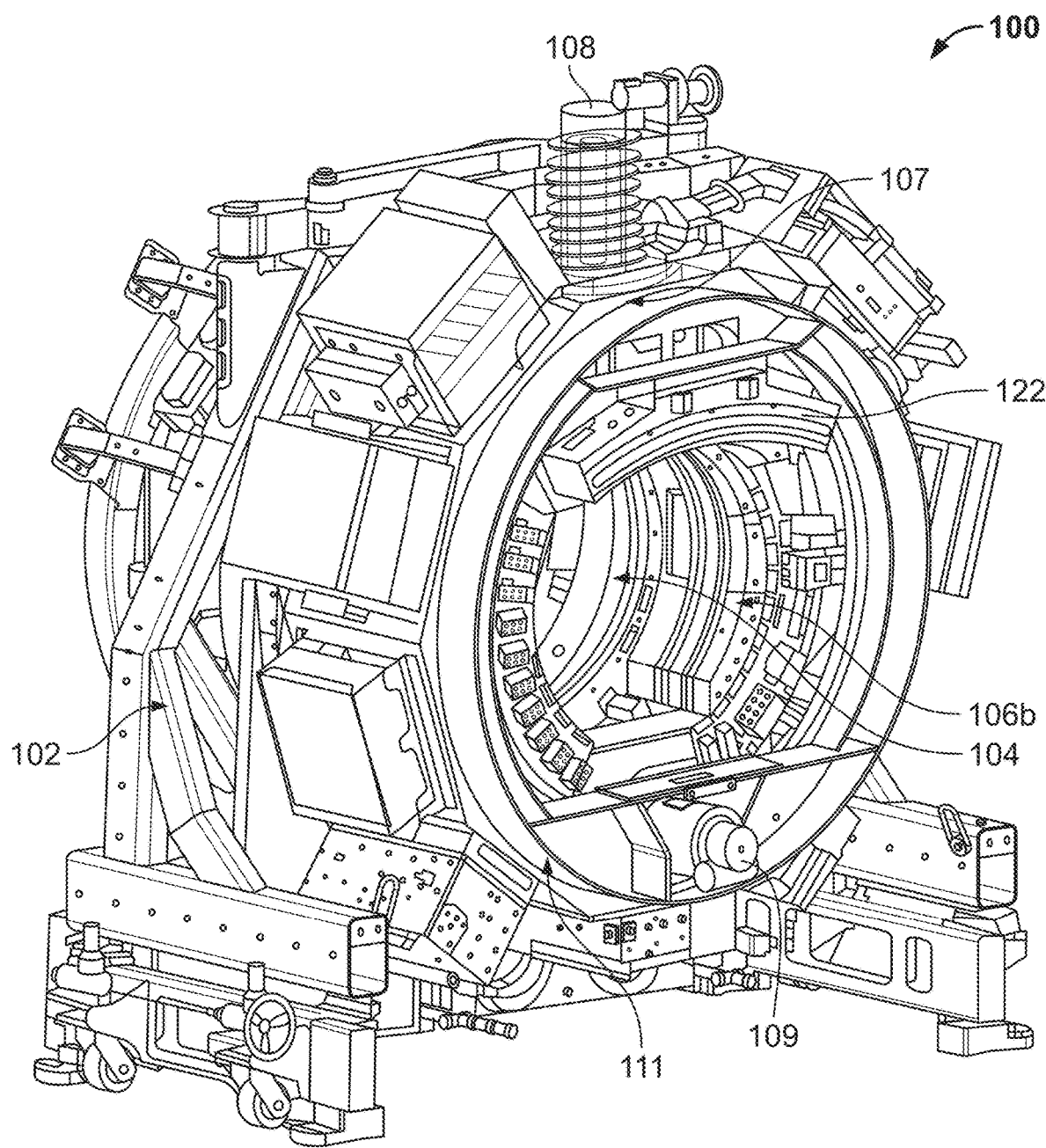
FIG. 1B depicts a perspective component view of a radiation therapy system (e.g., the radiation therapy system of FIG. 1A).

One variation of a radiation therapy system is depicted in FIG. 1A. FIG. 1A depicts one variation of a radiation therapy system that may be used in shuttle mode radiation delivery. The radiation therapy system (100) may comprise a gantry (102) rotatable about a patient treatment region (104), one or more PET detectors (106) mounted on the gantry, a therapeutic radiation source (108) mounted on the gantry, a beam-shaping module (110) disposed in the beam path of the therapeutic radiation source, and a patient platform (112) movable within the patient treatment region (104). The beam-shaping module (110) may comprise a movable jaw and a dynamic multi-leaf collimator (MLC). The beam-shaping module may be arranged to provide variable collimation width in the longitudinal direction of 1 cm, 2 cm or 3 cm at the system iso-center (e.g., a center of a patient treatment region). The jaw may be located between the therapeutic radiation source and the MLC, or may be located below the MLC. Alternatively, the beam-shaping module may comprise a split jaw where a first portion of the jaw is located between the therapeutic radiation source and the MLC, and a second portion of the jaw is located below the MLC and coupled to the first portion of the jaw such that both portions move together. FIG. 1B is a perspective component view of the radiation therapy system (100). As shown there, the beam-shaping module may further comprise a primary collimator or jaw (107) disposed above the binary MLC (122). Optionally, the radiation therapy system (100) may further comprise a kV CT scanner (109) on a rotatable ring (111) that is attached to the rotatable gantry (102) such that rotating the gantry (102) also rotates the ring (111). The therapeutic radiation source or linac (108) and the PET detectors (106) may be mounted on the same cross-sectional plane of the gantry (i.e., PET detectors are co-planar with a treatment plane defined by the linac and the beam-shaping module), while the kV CT scanner and ring may be mounted on a different cross-sectional plane (i.e., not co-planar with the treatment plane).

Figure 1C:
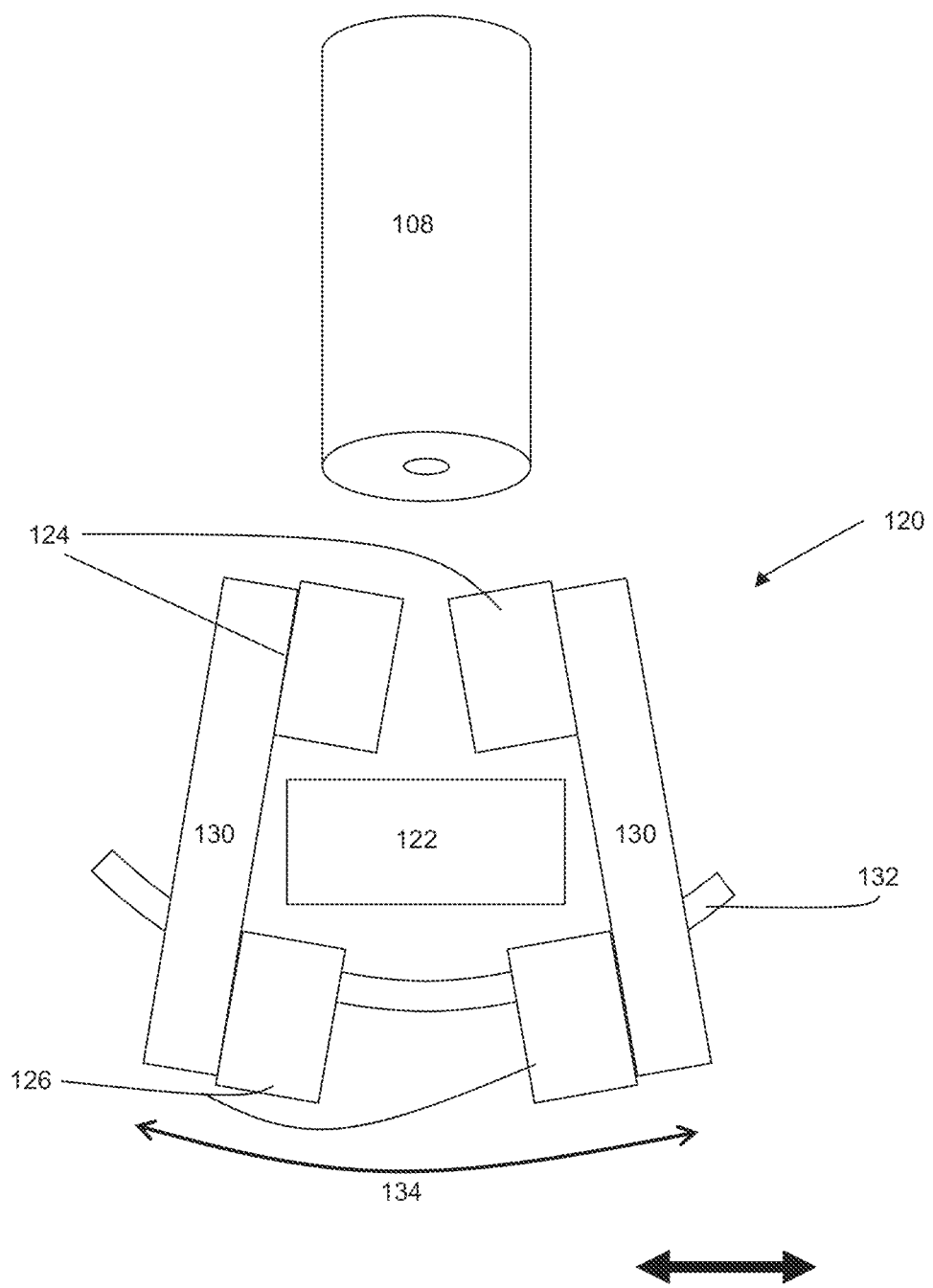
FIG. 1C depicts one variation of a beam-shaping module.

FIG. 1C is a schematic depiction of one variation of a beam-shaping module comprising a split jaw (120) and a dynamic MLC (122). In this variation, the dynamic MLC (122) may be a binary MLC but could be any type of MLC (e.g., a 2-D MLC). The split jaw (120) may comprise upper jaws (124) located between the therapeutic radiation source (128) (e.g., linac) and the MLC (122), and lower jaws (126) located below the MLC (122). The upper jaws (124) and the lower jaws (126) may be coupled together by one or more plates (130) or frames. The jaw may be mounted on one or more curved linear rails. For example, the split jaw (120) may be slidably mounted on one or more curved linear rails (132). The one or more plates or frames of the split jaw may have one or more slots that are sized and shaped to be larger than the cross-sectional size of the rails such that the slots can slide over the rails (as indicated by arrow (134)). Optionally, there may be an additional rail orthogonal to the rail (132) to provide further support to the jaw. The rails (132) are curved in this example, but they may not be curved (i.e., they may be straight, without any curves) in other variations. The jaw may be coupled to an actuator or motor that moves the position of the jaw along the curved linear rail. Movement of the jaw along the rail may result in a corresponding shift of a treatment plane along the IEC-Y axis (i.e., parallel to the axis of motion of the patient platform). In other variations, the jaw may instead be mounted to the gantry via one or more movable or rotatable attachment mechanisms, such as one or more hinges or pivots. The jaw may be able to move from about 0.5 cm to about 2 cm to the right or to the left of the isocenter, with a total range of movement (end-to-end) from about 1 cm to about 4 cm. This may correspond to a similar shift in the treatment plane, where the treatment plane may shift along the longitudinal axis of the patient platform with a total range of movement of from about 1 cm to about 4 cm. It should be understood that the total range of movement along the longitudinal axis of the patient platform (e.g., IEC-Y) may be from about 1 cm to about 12 cm, e.g., about 1 cm, about 2 cm, about 3 cm, etc. In some variations, a binary MLC may comprise 64 leaves that define an axial plane (e.g., IEC-XZ) that are each 0.6 cm in width at iso-center leading to a field-of-view (FOV) of ~40 cm. The jaw actuator may be configured to move the jaw at a speed of about 0.25 cm/s to about 2 cm/s, e.g., about 0.5 cm/s, about 1 cm/s, etc. In some variations, the speed of the jaw may be greater than the speed of the patient platform. While the beam-shaping module depicted and described in FIGS. 1A-1C comprises a jaw and a MLC that are not movably attached to each other (i.e., moving or shifting the jaw does not necessarily move to shift the MLC), in other variations, the jaw and the MLC may be movable attached (i.e., the jaw and the MLC move or shift together in concert).

In some variations, the radiation therapy system may comprise a first array of PET detectors (106a) and a second array of PET detectors (106b) disposed across from the first array, a linear accelerator (108) or linac, and a beam-shaping module (110) comprising jaws and a dynamic binary MLC. The system may further comprise a controller that is in communication with the gantry, PET detectors, linac, and MLC, where the controller has one or more memories that may store treatment plans, radiation-firing matrices, fluence maps, system instructions/commands, and a processor configured to execute the calculations and methods described herein. A patient located or disposed on the patient platform (112) within the patient treatment region (104) may have been injected with a PET tracer that emits positrons, and the PET tracer may accumulate at particular regions of the patient (e.g., such as tumor regions). The annihilation of a positron with a nearby electron may result in the emission of two photons traveling in opposite directions to define a LOR or positron annihilation emission path. PET detectors may detect one or more LORs. In some variations, the PET detectors may be time-of-flight PET detectors, which may help to identify the location of the positron annihilation event. A previously-calculated treatment plan P and/or a radiation-firing matrix RFM may be updated in accordance with data acquired by an MV detector located opposite the therapeutic radiation source, and/or the LOR data and/or PET imaging data acquired by the PET detectors to update a treatment plan fluence map such that the linac and MLC leaf configuration/beamlet selection account for tumor movement. The treatment plan fluence map may be updated using LOR data and/or PET imaging data and/or MV detector data as the patient is moved through the patient treatment region (e.g., in pre-defined patient platform steps or increments, or continuous patient platform movement through the patient treatment region and/or treatment plane). Optionally, radiation therapy system (100) may comprise a CT imaging system mounted on the same gantry as the therapeutic radiation source or mounted on a separate gantry. Additional details and examples of PET-based radiation therapy systems are described in U.S. patent appication Ser. No. 15/814,222, filed Nov. 15, 2017 which is hereby incorporated by reference in its entirety.

The gantry (102) may be configured to rotate at a rate from about 15 RPM to about 70 RPM (e.g., about 50 RPM, about 60 RPM), the binary dynamic MLC may be configured to change leaf configurations within about 15 ms or less (e.g., about 10 ms or less, about 8 ms or less), and the patient platform (112) may be configured to move at a rate of about 0.5 mm/s or less. For example, a high-speed binary multi-leaf collimator may comprise leaf actuating mechanisms having a spring system coupled to a pneumatic system to provide sufficient motive force to move a MLC leaf between open and closed configurations within the time constraints described above. The gantry (102) may move to (and/or across) discrete, pre-defined circumferential firing positions as it rotates. Some systems have about 100 firing positions or angles (e.g., from about 0 degrees to about 360 degrees, where each position is separated by a regular angular interval).

A treatment plan may specify the radiation dose to be delivered by a radiation therapy system to each target region in a patient. The fluence map and/or dose map of a treatment plan may be used to determine the jaw position/configuration, MLC position/configuration, gantry position and/or motion, and the couch position and/or motion during a treatment session. In some variations, a radiation-firing matrix (RFM) may be calculated as part of treatment planning. A RFM may be a matrix that designates the conversion from partial images (e.g., a set of LORs or incomplete image data) to a radiation beamlet pattern and/or beamlet intensities to be applied to the patient during a treatment session. For example, in biology-guided radiation therapy such as emission-guided radiation therapy where therapeutic radiation is applied to target region(s) based on detected PET LORs, RFM may be multiplied with LOR data during a treatment session to generate a fluence map that specifies the radiation dose to be delivered to each patient target region. Additional details regarding treatment planning methods and calculation of radiation-firing matrices are provided in U.S. Prov. Pat. Appln. No. 62/537,384, filed Jul. 26, 2017, which is hereby incorporated by reference in its entirety.

Dose Modulation Artifact

Treatment plans and/or RFMs are calculated based upon images and data of the patient and/or target regions prior to a treatment session, often weeks or days before the treatment session. It is not uncommon for target regions, especially target regions in or in the vicinity of the lungs (e.g., lung tumors) to move during the treatment session and in particular, to deviate from its location during treatment planning. The irregular and/or unpredictable motion of the target region(s), in conjunction with the motion of the jaws, and/or MLC, and/or couch, may modulate the delivered dose such that radiation is provided to non-target tissue and/or certain areas of the target region are over-irradiated or under-irradiated (e.g., hot spots and cold spots, respectively). As the patient platform or couch advances in the treatment region along the longitudinal direction (IEC-Y), the target volume is irradiated using a fan-beam (e.g., treatment plane) of radiation as defined by the beam-shaping elements of the system. Radiation therapy systems with fast-rotating gantries (e.g., more than about 15 RPM, for example, about 60 RPM or about 70 RPM) and rapid binary MLCs (e.g., with leaf transition times from about 8 ms to about 15 ms) may result in a pitch (i.e., ratio of couch movement in one rotation and the collimator thickness along IEC-Y) that is less than about 0.3. It has been suggested that patient and couch motion along IEC-Y (longitudinal direction) may be a significant contributor to dose modulation artifacts.

Figure 2A:
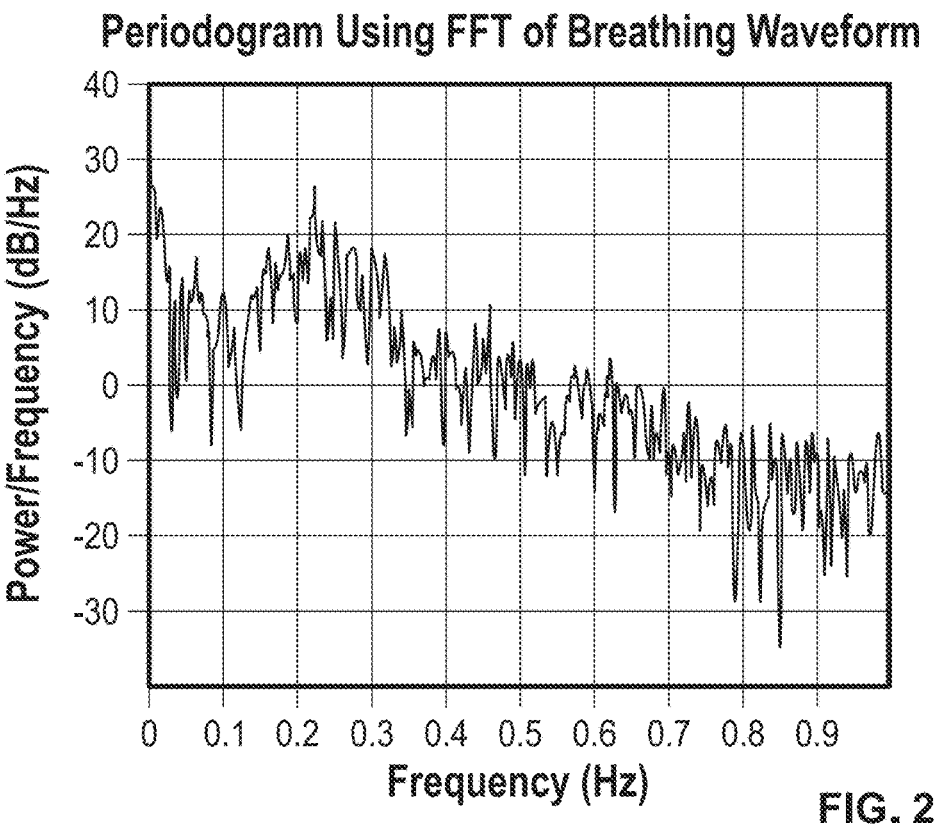
FIG. 2A depicts a plot that represents the frequency spectrum of breathing motion.
Figure 2B:
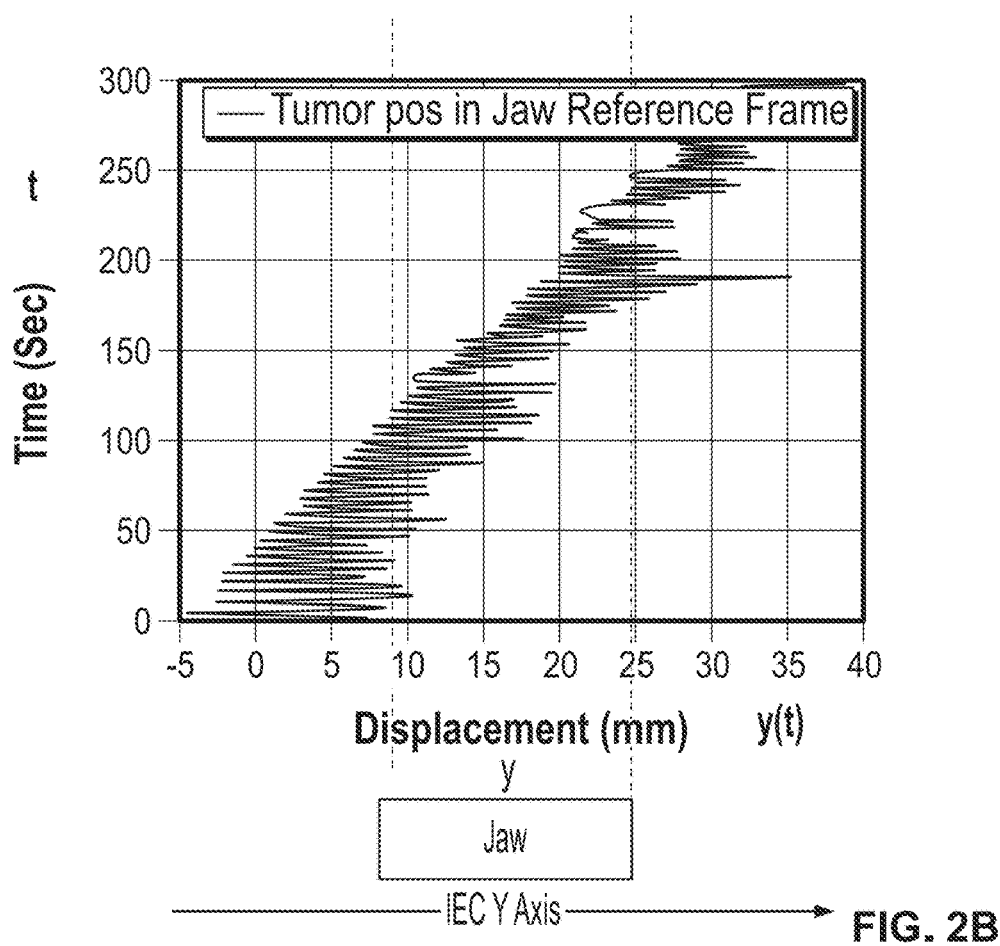
FIG. 2B depicts a plot that represents the motion of a target region during a treatment session.

One example of dose modulation due to tumor motion is depicted in FIGS. 2A-2D. FIGS. 2A and 2B are plots that represent tumor motion (due to respiratory motion) on a radiation therapy system having a patient platform or couch that moves at a speed of about 0.5 mm/s or less, and a binary MLC leaf size of 20 mm in the longitudinal direction (e.g., IEC-Y), where the time to traverse the beam in the longitudinal direction would be about 40 seconds (20 mm/[0.5 mm/s]). The time to traverse the beam may be referred to as "jaw dwell time". While in the transverse plane (e.g., IEC-XZ plan), the time scale for the binary MLC (e.g., leaf transition speed) is an order higher at about 0.01 seconds in a system with 100 firing positions. In this radiation therapy system, the rates of binary MLC leaf opening and closing are relatively fast as compared to the speed of couch motion. As depicted in FIG. 2A, the dominant component of respiratory motion has a frequency of about 0.2 Hz. Dose modulation due to respiratory motion and patient platform motion can be explained as a function of the variations in the jaw dwell time. The dose D received at any given point (y) along the longitudinal axis (IEC-axis) in the jaw reference frame may be represented as follows:

$$D(y) = \int_{-t_{ON}/2}^{t_{ON}/2} B(y - y(t)) dt$$

where y is the location of the beam center or the machine in the longitudinal direction (IEC-Y) and B defines the beam profile for a given system. y(t) is the profile of the tumor motion as seen in the jaw reference frame and can be described as:

$$y(t) = v_{couch} t + y_{breathing}(t)$$

Figure 2C:
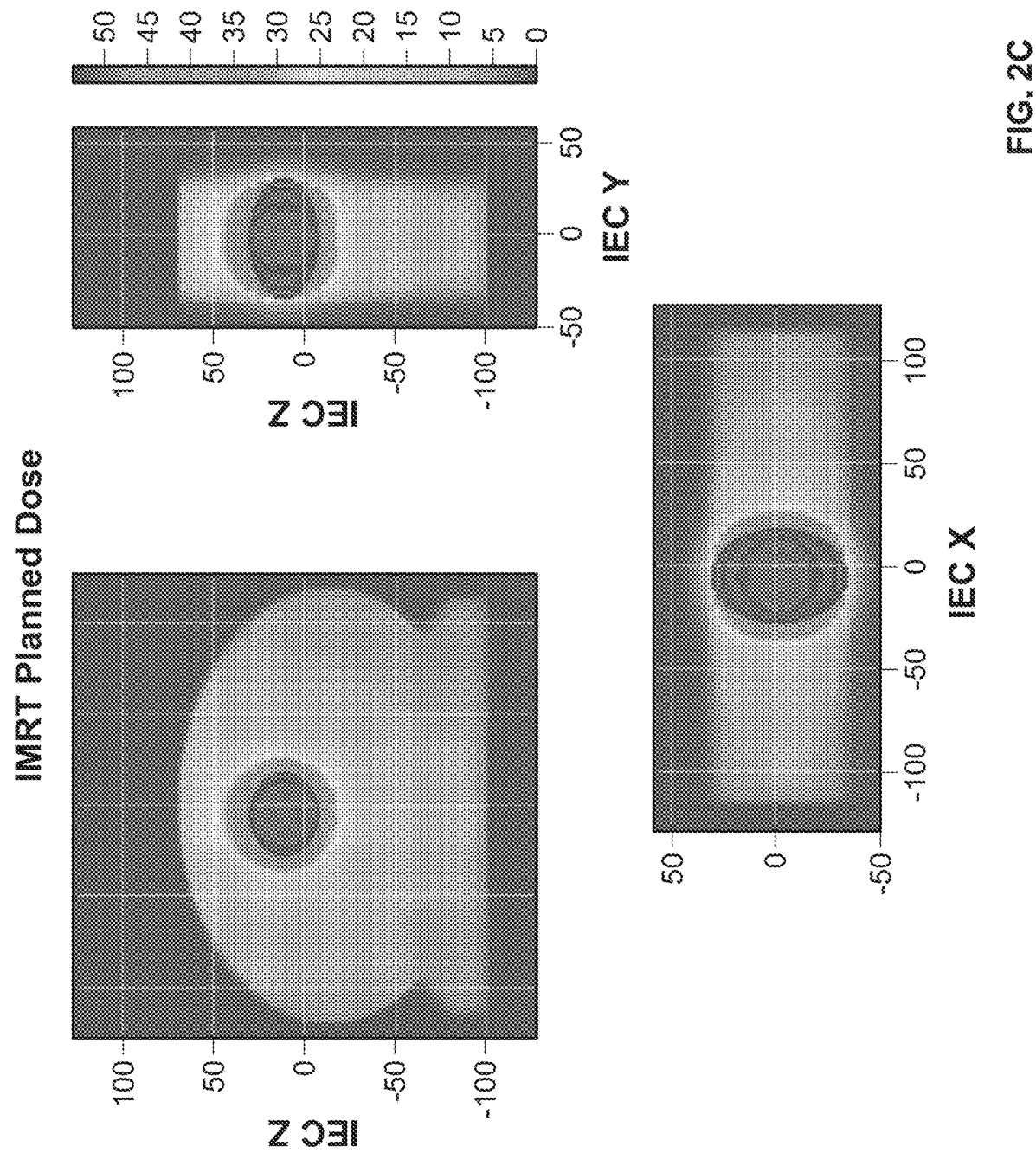
FIG. 2C depicts planned dose distribution plots.
Figure 2D:
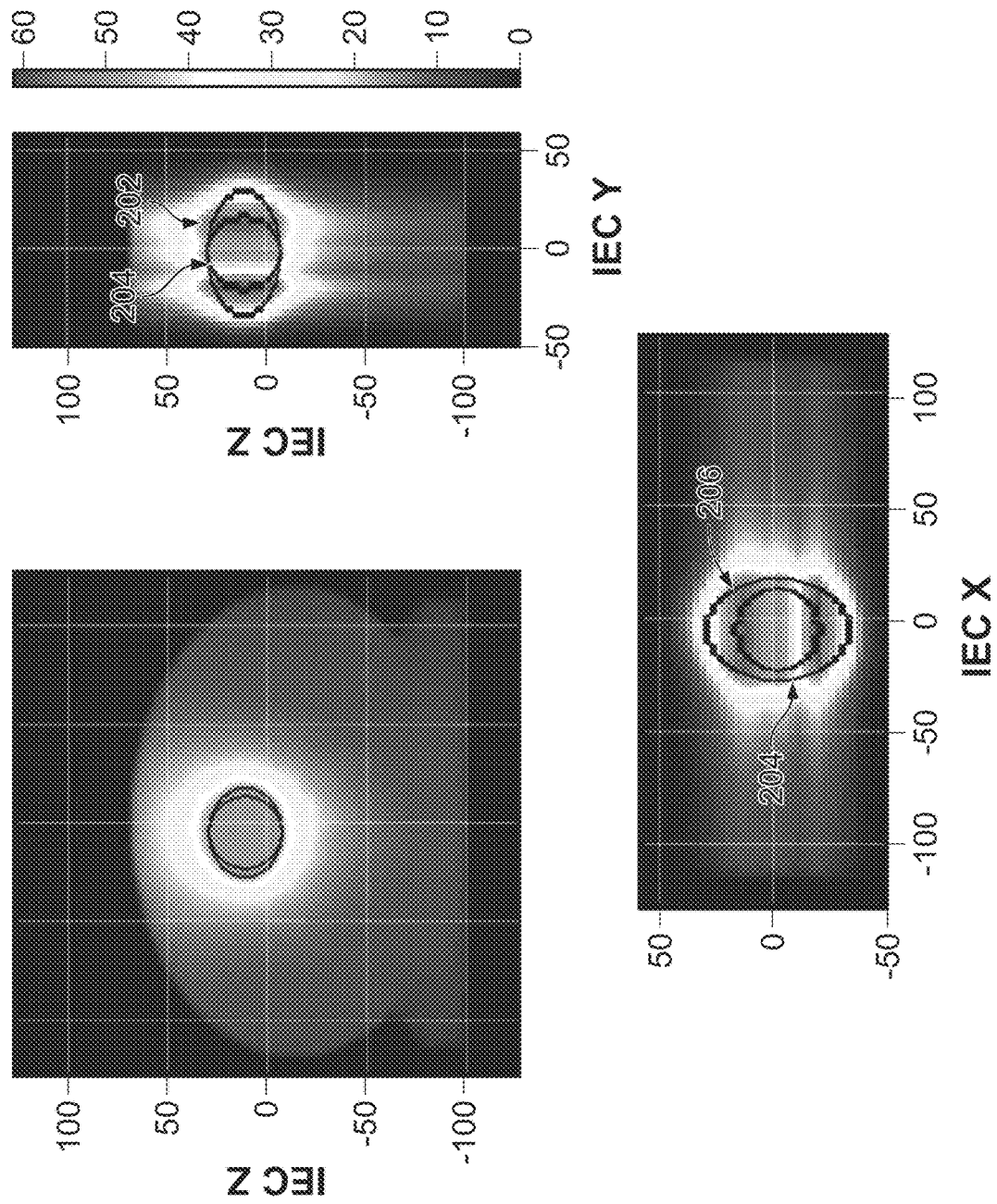
FIG. 2D depicts a delivered dose distribution plot.

The integration over time represents the averaging of the motion over a certain period of time as described in the paragraph above and is also represented in FIG. 2B. Because of breathing motion, a target region (e.g., a lung tumor) may shift forward and backward, in and out of the jaw window (200), resulting in irregular dose delivery to that target region. The dose at a given point y may be directly proportional to the dwell time of the tumor inside the jaw window (200). The variation in dwell time leads to dose modulation and dose distribution irregularities. FIG. 2C depicts a planned dose distribution (e.g., an IMRT planned dose profile) for a clinical target volume (CTV) and planning target volume (PTV) outlined in solid black lines. The ideal radiation delivery is one that delivers a homogenous dose distribution of a sufficient quantity within the boundaries of the target region. However, when the target region moves as the radiation is being delivered (e.g., due to patient breathing, patient platform movement through the treatment plane, and/or the therapeutic radiation source rotation about the patient), the delivered dose may deviate from the planned distribution. FIG. 2D depicts a simulated dose distribution resulting from radiation delivery to the target region as it moves in a fashion similar to the breathing motion described and depicted in FIGS. 2A and 2B. As shown there, there are regions of over-irradiation ("hot spots") (202) and regions of under-irradiation ("cold spots") (204).

Shuttle Mode

Figure 3A:
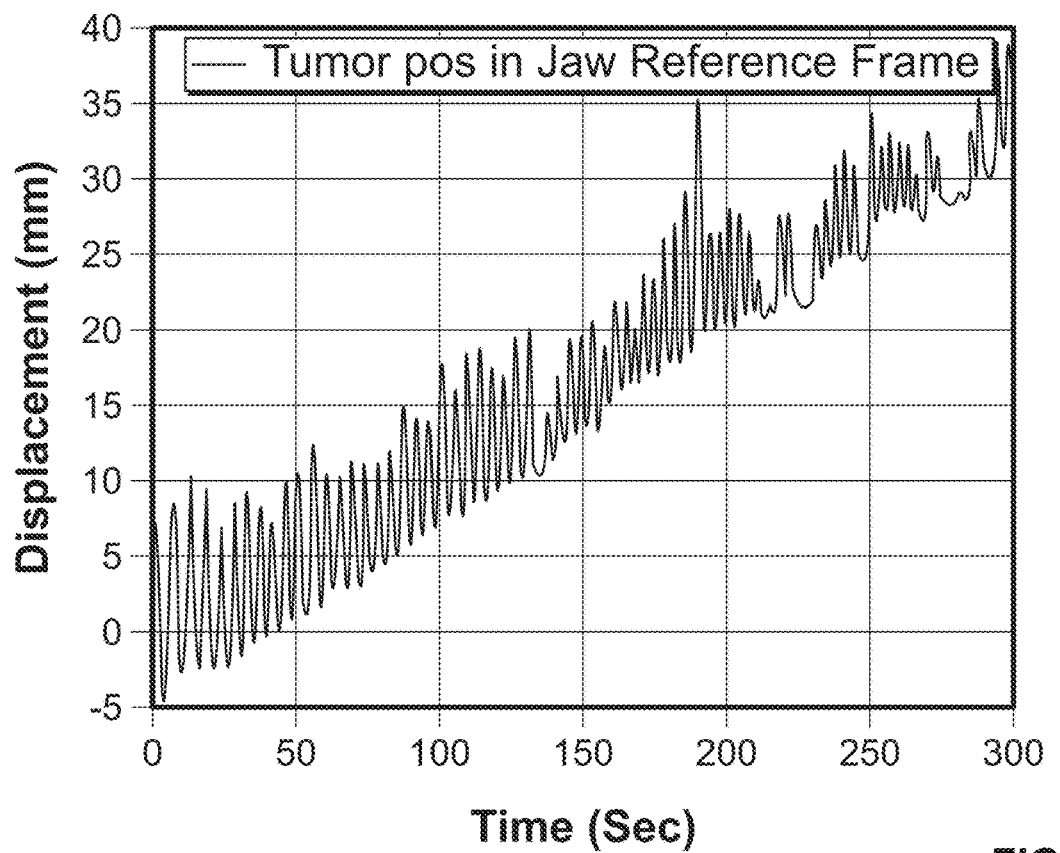
FIG. 3A depicts a plot that represents the motion of a target region during a treatment session.
Figure 3B:
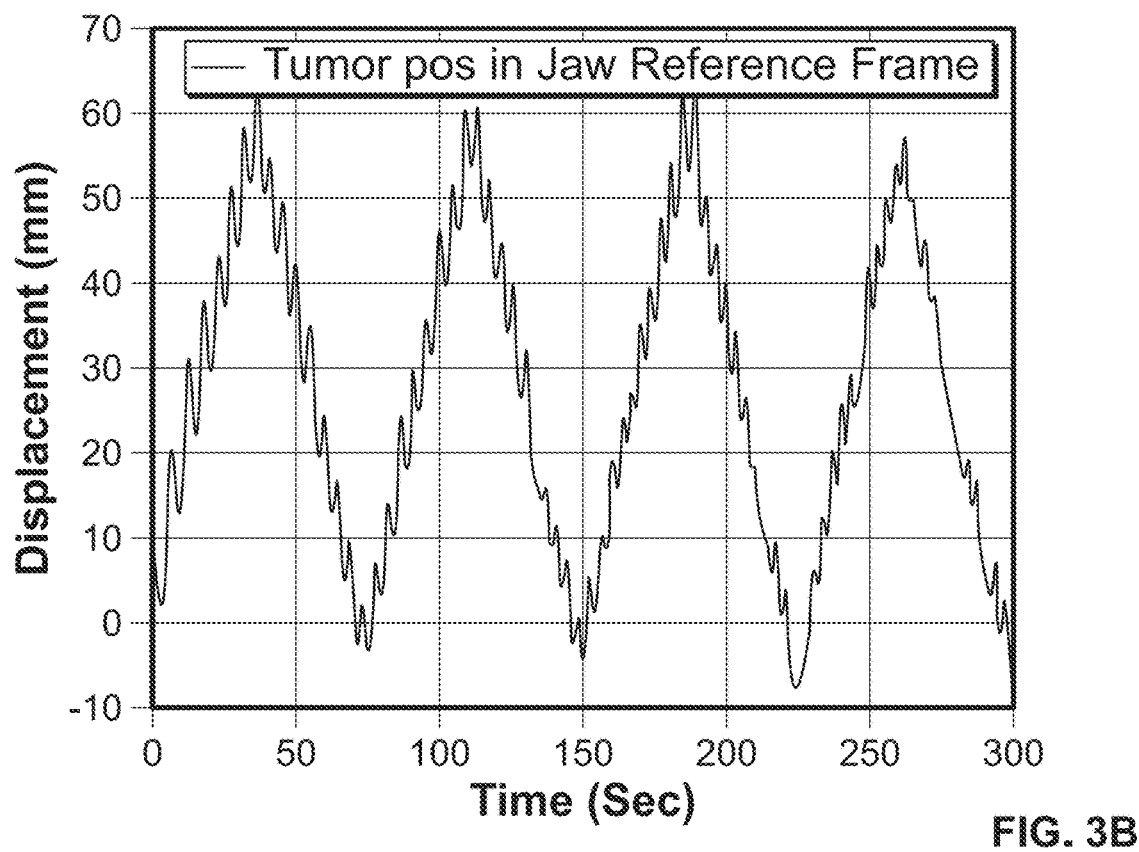
FIG. 3B depicts a plot that represents the motion of a target region during a treatment session in shuttle mode.
Figure 3D:
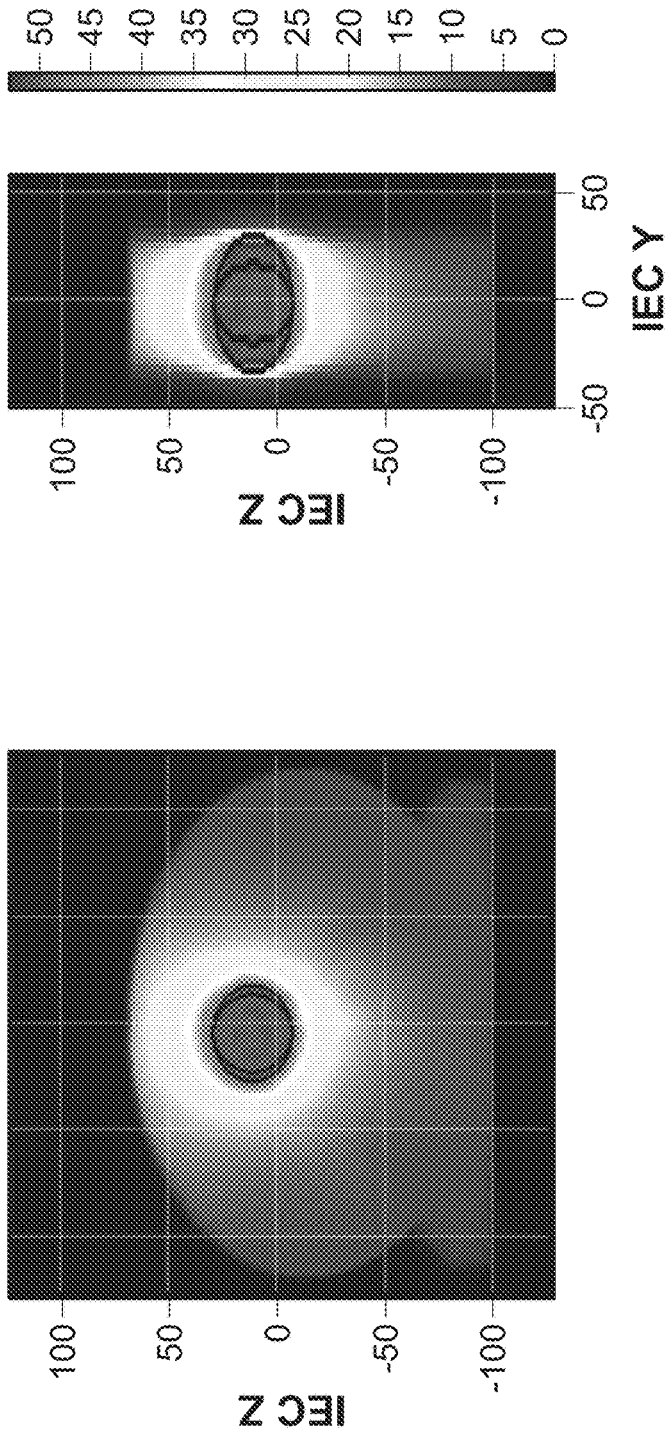
FIG. 3D depicts planned dose distribution plots.
Figure 3D:
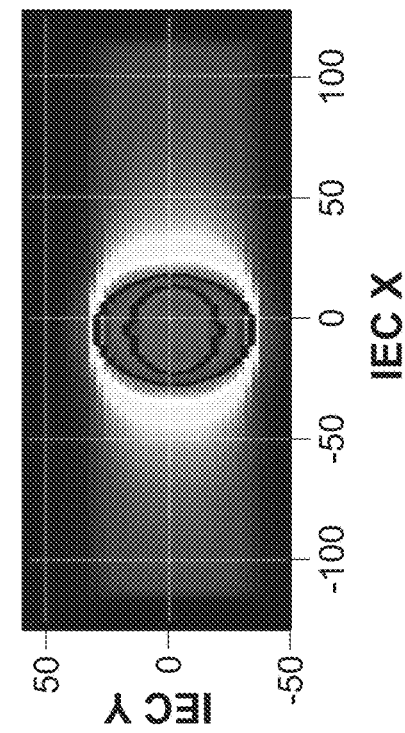
Figure 3E:
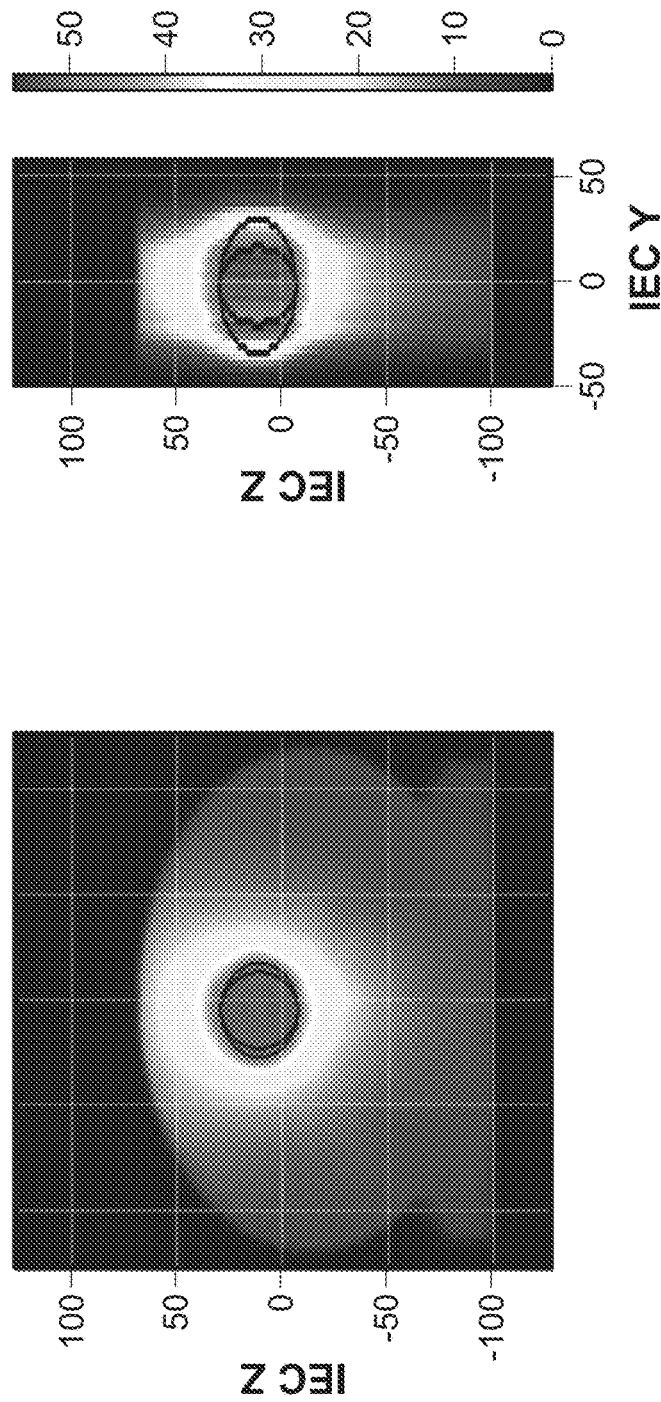
FIG. 3E depicts a delivered dose distribution plot for radiation delivered in shuttle mode.
Figure 3E:
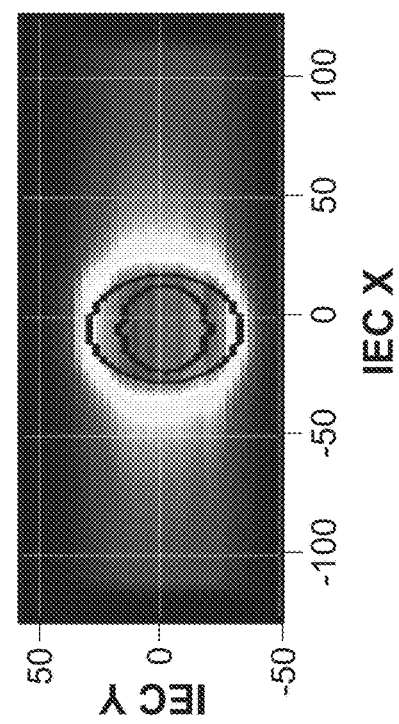

Methods that may help to address dose modulation due to patient or target region motion may comprise introducing a pre-determined and known motion to the radiation therapy system that has a frequency component that is uncorrelated with the breathing motion (e.g., having a frequency component that is outside of a frequency band around about 2 Hz). One variation of a method may comprise moving the patient platform (or couch) and/or the beam-shaping elements (such as the jaw) in a repeated or periodic fashion such that a patient target region(s) passes through the treatment plane more than once during a treatment session. For example, during a treatment session, the patient platform may be moved from a first pre-determined location to a second pre-determined location and back to the first pre-determined location, such that the target region(s) cross the treatment plane at least twice. Such repeated couch motion may be referred to as couch shuttling. where one couch shuttle cycle or pass includes moving from a first location to a second location while delivering radiation from the therapeutic radiation source. A successive shuttle pass may comprise moving the couch from the second location back to the first location while delivering radiation from the therapeutic radiation source. The couch may be moved continuously as radiation is delivered or may be stepped to a series of couch locations along the longitudinal axis (along IEC-Y) such that radiation is delivered only when the couch is stopped at these pre-determined locations (or beam stations). Alternatively or additionally, during a treatment session, a jaw may be moved from a first pre-determined jaw location to a second pre-determined jaw location (i.e., in a first jaw shuttle pass) and back to the first pre-determined jaw location (i.e., in a second jaw shuttle pass) such that the treatment plane defined at least in part by the jaw sweeps across the target region(s) at least twice in the two jaw passes. Such repeated jaw motion may be referred to as jaw shuttling, where one jaw shuttle cycle or pass includes moving from a first jaw location to a second jaw location while delivering radiation from the therapeutic radiation source. A successive jaw shuttle pass may comprise moving the jaw from the second jaw location back to the first jaw location while delivering radiation from the therapeutic radiation source. The jaw opening or aperture may be kept constant as the jaw shuttles. In other variations, the jaw opening or aperture may change while the jaw shuttles. Adjusting the speed of couch and/or jaw motion during couch and/or jaw shuttle mode may help to address dose modulation artifacts that arise from respiratory motion by sweeping the treatment plane over the target regions at a frequency that is uncorrelated with the frequency peaks of respiratory motion. For example, shuttling the couch and/or jaw on a timescale of about 70 seconds may help to mitigate artifacts that arise from breathing motions having a frequency peak or component on a timescale of about 5 seconds (e.g., about 0.2 Hz). FIGS. 3A and 3B are plots that represent target region motion over a 300 second treatment time interval or session, with one couch or jaw shuttle pass in FIG. 3A and eight couch shuttle passes in FIG. 3B. In shuttle mode, the couch or jaw comes back to the original position about every 70 seconds (though the couch or jaw speed may be adjusted such that the couch completes a roundtrip trajectory (i.e., a pair of passes) about every 80 seconds, about every 90 seconds, about every 100 seconds, etc.). As shown in the table in FIG. 3C, a treatment session that includes multiple shuttle cycles (e.g., 8 shuttle passes) results in a dose distribution that is closer to the planned dose than a treatment session that has a single shuttle cycle (e.g., 1 shuttle pass). The resultant dose distribution is depicted in FIG. 3E (while the planned dose distribution is reproduced in FIG. 3D). The CTV and PTV (which together may comprise a target region or radiation-firing zone) are outlined in solid black lines. As seen there, the dose distribution in FIG. 3E is more similar to the planned dose distribution than the dose distribution in FIG. 2D.

Although couch shuttle mode and jaw shuttle mode may be described separately, it should be understood that both the couch and the jaw may be shuttled simultaneously and/or sequentially during a treatment session (e.g., a first pass in jaw shuttle mode, a second pass in couch shuttle mode, etc.). A combination of motion between the couch and the jaws may be used to achieve the motion curve in FIG. 3B. This combined couch and jaw shuttle may be beneficial because it may be used to significantly reduce patient acceleration, particularly in cases with increased shuttle passes. For example, the "peaks" in FIG. 3B (where the shuttling changes direction), the shuttling effect could be attained by jaw shuttling (such that most acceleration is at the jaws and the acceleration at the couch is almost zero). These methods may be used with radiation therapy systems that are configured for continuous couch motion and/or step-and-shoot couch motion.

Couch Shuttle

Figure 4:
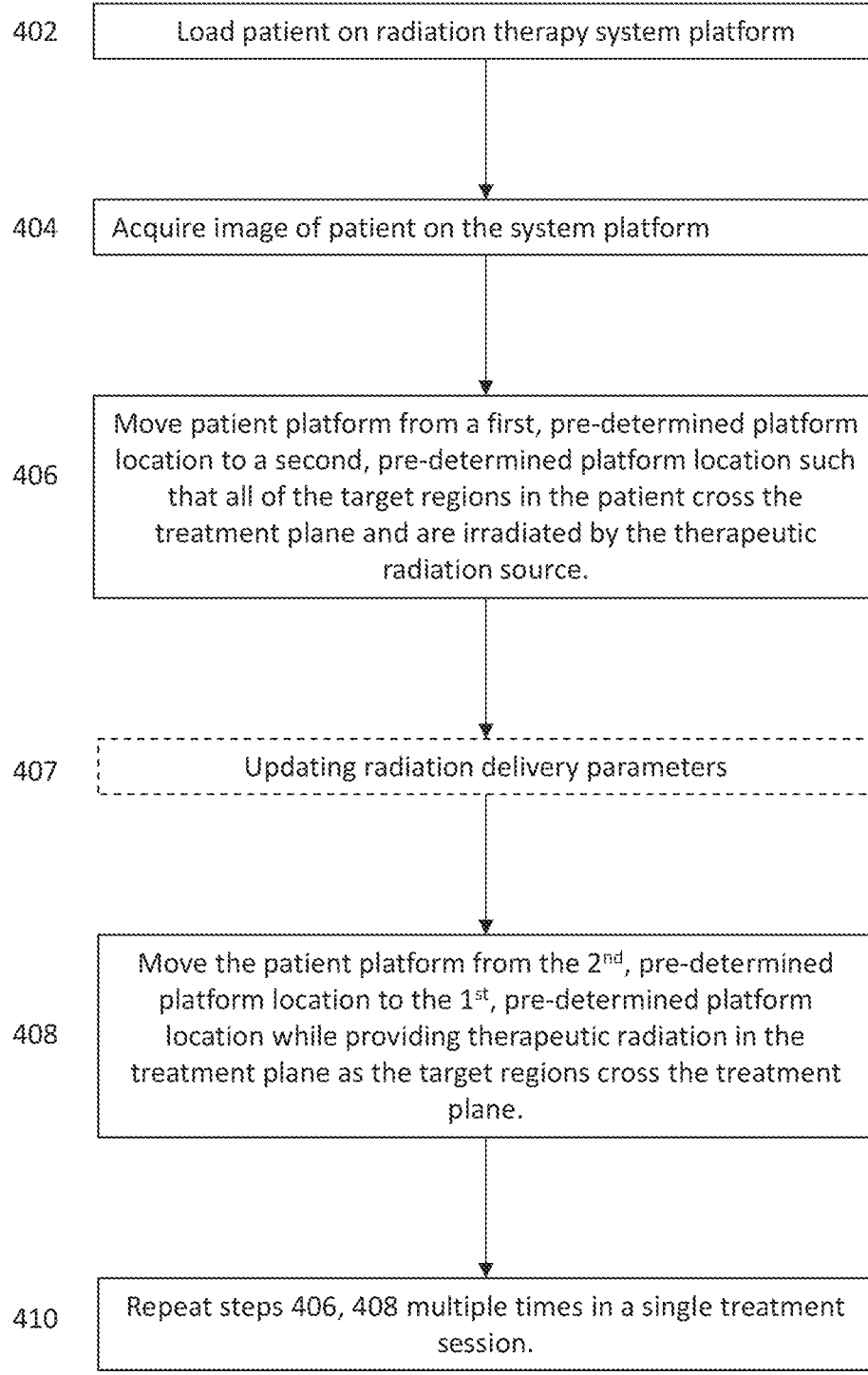
FIG. 4 depicts a flowchart representation of one variation of a method for patient platform or couch shuttle mode.

One variation of a method for couch shuttling is represented by the flow chart diagram in FIG. 4. The method (400) may optionally comprise loading (402) a patient on a radiation therapy system platform and acquiring (404) an image of the patient. The acquired image may be used to register the position and location of the patient with the coordinate system of the radiation therapy system and/or normalize the treatment plan before beam-on. The method (400) may comprise moving (406) the patient platform from a first, pre-determined platform location to a second, pre-determined platform location such that all of the target regions in the patient cross the treatment plane and are irradiated by the therapeutic radiation source. In some variations, the therapeutic radiation source, beam-shaping module (e.g., jaws and dynamic binary MLC), and gantry may apply a fluence to the patient based on detected LOR data convolved or multiplied with a treatment plan RFM. Optionally, the method (400) may comprise updating (407) radiation delivery parameters based on acquired PET data and/or MV detector data. For example, updating radiation delivery parameters may include normalizing the radiation fluence derived by multiplying the acquired PET data with the RFM, recalculating the RFM based on delivered dose or fluence calculations, and/or updating jaw, MLC, couch and/or gantry instructions and/or adjusting or modifying the radiation fluence for delivery using one or more scaling factors such as one or more normalization factors, one or more dampening factors, etc. The emitted fluence and/or delivered dose (e.g., of a single shuttle pass and/or cumulatively) may optionally be calculated. The method (400) may comprise moving (408) the patient platform from the second pre-determined platform location to the first, pre-determined platform location while providing therapeutic radiation in the treatment plane as the target regions cross the treatment plane. The method (400) may comprise repeating (410) steps (406) and (408), with or without optional step (407), any number of times (e.g., once or more times). In some variations, steps (406) and (408) may be repeated an even number of shuttle cycles or times (e.g., 2, 4, 6, 8, 10 times) during the treatment session.

Jaw Shuttle

Figure 5:
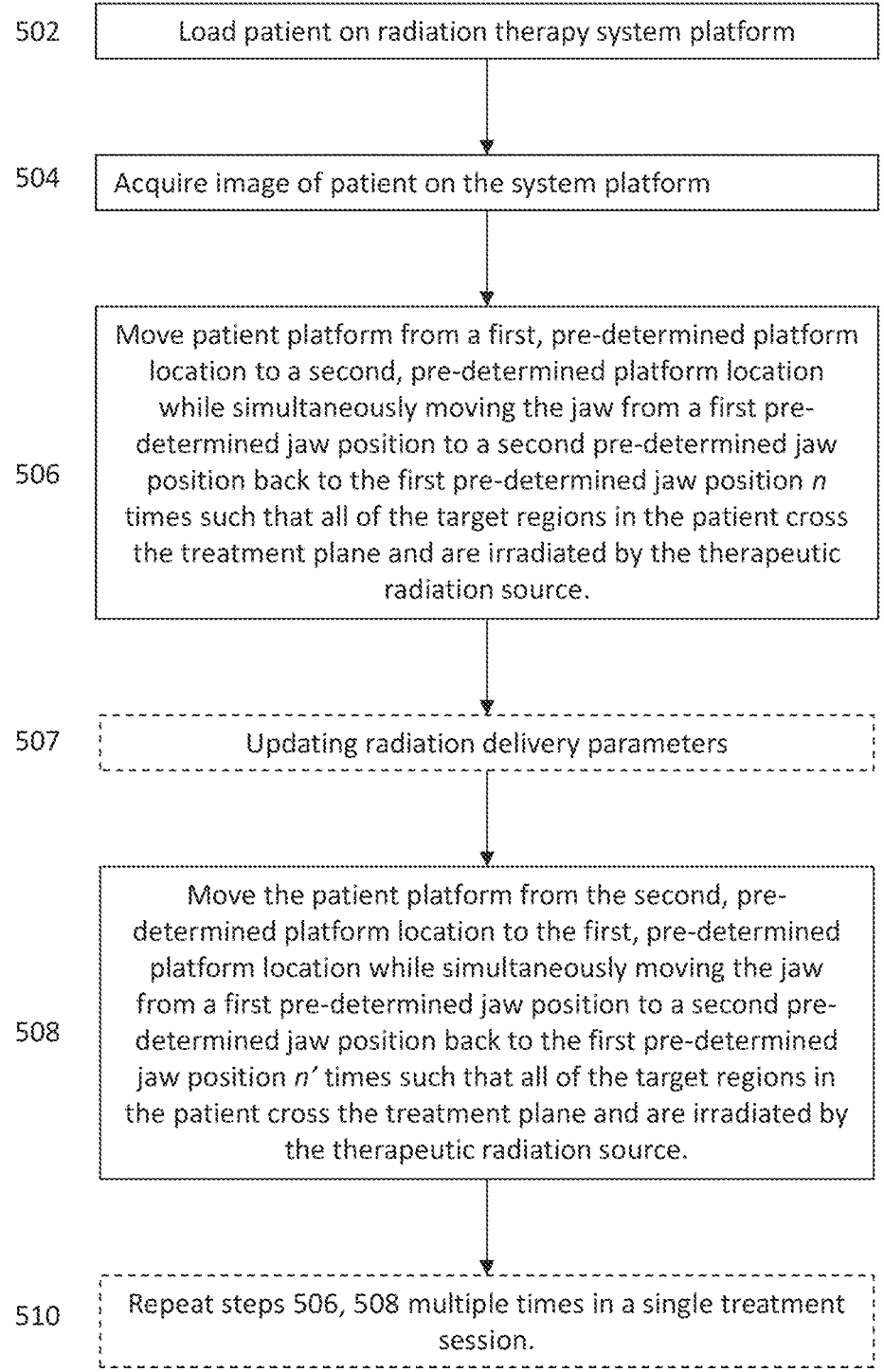
FIG. 5 depicts a flowchart representation of one variation of a method for jaw shuttle mode.

One variation of a method for jaw shuttling is represented by the flow chart diagram in FIG. 5. The method (500) may optionally comprise loading (502) a patient on a radiation therapy system platform and acquiring (504) an image of the patient. The acquired image may be used to register the position and location of the patient with the coordinate system of the radiation therapy system and/or normalize the treatment plan before beam-on. The method (500) may comprise moving (506) the patient platform from a first, pre-determined platform location to a second, pre-determined platform location while simultaneously moving the jaw from a first pre-determined jaw position to a second pre-determined jaw position back to the first pre-determined jaw position n times such that all of the target regions in the patient cross the treatment plane and are irradiated by the therapeutic radiation source. n may be any number (e.g., 1, 2, 3, 4, 5, 7, 9, 11, etc.), and in some variations, n may be an even number, for example, 2, 4, 6, 8, 10, etc., and the rate or speed at which the jaw moves may be from about 0.25 cm/s to about 2 cm/s, e.g., about 0.5 cm/s, about 1 cm/s. In some variations, the therapeutic radiation source, beam-shaping module (e.g., jaws and dynamic binary MLC), and gantry may apply a fluence to the patient based on detected LOR data convolved or multiplied with a treatment plan RFM. While the jaw is shuttling between the first pre-determined jaw position and the second pre-determined jaw position, the configuration of the MLC may change (i.e., the leaves may transition between the open and closed states) in accordance with the fluence map derived from multiplying or convolving the RFM with LOR data (e.g., based on instructions from segmenting the fluence map). Optionally, the method (500) may comprise updating (507) radiation delivery parameters based on acquired PET data and/or MV detector data. For example, updating radiation delivery parameters may include normalization the RFM, recalculating the RFM based on delivered dose or fluence calculations, and/or updating jaw, MLC, couch and/or gantry instructions, and/or adjusting or modifying the radiation fluence for delivery using one or more scaling factors such as one or more normalization factors, one or more dampening factors, etc. The emitted fluence and/or delivered dose (e.g., of a single shuttle pass and/or cumulatively) may optionally be calculated. The method (500) may comprise moving (508) the patient platform from the second, pre-determined platform location to the first, pre-determined platform location while simultaneously moving the jaw from a first pre-determined jaw position to a second pre-determined jaw position back to the first pre-determined jaw position n' times such that all of the target regions in the patient cross the treatment plane and are irradiated by the therapeutic radiation source. n' may be any number (e.g., n'=1, 2, 3, 4, 5, 7, 9, 11, etc.) and in some variations, n' may be an even number, for example, 2, 4, 6, 8, 10, etc. and may or may not be the same as n. The method (500) may optionally comprise repeating (510) steps (506) and (508), with or without optional step (507), an even number of shuttle cycles or times (e.g., 2, 4, 6, 8, 10 times) in the treatment session. Including the optional step (510) combines both couch shuttling and jaw shuttling. As described previously, the jaw may be moved at a rate from about 0.25 cm/s to about 2 cm/s, e.g., about 0.5 cm/s, about 1 cm/s, and the distance between the first and second pre-determined jaw positions may be from about 1 cm to about 4 cm, e.g., about 1 cm, about 2 cm. The frequency of jaw shuttling may be about 4 to about 5 times the dominant frequency component of breathing motion.

Delivery and Interplay Artifact Mitigation

As described briefly above, radiation delivery parameters may optionally be updated during the treatment session. Updating delivery parameters may help to mitigate dose modulation artifacts due to patient motion. In some variations, methods may comprise calculating the fluence delivered to the patient during a shuttle pass (couch and/or jaw shuttle pass), comparing the delivered fluence with the treatment plan fluence and calculating a fluence difference, and updating the RFM of a treatment plan to deliver the fluence difference at a subsequent shuttle pass. The fluence calculation may be a mean fluence over one or more target regions. The fluence difference can be calculated/estimated in the static patient frame-of-reference, and delivered in one or more subsequent passes without requiring any further imaging data (e.g., without any PET imaging data, CT imaging data, or MV detector data). Alternatively, it can be calculated in the tumor point-of-view (POV) frame-of-reference. In some variations, the methods may comprise calculating cumulative delivered fluence (and not just the fluence delivered in a single shuttle pass) across all the previous shuttle passes in the treatment session. Alternatively or additionally, a method may comprise calculating the dose delivered to the patient during a shuttle pass (couch and/or jaw shuttle pass), comparing the delivered dose with the treatment plan dose and calculating a dose difference, and updating the RFM of a treatment plan to deliver the dose difference at a subsequent shuttle pass. The dose calculations may be a mean dose over one or more target regions. These methods may also help compensate or correct for dose modulation artifacts due to radiation therapy system limitations/constraints. System limitations/constraints may include noise resulting from a dynamic binary MLC configuration or radiation beam shape that does not exactly match filtered partial images (e.g., fluence map calculated based on LOR data multiplied with the RFM), noise in the imaging system (c.g., PET, CT, MRI imaging systems), etc. Updating the RFM and/or delivery parameters (e.g., delivery fluence map, segmented machine instructions, etc.) during a treatment session based on real-time delivery values/metrics (e.g., fluence, dose, imaging data such as PET LORs) may facilitate continuous artifact correction during the session. Regular updates to the RFM and/or delivery parameters may help tune each successive radiation delivery segment (or shuttle pass) such that the cumulative delivered fluence or dose converges towards the planned/prescribed fluence or dose delivery distribution.

Figure 6:
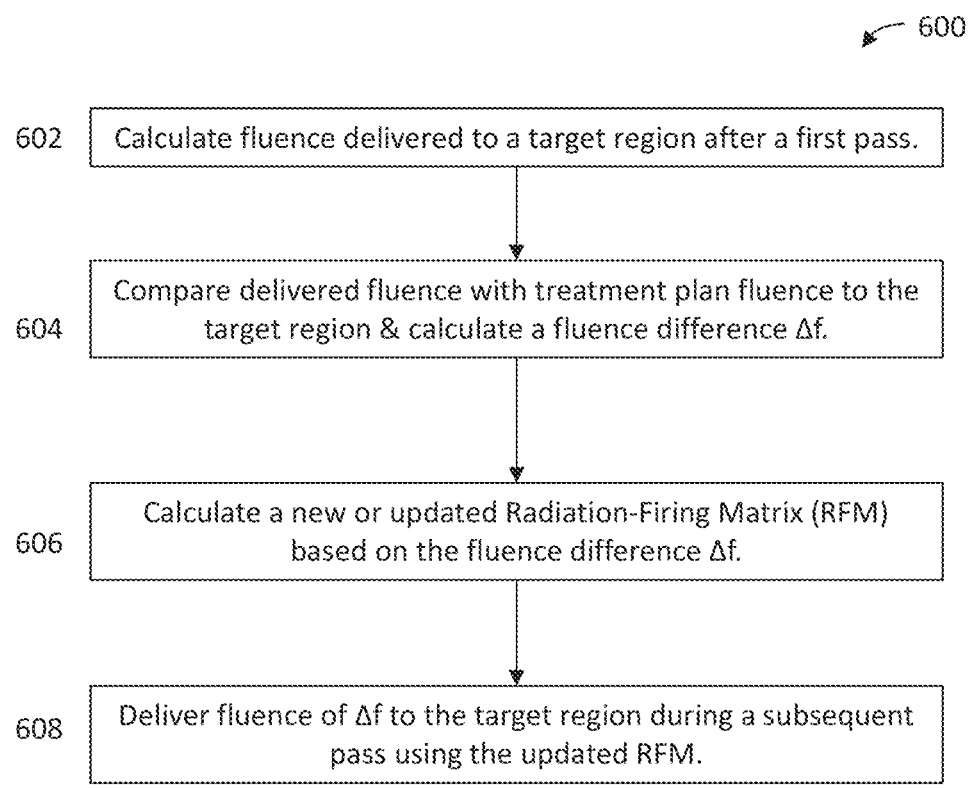
FIG. 6 depicts a flowchart representation of one variation of a method for updating a radiation-firing matrix (RFM) during a treatment session.

FIG. 6 depicts a flowchart representation of one method for updating a RFM during a treatment session. Method (600) may comprise calculating (602) the fluence delivered to a target region after a first shuttle pass. The shuttle pass may be jaw shuttling and/or couch shuttling. The delivered fluence may be calculated based on therapeutic radiation source dose chamber measurements and/or radiation beam pulse parameters (e.g., frequency, duration, duty cycle, number of pulses, etc.), and/or MLC leaf configurations, and/or jaw configurations. Optionally, the delivered fluence may be calculated using MV detector data. The method (600) may comprise comparing (604) the delivered fluence to the target region (e.g., mean delivered fluence over the target region) with treatment plan fluence to the target region (e.g., mean planned fluence over the target region) and calculating a fluence difference $\Delta f$ (e.g., mean fluence difference over the target region), and calculating (606) a new or updated radiation-firing matrix (RFM) based on the fluence difference $\Delta f$. After updating the RFM, the radiation therapy system may deliver (608) the fluence difference $\Delta f$ to the target region during a subsequent shuttle pass using the updated RFM. For example, in biology-guided radiation therapy, the fluence difference $\Delta f$ may be delivered by multiplying imaging data acquired during the treatment session (e.g., partial images) with the updated RFM. In emission-guided radiation therapy (a type of biology-guided radiation therapy), the updated RFM may be multiplied with one or more detected LORs to generate a delivery fluence map. The delivery fluence map may then be segmented into machine instructions (e.g., MLC, linac, gantry, patient platform/couch, and/or jaw instructions) that emit radiation to the patient according to the fluence map. The method (600) may also be used to update the RFM over multiple target regions. For example, the fluence (e.g., mean fluence) delivered to multiple target regions may be calculated, compared to the planned fluence (e.g., mean planned fluence) of each of the multiple target regions to calculate a difference for each target region ($\Delta f_{TRi}$ for i target regions), and the fluence difference across all target regions may be averaged together (or otherwise normalized) to update the RFM. In some variations, the RFM may be updated or optimized such that the fluence or dose delivery metrics are met for the greatest number of target regions. The method (600) may also be performed using dose calculations instead of fluence calculations. In emission-guided radiation therapy, the method (600) may be performed using PET or LOR data (e.g. average PET intensity over a target region).

Pipelined Normalization

In typical radiation delivery, corrections or adjustments to the treatment plan and/or radiation delivery parameters are applied once before treatment commences. That is, corrections or adjustments based on a treatment session pre-scan image acquired are calculated once and applied to the treatment plan and/or radiation delivery parameters once before beam-on. However, because this update occurs only once at the beginning of a treatment session, any dose modulation artifacts may not be corrected. With the couch and/or jaw shuttle modes described herein, corrections or adjustments to the treatment plan and/or radiation delivery parameters may be calculated and applied between shuttle passes. On each pass, acquired data from the previous pass (e.g., PET imaging data or LORs, MV detector data, etc.) may be used to estimate the amount of fluence or dose that has been delivered to the target region(s). That is, the previous imaging data may be used to predict the future dose in the next pass. The next shuttle pass can be corrected by the radiation fluence or dose delivered in the treatment session up to that point by adjusting the RFM, for example, and/or scaling or shifting the emitted fluence for a current shuttle pass using a normalization factor that may be dynamically updated based on the fluence and/or dose delivered in the previous shuttle pass(es). This dynamic or pipelined normalization may help to correct for errors in image noise or changes that are detected during the delivery, including changes in the attenuation artifact from moving structures that may be outside the target region(s). In some variations where multiple tumor regions are to be irradiation, a normalization factor may be calculated for each region, where each region-specific normalization factor may incorporate factors and variations specific to that particular tumor region. Each normalization factor for each region may be calculated using any of the methods described herein. Alternatively, there may be a single, global normalization factor for all tumor regions.

Figure 7:
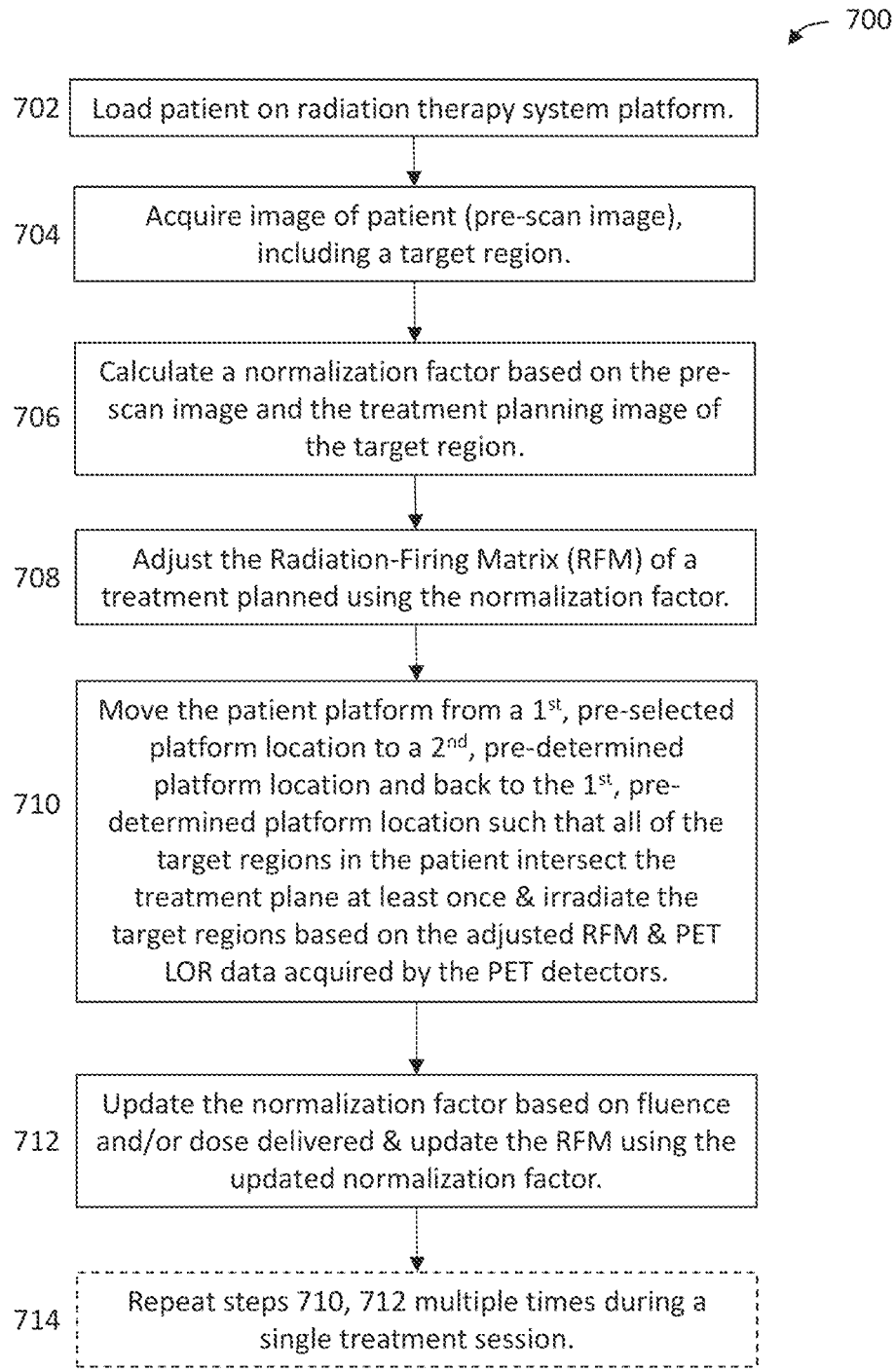
FIG. 7 depicts a flowchart representation of one variation of a method for dynamically updating a RFM during an emission-guided radiation therapy session.

An illustrative method for dynamically updating a RFM during an emission-guided radiation therapy session is depicted in FIG. 7. Although these methods (as well as the other methods included herein) are described in the context of delivering radiation based on PET image (e.g., LOR) data, it should be understood that these methods may be used for any biology-guided radiation therapy imaging modality, including but not limited to, radiation delivery based on CT partial image data, radiation delivery based on MRI partial image data. A method (700) may optionally comprise loading (702) a patient on a radiation therapy system patient platform or couch and acquiring (704) an image of the patient, including one or more target regions in the patient. In emission-guided radiation therapy, a PET tracer (e.g., one that accumulates at tumor regions) may be introduced into the patient, and the pre-scan may be a PET image.

The method (700) may comprise calculating (706) a normalization factor (NF) based on the pre-scan image and the image used to generate the treatment plan. The NF may be calculated by calculating the mean PET imaging signal of the pre-scan within a target region (i.e., treatment field or radiation-firing zone) and calculating the mean PET signal of a treatment planning image within the same target region (i.e., treatment field or radiation-firing zone). The NF may be a ratio of the mean planning PET imaging signal and the mean pre-scan PET imaging signal.

Optionally, in some variations, the PET pre-scan image may be used to predict the dose or fluence that will be delivered in a shuttle pass that immediately follows the pre-scan. For example, the pre-scan image can be used to predict or estimate the real-time fluence or dose that will be delivered will meet certain delivery metrics. The pre-scan image can be normalized by the NF. The pre-scan image can now be used to estimate the dose of radiation delivery and may be significantly less sensitive to image noise of the PET image. The normalization factor can also be used to normalize the mean treatment plan fluence or mean treatment plan radiation dose to the target region.

Method (700) may comprise adjusting (708) the treatment plan RFM based on the calculated NF. Adjusting the RFM by the NF may comprise modifying the RFM using any linear operation or transformation based on the NF. Examples of linear operations may including multiplying, convolving, and/or scaling the RFM by the NF. In some variations, it may also include adding or subtracting a constant based on the NF to the RFM. Method (700) may then comprise moving (710) the patient platform from a first, pre-determined platform location to a second, pre-determined platform location (i.e., a first couch shuttle pass) and back to the first, pre-determined platform location (i.e., a second couch shuttle pass) such that all of the target regions in the patient intersect the treatment plane at least once (e.g., one or more times, two or more times, etc.). While moving the patient platform, the target regions may be irradiated based on the adjusted RFM and PET LOR data acquired by the PET detectors. When the patient platform has returned to the first pre-determined platform location, the NF may be updated (712) based on the fluence and/or dose delivered during the shuttle pass. In some variations, the NF may be updated based on the PET LOR data acquired during the shuttle pass. For example, the updated NF may be calculated by taking the ratio of the planned fluence (e.g., mean planned fluence) to a target region (e.g., treatment field, radiation-firing zone) to the actual delivered fluence (e.g., mean delivered fluence) to that target region. Alternatively or additionally, the updated NF may be calculated by taking the ratio of the planned dose (e.g., mean planned dose) to a target region (c.g., treatment field, radiation-firing zone) to the actual delivered dose (e.g., mean delivered dose) to that target region, where the delivered dose is calculated based on the delivered fluence and the pre-scan image or treatment planning image. Updating the NF based on fluence calculations may help radiation delivery to meet fluence-based metrics, such as total conservation of monitor units, while updating the NF based on dose calculations may help radiation delivery to meet dose-based metrics (e.g., D95 coverage, max OAR dose). In emission-guided radiation therapy, the NF may be updated based on PET intensity over a target region (e.g., ratio of the mean PET intensity of a target region based on a PET planning or pre-scan image to the mean PET intensity of the target region based on LOR data acquired during the treatment session). The RFM may be updated using any linear operation or transformation based on the NF, as described above. Optionally, method (700) may comprise repeating (714) steps (710), (712) any number of times during a treatment session, and in some variations, an even number of times during a treatment session, and may stop when the delivered fluence or dose converges to the planned fluence or dose.

While method (700) provides an example of dynamic normalization using patient platform or couch shuttling, it should be understood that the method (700) may also be used in jaw shuttling mode, where the NF and RFM are updated after each jaw shuttle pass. In jaw shuttle mode, it may be that the patient platform completes only one pass during the treatment session, since the jaw has completed multiple shuttle passes over the single platform shuttle pass. Alternatively or additionally, method (700) may be used in a combined couch and jaw shuttling mode.

In some variations, a method for radiation delivery may comprise adjusting the radiation fluence or dose to be emitted or delivered using one or more adjustment factors such as one or more of normalization factors, dampening factors, weighting factors, and the like. The radiation fluence or dose to be emitted or delivered during a particular shuttle pass (e.g., couch/platform shuttle and/or jaw shuttle) may be scaled and/or shifted by the adjustment factor(s). In some variations, the adjustment factor(s) may be adjusted and/or updated for each shuttle pass so that the adjustment factor(s) may reflect the up-to-date state of the patient (e.g., using imaging data, and/or images, and/or other physiological data) as well as the radiation delivered during the treatment session. For example, the adjustment factor(s) may be updated or tuned based on the radiation fluence emitted or dose delivered during the previous shuttle pass and the amount of fluence or dose as prescribed by the treatment plan. In one variation, the fluence (or dose) to be delivered in a shuttle pass may be scaled by a normalization factor (and/or optionally, a dampening factor) that may be calculated based at least in part on the radiation delivered in the previous shuttle pass and imaging data acquired during the previous shuttle pass (and/or any other imaging data acquired during the treatment session). Scaling the radiation fluence or dose by a normalization factor that is adjusted for each shuttle pass may facilitate the convergence of the cumulative radiation delivered toward the planned radiation fluence or dose (i.e., radiation fluence or dose specified by the treatment plan). In the case of emission-guided radiation therapy where the radiation fluence or dose applied to a patient is calculated based on imaging data (e.g., PET imaging data) acquired during the treatment session, scaling or otherwise adjusting the radiation fluence or dose with a normalization factor that accounts for the cumulative fluence or dose that has already been delivered during the session and the difference between the quantity of delivered radiation and the planned quantity of radiation (e.g., as specified by a treatment plan and/or clinician) may help compensate for any radiation delivery errors, fluctuations and/or unexpected or unintended variations due to tumor motion, patient motion, and/or variable tracer uptake, and the like. While the methods included herein are described in the context of emission-guided or biologically-guided radiotherapy using PET tracers and positron emission data, it should be understand that these methods may also be used in any radiotherapy modality that applies radiation using data acquired in real-time during a treatment session. In addition, the methods described herein for the calculation of one or more normalization factors may use radiation fluence, the methods may alternatively or additionally use radiation dose to calculate normalization factors. A radiation dose value or profile may be derived from a fluence value or profile using a dose calculation matrix A, where matrix A may be a linear operator that maps fluence to dose in the image space. Specific reference to a radiation fluence or dose in any of the methods described herein may refer more generally to a quantity of radiation that is emitted or delivered to a target region.

Optionally, for any of the methods described herein, the treatment time and/or number of couch shuttle passes N may be selected before radiation delivery (though these methods may also be adapted for use with jaw shuttling). The treatment times and/or number of shuttle passes N may be determined or selected, for example, during treatment planning, before a patient is set up for a treatment session, or after the patient is set up for treatment but before the treatment beam is activated. Optionally, a dampening factor α (from which a normalized dampening factor β may be derived) may be selected according to a desired radiation delivery rate across multiple shuttle passes. Given the number of shuttle passes N and a dampening factor α, normalized dampening factor β may be derived as follows:

$$\beta_i = \frac{\alpha^{i-1}}{\sum_{j=1}^{N} \alpha^{j-1}}$$

For example, in some variations, a dampening factor a may be selected such that a larger proportion of the prescribed or planned radiation fluence or dose is delivered in the earlier shuttle passes than in the latter shuttle passes (i.e., the radiation fluence emitted in a first pass is greater than the radiation fluence emitted in the last pass). In such manner, the earlier shuttle passes function to deliver the majority of the planned radiation dose, while the later shuttle passes function to deliver fluence corrections or adjustments to compensate for any errors, artifacts, and/or motion (e.g., interplay artifacts, patient or tumor motion) that may have occurred during a treatment session. In any of the methods included herein, the dampening factor a may be from 0 to about 1, e.g., about 0.5. 0.6, 0.7, 0.75, 0.77, 0.8, 0.83, 0.85, 0.90, 0.91, 0.97, 1, etc. In addition to specifying the number of shuttle passes N, the treatment session duration time may also be specified. In some variations, the treatment session duration may be held constant and the time spent per shuttle pass may be adjusted according to the number of shuttle passes. That is, as the number of shuttle passes increases, the time per shuttle pass may decrease, and the dwell time of the target region in the therapeutic radiation beam plane for a particular shuttle pass may be reduced. The cumulative dwell time across the entire treatment session (e.g., across all N shuttle passes) may remain approximately constant regardless of the number of shuttle passes, since the dwell time is reduced accordingly. In the examples described herein, the number of shuttle passes N may be four and the dampening factor α may be 0.83 (i.e., 1/1.2), but N and α (and subsequently, β) may vary as desired. For example, in a treatment session where N=4 and α=(1/1.2) or 0.8333, the normalized dampening factor for each of the four passes may be $\beta_1$=0.33, $\beta_2$=0.28, $\beta_3$=0.23, $\beta_4$=0.19. While a normalization factor and one or more dampening factors (α, β) may be used to adjust the radiation fluence emitted to a target region during a shuttle pass, the radiation fluence may be adjusted with only a normalization factor, a plurality of normalization factors, a single dampening factor, and/or any other additional factors that tune the emitted radiation to reflect the patient and/or system conditions during the treatment session.

FIG. 8A depicts one variation of a method where the radiation applied during a treatment session is adjusted for each shuttle pass. As described previously, a shuttle pass may comprise moving a patient platform or couch from a first location to a second location such that the one or more tumor regions in a patient pass through a therapeutic radiation beam plane once. The couch may be moved continuously as radiation is delivered (e.g., helical radiation delivery), or may be moved in steps such that radiation is delivered only when the couch is stopped at a predetermined couch location or step (e.g., beam station delivery, therapeutic radiation beam is stopped while the couch is moving and on when the couch is stopped). While the methods described below are in the context of couch shuttling, it should be understood that similar methods may be adapted for use in jaw shuttling. Method (800) may comprise moving (802) a patient (i.e., by moving a patient platform) from a first location to a second location such that the patient passes through a radiation treatment plane while acquiring imaging data, and applying (804) a first quantity of radiation as the patient passes through the radiation beam plane. This may be referred to as a first shuttle pass, and the first quantity of radiation may be determined at least in part based on the treatment plan, the imaging data acquired during the first pass (e.g., full images such as a pre-scan image of the patient $X_{prescan}$ acquired at the start of a treatment session, and/or partial images, such as one or more LORs or positron annihilation emission paths), along with one or more adjustment factors (e.g., a first normalization factor and/or a first dampening factor). Method (800) may then comprise moving (806) the patient (i.e., by moving the patient platform) from the second location to the first location such that the patient passes through a radiation treatment plane while acquiring imaging data, and applying (808) a second quantity of radiation as the patient passes through the radiation beam plane, where the second quantity of radiation is different from the first quantity of radiation. This may be referred to as a second shuttle pass, and the second quantity of radiation may be determined at least in part based on the treatment plan, the imaging data acquired during the second pass (e.g., full images such as a pre-scan image of the patient $X_{prescan}$ acquired at the start of a treatment session, and/or partial images, such as one or more LORs or positron annihilation emission paths), along with one or more adjustment factors (e.g., a second normalization factor and/or a second dampening factor) as well as the quantity of radiation that was delivered in the previous (first) pass. The second normalization factor and/or second dampening factor may be different from the first normalization factor and/or first dampening factor. The steps (802-804) and/or (806-808) may be repeated as many times as desired or as specified (e.g., up to N shuttle passes). The number of shuttle passes N may be odd or even, and therapeutic radiation may be applied as the patient is alternately shuttled between the first and second locations. In some variations, the distance between the first location and the second location may span a substantial length of the patient's body and may be, for example, at least as long as the distance between the target regions that are furthest from each other (i.e., along the longitudinal, IEC-Y axis) or at least as long as the largest dimension of a single target region (i.e., the length of a target region along the longitudinal, IEC-Y axis).

In some variations where radiation delivered to target regions may be at least partially determined by imaging data (and/or any patient or system data) acquired during the treatment session, the fluence emitted by the radiation therapy system may be adjusted to help ensure that cumulatively, the delivered dose converges to the prescribed dose (i.e., dose specified by the treatment plan or $D_{plan}$. The adjustment factor for a particular shuttle pass may be derived based on the acquired imaging data (and/or patient or system data), the amount of radiation that has been delivered already, treatment plan parameters, and/or any other filters or scaling or weighting factors, and the adjustment factor may be calculated and/or updated for each shuttle pass.

Figure 8B:
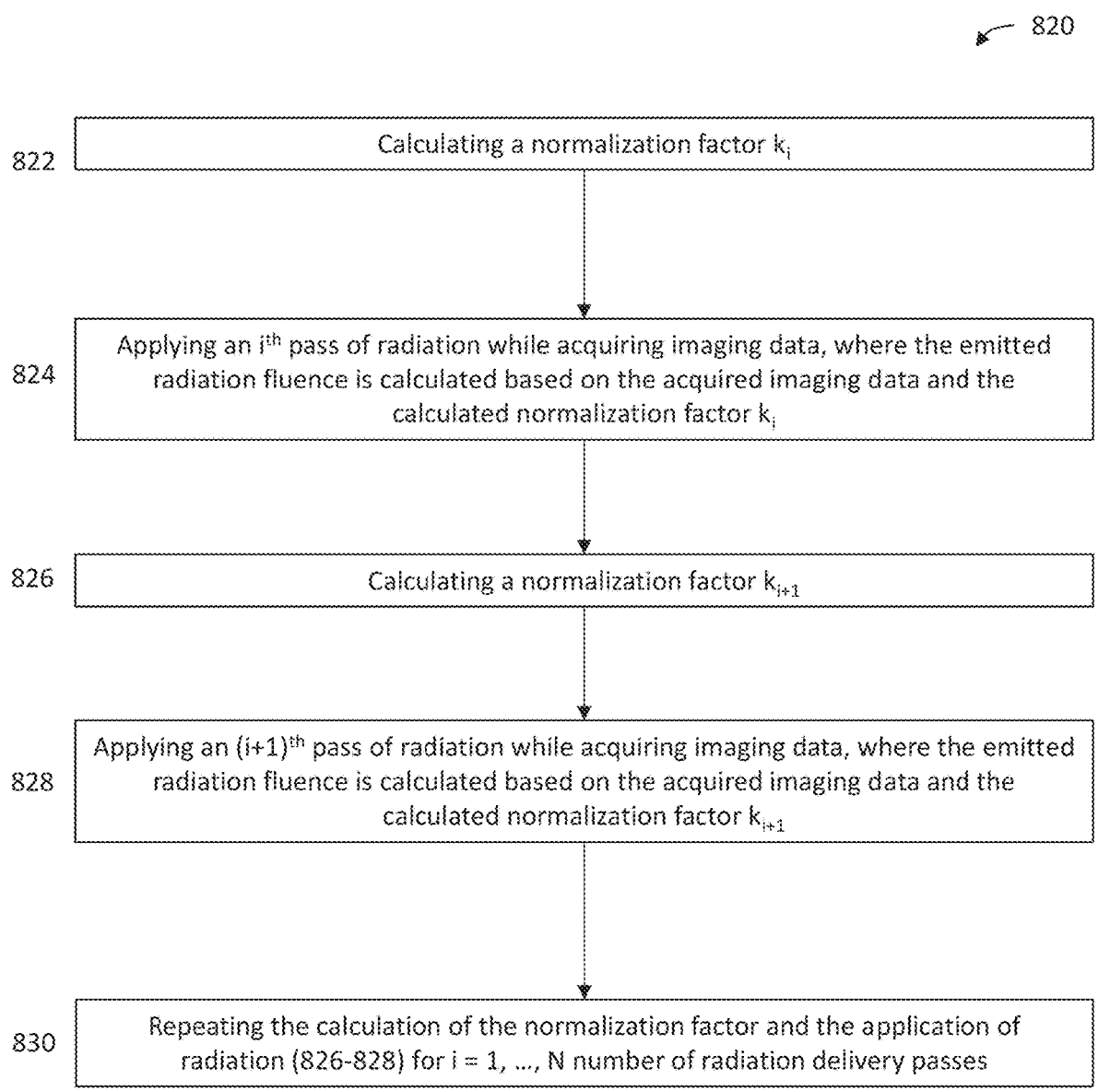
FIG. 8B depicts one variation of a method where radiation delivery is modified according to a normalization factor.

FIG. 8B depicts one variation of a method where the radiation applied during a shuttle pass is modified or adjusted according to a normalization factor that is calculated before the shuttle pass begins and the normalization factor is updated for each shuttle pass (i.e., pipelined normalization). The method (820) may comprise calculating (822) a normalization factor $k_i$, applying (824) an $i^{th}$ pass of radiation while acquiring imaging data, where the emitted radiation fluence is calculated based on the acquired imaging data and the calculated normalization factor $k_i$, calculating (826) a normalization factor $k_{i+1}$, applying (828) an $i^{th}$ pass of radiation while acquiring imaging data, where the emitted radiation fluence is calculated based on the acquired imaging data and the calculated normalization factor $k_{i+1}$, and repeating (830) the calculation of the normalization factor and the application of radiation (826-828) for i=1, . . . , N number of radiation delivery passes. In one variation, the normalization factor $k_{i+1}$ may be calculated by taking the difference between the cumulative planned radiation fluence or dose $D_{plan}$ and the radiation fluence that has been delivered so far (i.e., in all previous shuttle passes) and normalizing (e.g., dividing) the difference between the planned and delivered fluence with predicted cumulative fluence (which may not be segmented into discrete fluence values or levels) that would be applied to the target region if each of the future shuttle passes delivered the same amount of radiation as was delivered in the previous shuttle pass. The radiation cumulatively emitted during the previous shuttle passes may be calculated based on radiation therapy system commands and configurations (e.g., pulse parameters from the therapeutic radiation source, MLC configurations, gantry rotations, etc.) and/or sensor data (e.g., MV detector data, dose chamber data, position sensor data from the MLC, couch, gantry, etc.), and/or imaging data (e.g., PET data, CT data, MRI data, etc.). In emission-guided radiation therapy (e.g., biologically-guided radiation therapy) where imaging data comprises positron annihilation emission data (i.e., LOR data), the radiation emitted by the radiation therapy system may be calculated by multiplying acquired PET emission data ($x_i$) with the RFM from the treatment planning system, masked with a spatial filter (BFZ) that limits the radiation delivery to the target region (i.e., biological firing zone) and optionally scaled with one or more normalization ($k_i$) and/or dampening factors ($\beta_i$). The acquired PET emission data ($x_i$) may comprise one or more LORs, but may not include a sufficient number of LORs for the generation of a complete or full PET image. For other radiation therapy systems, imaging data may comprise 2-D projection X-ray images (for a CT imaging system) or MRI sub-samplings in k-space (for a MRI imaging system). The normalization factor for the first shuttle pass ($k_1$) may be calculated based on a pre-scan image ($X_{prescan}$) of the patient acquired at the start of a treatment session.

In one variation, a normalization factor for a shuttle pass index i (where i=1, 2, . . . , N shuttle passes) may be calculated as follows:

$$k_i = \begin{cases} \dfrac{D_{plan}}{D_{0,raw}} & \text{for } i = 1 \\ \dfrac{D_{plan} - \sum_{j=1}^{i-1} k_j \beta_j D_{j,raw}}{\sum_{j=i}^{N} \beta_j D_{i-1,raw}} & \text{for } 2 \leq i \leq N \end{cases}$$

where $D_{plan}$ is the radiation dose or fluence as specified in the treatment plan, $\beta_i$ is a dampening factor, and $D_{i,raw}$ is the radiation fluence delivered (or to-be-delivered) for a shuttle pass i in accordance with the treatment plan without any adjustment based on real-time treatment session data. $D_{i,raw}$ may be a calculated radiation fluence (e.g., with continuous fluence values) or a segmented radiation fluence (e.g., with discrete fluence values or levels), where a segmented radiation fluence may comprise fluence values that represent the fluence values deliverable by a radiation therapy system. In some variations, for radiation delivery based on imaging data acquired during a treatment session, $$D_{0,raw} = \left(D_{prescan} \times \frac{\text{treatment time}}{\text{prescan time}}\right),$$

where $$D_{prescan} = A \times (X_{prescan} * RFM) \circ BFZ$$

where A is a dose calculation matrix generated based on radiation therapy system parameters that maps fluence to dose in the image space, $X_{prescan}$ is an image (e.g., a full image such as a full PET image, a full CT image, and/or a full MRI image) acquired at the beginning of a treatment session before any therapeutic radiation is delivered, RFM is a radiation-firing matrix generated by the treatment planning system that designates the conversion from image data (e.g., partial images, such as a set of LORs or 2-D X-ray projections or MRI sub-samplings in k-space, or incomplete image data) to a radiation beamlet pattern and/or beamlet intensities, and BFZ is a spatial filter comprising a bitmap that specifies the target region while masking out non-target regions. "Treatment time" is the total treatment delivery time defined by the treatment planning system, which may be selected or determined by a clinician or user, and "prescan time" is the total time spend acquiring the pre-scan image $X_{prescan}$.

The term $$\sum_{j=i}^{N} \beta_j D_{i-1,raw}$$

may represent the predicted cumulative fluence that would be applied to the target region if each of the future shuttle passes delivered the same amount of radiation as was delivered in the previous shuttle pass and may also be referred to as $D_{i,predicted\ cumulative}$ (which may not be segmented into fluence levels or values deliverable by a radiation therapy system). In some variations, $D_{i,predicted\ cumulative}$ may be expressed as:

$$D_{i, predicted\ cumulative} = \sum_{j=i+1}^{N} \beta_{j-1} D_{i-1, raw} = \sum_{j=i+1}^{N} \beta_{j-1}[(x_i * RFM) \circ BFZ]$$

For shuttle passes following the first shuttle pass ($2 \leq i \leq N$), the normalization factor $k_i$ may also be written as follows:

$$k_i = \frac{D_{plan} - \sum_{j=1}^{i-1} k_j \beta_j [(x_j * RFM) \circ BFZ]}{\sum_{j=i}^{N} \beta_j [(x_{i-1} * RFM) \circ BFZ]}, \text{ for } 2 \leq i \leq N$$

Where $x_i$ represents the imaging data acquired during shuttle pass i. In method (820), steps (822) and (826) may calculate the normalization factors $k_i$, and $k_{i+1}$ as described above.

The radiation fluence delivered in an $i^{th}$ shuttle pass ($D_{i,calc}$) may be calculated as follows:

$$D_{i,calc} = k_i \beta_i D_{i,raw} = k_i \beta_i [(x_i * RFM) \circ BFZ]$$

When applied to method (820), the radiation fluence emitted in (824) may be $k_i \beta_i [(x_i * RFM) \circ BFZ]$ and the radiation fluence emitted in (828) may be $k_{i+1} \beta_{i+1}[(x_{i+1} * RFM) \circ BFZ]$, where $x_i$, $x_{i+1}$ represent imaging data acquired during shuttle passes i and i+1, respectively.

Figure 8C:
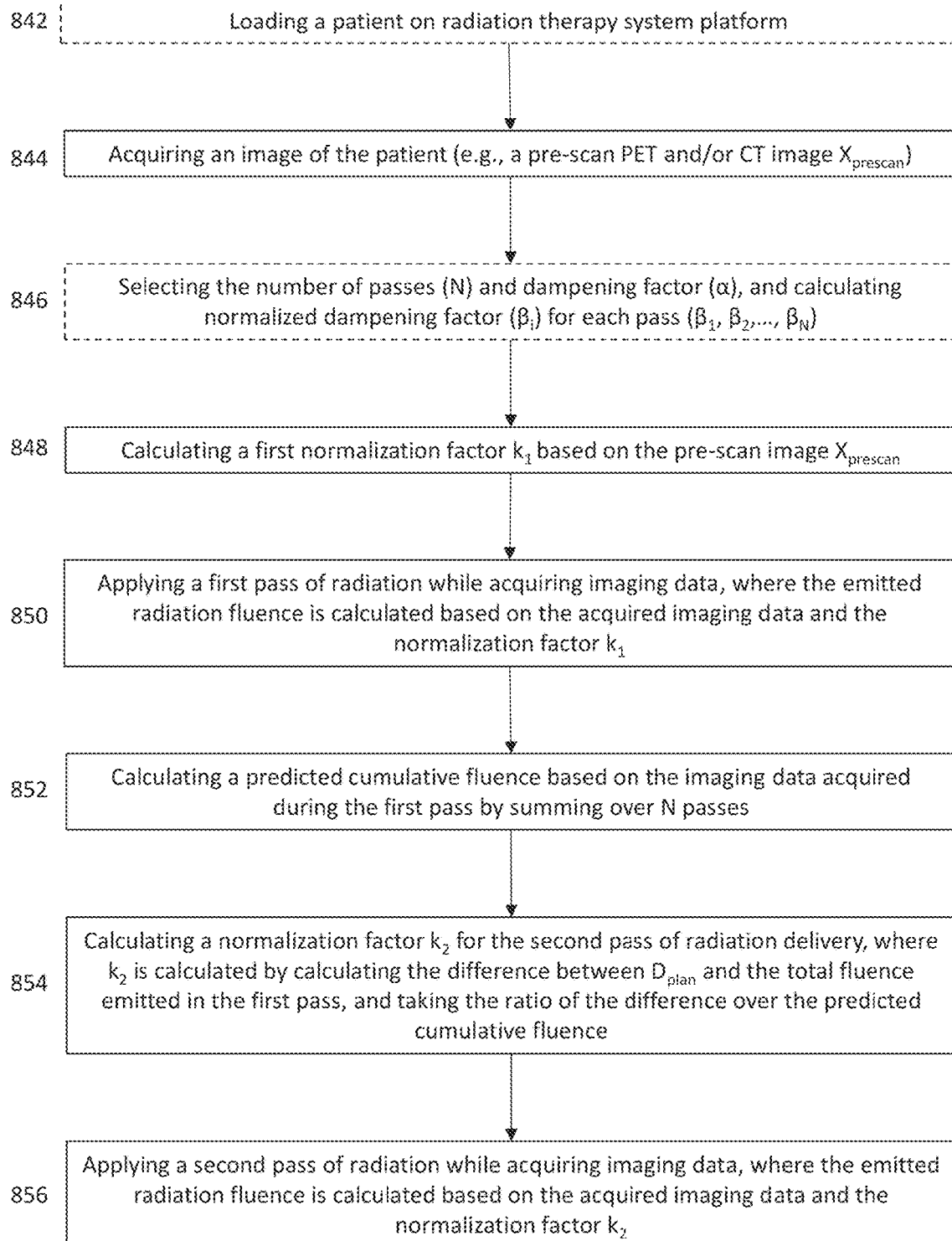
FIG. 8C depicts one variation of a pipelined normalization method.

FIG. 8C depicts one variation of a pipelined normalization method where the radiation applied during a shuttle pass is modified or adjusted according to a normalization factor that is calculated based on the most-recently acquired imaging data (e.g., partial and/or full images). Method (840) may be used with any image-guided or emission-guided (e.g., biologically-guided) radiotherapy where imaging data and/or patient data and/or system data is acquired during the radiation therapy session and used to adapt, modify or otherwise adjust radiation delivery. While the flowchart of FIG. 8C depicts the method applied to a first shuttle pass and to a second shuttle pass of radiation delivery, it should be understood that the method may also be extended for additional shuttle passes, as may be desired. Method (840) may optionally comprise loading (842) a patient on radiation therapy system platform, acquiring (844) an image of the patient (e.g., a pre-scan PET and/or CT image $X_{prescan}$), optionally selecting (846) the number of passes (N) and dampening factor ($\alpha$) and calculating normalized dampening factor ($\beta_i$) for each pass ($\beta_1, \beta_2, \ldots, \beta_N$), calculating (848) a first normalization factor $k_1$ based on the pre-scan image $X_{prescan}$, and applying (850) a first pass of radiation while acquiring imaging data $x_1$, where the emitted radiation fluence $D_{1,calc}$ is calculated based on the acquired imaging data and the normalization factor $k_1$. The number of passes and the calculation of the dampening factor for each of the shuttle passes may be calculated as described previously and at any time before the treatment session, for example, during treatment planning, before patient set up, and/or before the therapeutic radiation source is activated (i.e., beam on), and this step may be included in any of the other methods described herein. In this example, the normalization factor $k_1$ may be calculated or determined as follows:

$$k_1 = \frac{D_{plan}}{D_{0,raw}}$$

where $$D_{0,raw} = \left( D_{prescan} \times \frac{\text{treatment time}}{\text{prescan time}} \right),$$

where $$D_{prescan} = A \times (X_{prescan} * RFM) \circ BFZ$$

Where the dose calculation matrix A, radiation-firing matrix RFM, and biological firing zone bitmask BFZ are as described previously. The radiation applied in the first pass to a target region (e.g., a biological firing zone or radiation firing zone) based on the acquired imaging data may be calculated as follows:

$$D_{1,calc} = k_1 \beta_1 D_{1,raw} = k_1 \beta_1 [x_1 * RFM) \circ BFZ]$$

The image data $x_1$ acquired during the first shuttle pass may be partial images, for example, comprising one or more LORs (for image data acquired with PET detectors), one or more 2-D projection X-ray images (for image data acquired with CT detectors), and/or sub-samplings in k-space (for image data acquired with MRI detectors). While the treatment plan parameters (e.g., RFM, BFZ) may designate the delivery of a radiation fluence $D_{1,raw}$ to the target region, the normalization factor and dampening factor may adjust (i.e., scale or normalize) $D_{1,raw}$ to reflect the real-time treatment conditions during the session and/or compensate for variations and/or artifacts in the imaging data $x_1$ acquired during the first shuttle pass. $D_{1,raw}$ may be a calculated radiation fluence (e.g., with continuous fluence values) or a segmented radiation fluence (e.g., with discrete fluence values or levels), where a segmented radiation fluence may comprise fluence values that represent the fluence values deliverable by a radiation therapy system.

Method (840) may further comprise calculating (852) a predicted cumulative fluence ($D_{1,predicted\ cumulative}$) based on the imaging data acquired during the first pass by summing over N passes, calculating (854) a normalization factor $k_2$ for the second pass of radiation delivery where $k_2$ is calculated by calculating the difference between $D_{plan}$ and the total fluence emitted in the first pass, and taking the ratio of the difference over the predicted cumulative fluence, and applying (856) a second pass of radiation while acquiring imaging data, where the emitted radiation fluence $D_{2,calc}$ is calculated based on the acquired imaging data and the normalization factor $k_2$. The predicted cumulative fluence may be calculated (852) based on the imaging data acquired during the first shuttle pass:

$$D_{1,predicted\ cumulative} = \sum_{j=2}^{N} \beta_j D_{1,raw} = \sum_{j=2}^{N} \beta_j [(x_1 * RFM) \circ BFZ]$$

The normalization factor $k_2$ for the second shuttle pass may be calculated (854) by taking the difference between the planned radiation fluence or dose and the fluence emitted in the first shuttle pass, normalized over the predicted cumulative fluence:

$$k_2 = \frac{D_{plan} - D_{1,calc}}{D_{1,predicted\ cumulative}} = \frac{D_{plan} - k_1 \beta_1 D_{1,raw}}{\sum_{j=2}^{N} \beta_j D_{1,raw}}$$

Accordingly, the radiation applied in the second shuttle pass to the target region (e.g., a biological firing zone or radiation firing zone) based on the acquired imaging data during the second shuttle pass may be calculated as follows:

$$D_{2,calc} = k_2 \beta_2 D_{2,raw} = k_2 \beta_2 [(x_2 * RFM) \circ BFZ]$$

Where image data $x_2$ acquired during the second shuttle pass may be partial images, for example, comprising one or more LORs (for image data acquired with PET detectors), one or more 2-D projection X-ray images (for image data acquired with CT detectors), and/or sub-samplings in k-space (for image data acquired with MRI detectors), as described previously and throughout. $D_{2,raw}$ may be a calculated radiation fluence (e.g., with continuous fluence values) or a segmented radiation fluence (e.g., with discrete fluence values or levels), where a segmented radiation fluence may comprise fluence values that represent the fluence values deliverable by a radiation therapy system.

In some variations, the normalization factor for the first shuttle pass may be calculated using dose values derived from the pre-scan image, while the normalization factors for the successive shuttle passes may be calculated using fluence values (optionally be segmented fluence values, including any fluence segmentation errors). Dose calculations may be more computationally-intensive than fluence calculations (since fluence may be calculated by multiplying the image data with the radiation-firing matrix, while dose calculations may involve an additional multiplication with a dose calculation matrix), and it may therefore be preferable for some radiation therapy systems to calculate normalization factors during a treatment session using radiation fluence instead of radiation dose so that the latency between the acquisition of imaging data and the application of radiation is reduced. Since the first normalization factor is calculated before therapeutic beam-on, a radiation therapy system may be computationally available for calculating the first normalization factor based on the dose values derived from the pre-scan image. Some variations of radiation therapy systems may comprise one or more processors with greater computational power, in which case, the normalization factors may be calculated using dose values derived from the imaging data acquired during the treatment session. Alternatively or additionally, all normalization factors may be calculated on fluence values derived from image data acquired during the treatment session.

Figure 9A:
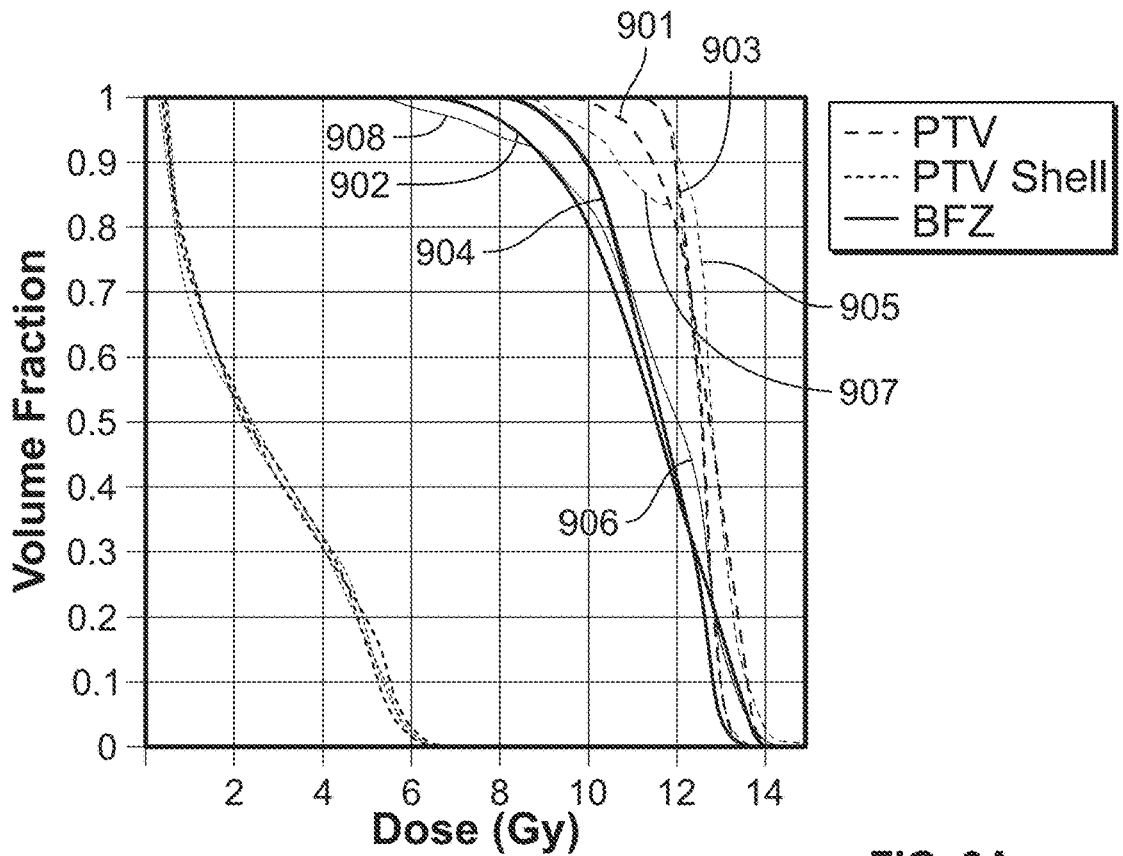
FIGS. 9A-9D depict simulation dose-volume plots or histograms (DVH) based on one variation of a method of radiation delivery over four couch shuttle passes to a planning target region (PTV) and biological firing zone (BFZ) region.
Figure 9B:
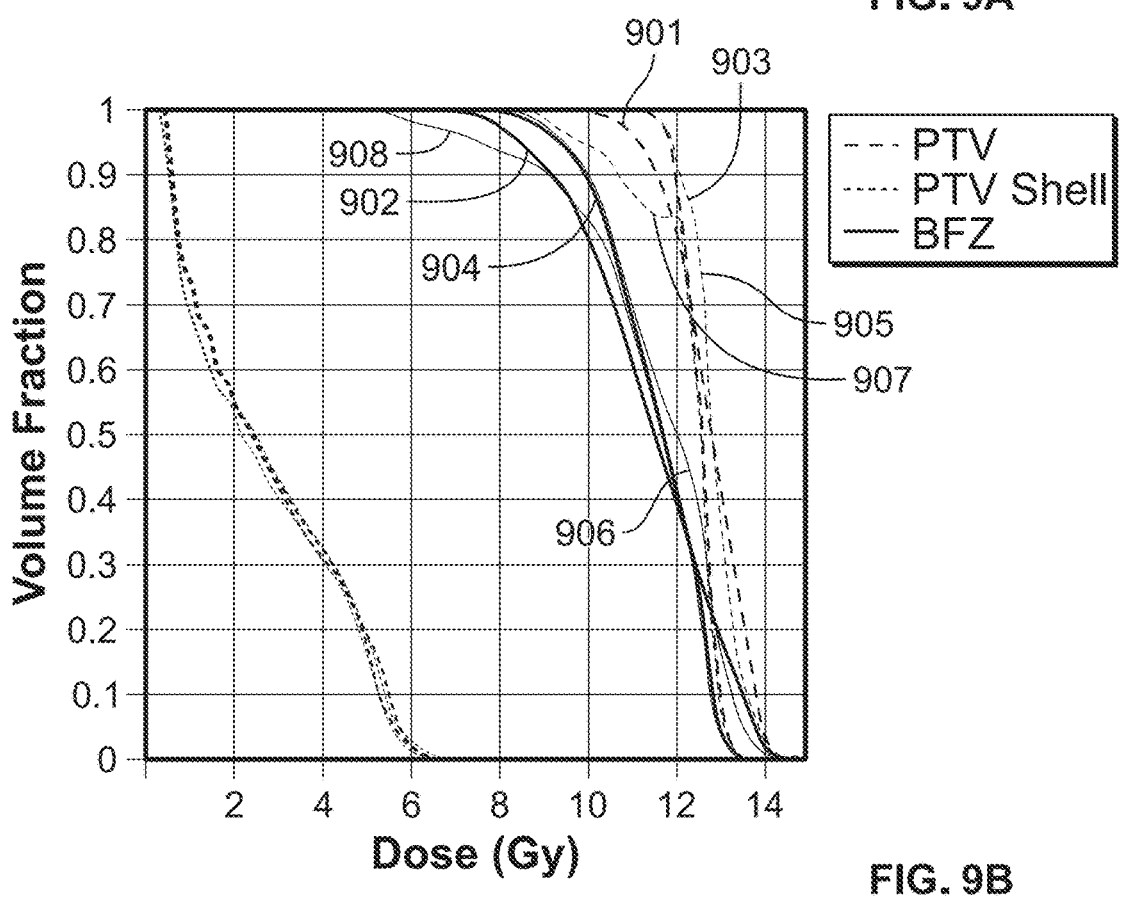
Figure 9C:
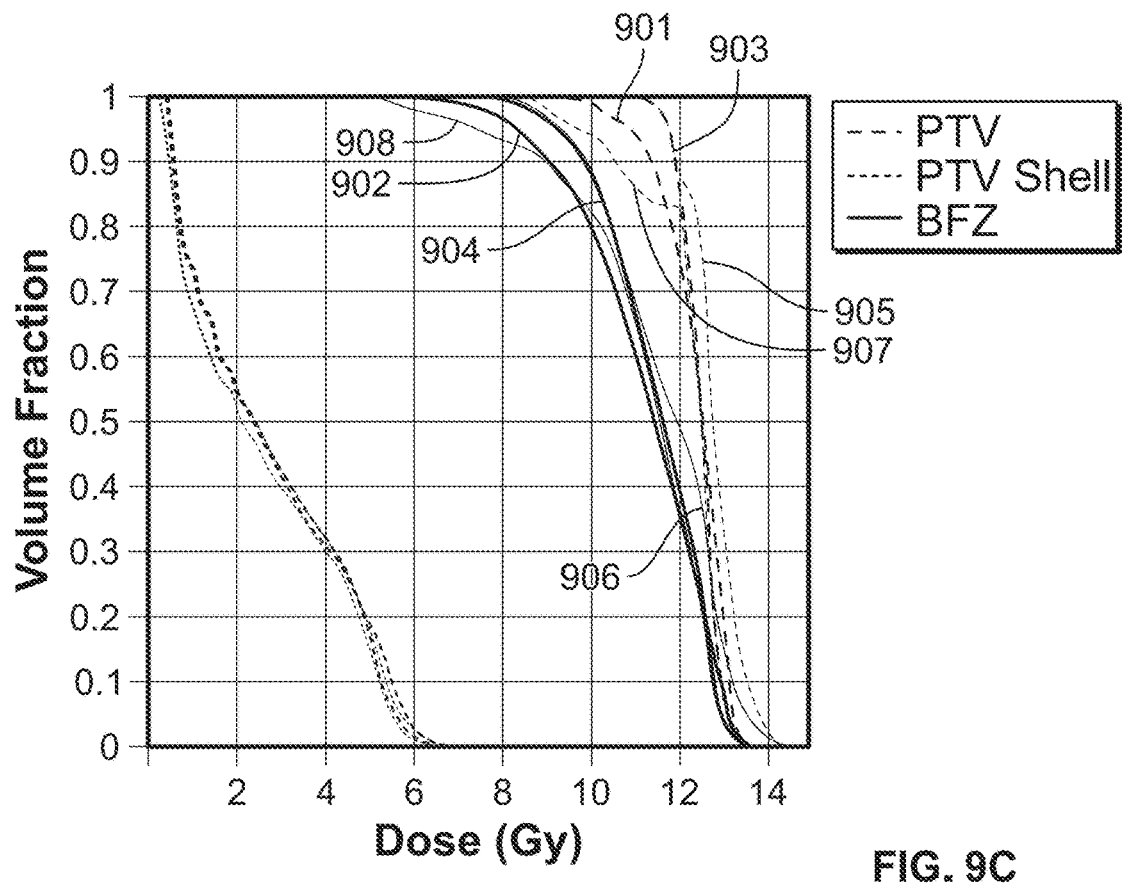
Figure 9D:
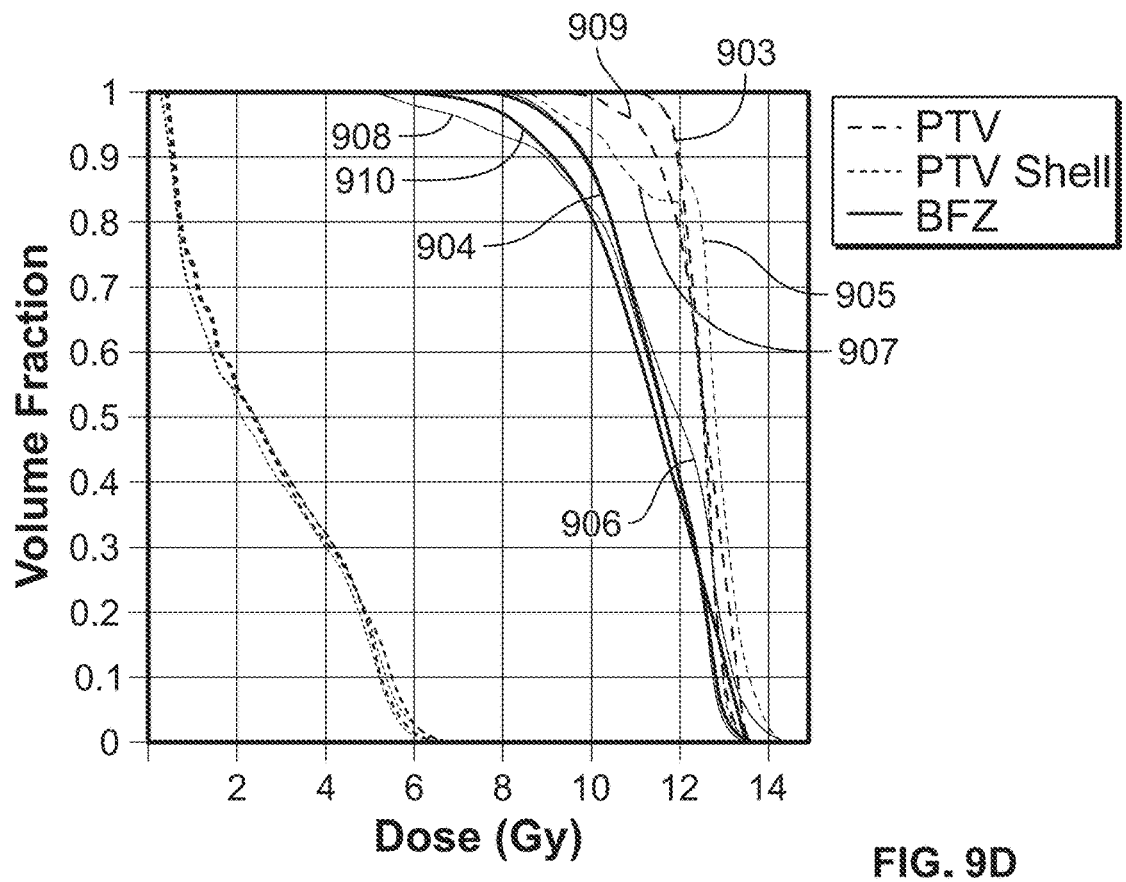

FIGS. 9A-9D are simulation dose-volume plots or histograms (DVH) that depict a method of radiation delivery over four couch shuttle passes to a planning target region (PTV) and biological firing zone (BFZ) region using one or more of the pipelined normalization methods described herein. The BFZ region includes the PTV and a margin around the PTV. FIG. 9A depicts the DVH curves after a first shuttle pass. The planned DVH for the PTV is represented by line (903), with the maximum DVH bound (i.e., upper threshold acceptable for treatment) represented by line (905) and the minimum DVH bound (i.e., lower threshold acceptable for treatment) represented by line (907). The predicted delivered dose to the PTV is represented by the delivered DVH line (901). Similarly, and the planned DVH for the BFZ region is represented by line (904), with the maximum DVH bound (i.e., upper threshold acceptable for treatment) represented by line (906) and the minimum DVH bound (i.e., lower threshold acceptable for treatment) represented by line (908). The predicted delivered dose to the BFZ region is represented by the delivered DVH line (902). After the first shuttle pass, the predicted DVH curve for the PTV (901) exceeds the planned DVH curve for the PTV (905), and falls out of range of the maximum DVH bound (905). Similarly, the predicted DVH curve for the BFZ region (902) exceeds the planned DVH curve for the BFZ region (904), and falls out of range of the maximum DVH bound (906). As the radiation delivered to the PTV and the BFZ region builds up over multiple shuttle passes, with FIG. 9B depicting the same DVH curves as in FIG. 9A after a second shuttle pass, with FIG. 9C depicting the DVH curves after a third shuttle pass, and with FIG. 9D depicting the DVH curves after a fourth shuttle pass, it may be seen how the delivered DVH curves (PTV DVH 909 and BFZ region DVH 910) converges toward the planned DVH curves (PTV DVH 903 and BFZ region DVH 904) and/or remain within the bounds defined by the maximum and minimum DVH curves for the PTV and BFZ regions, respectively.

Pipelined Normalization with Negative Fluence Values

Figure 10:
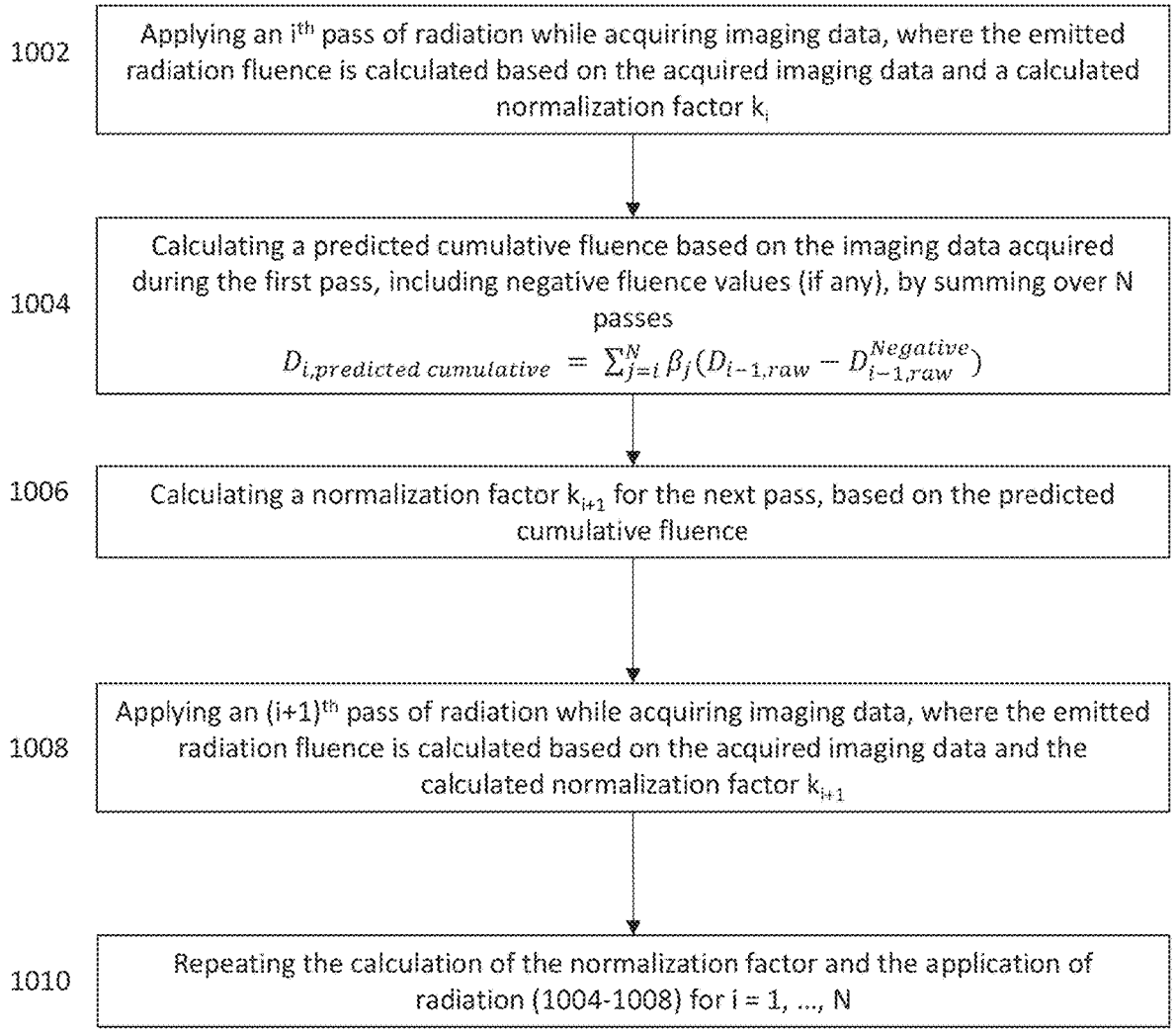
FIG. 10 depicts one variation of a method for radiation delivery.

In some variations, when calculating the radiation fluence for delivery, the calculated $D_{i,raw} = [(x_i * RFM) \circ BFZ]$ value may result in a negative radiation fluence value. A negative radiation fluence value may not be deliverable by the radiation therapy system in the same shuttle pass, however, if such negative fluence values are zeroed out and/or ignored, the cumulative delivered radiation may deviate substantially from the planned fluence or dose values. One variation of a method for handling negative fluence values accrued in one shuttle pass may comprise incorporating the negative fluence values into the next shuttle pass, where they may be combined with non-negative fluence values. The next fluence values may be positive and therefore, deliverable in one or more later shuttle passes. In some variations, the negative fluence values in one shuttle pass may be incorporated in the calculation of the predicted cumulative fluence that would be delivered over the remaining shuttle passes, and used to normalize the difference between $D_{plan}$ and $D_{i,calc}$ (i.e., total cumulative delivered radiation in the treatment session up until the next shuttle pass). FIG. 10 depicts one variation of a method where the radiation applied during a shuttle pass is modified or adjusted according to a normalization factor that is calculated before the shuttle pass begins, and incorporates negative fluence values encountered during radiation delivery in the previous pass. Method (1000) may comprise applying (1002) an $i^{th}$ pass of radiation while acquiring imaging data where the emitted radiation fluence is calculated based on the acquired imaging data and a calculated normalization factor $k_i$, calculating (1004) a predicted cumulative fluence based on the imaging data acquired during the first pass, including negative fluence values (if any), by summing over N passes, calculating (1006) a normalization factor $k_{i+1}$ for the next pass, based on the predicted cumulative fluence, and applying (1008) an $(i+1)^{th}$ pass of radiation while acquiring imaging data where the emitted radiation fluence is calculated based on the acquired imaging data and the calculated normalization factor $k_{i+1}$. Optionally, method (1000) may further comprise repeating the calculation of the normalization factor and the application of radiation (1004-1008) for i=1, . . . , N. The predicted cumulative fluence may incorporate negative fluence values as follows:

$$D_{i,predicted\ cumulative} = \sum_{j=i}^{N} \beta_j \left( D_{i-1,raw} - D_{i-1,raw}^{Negative} \right)$$

By incorporating the negative fluence value into the $D_{i,predicted\ cumulative}$, such negative fluence is accounted for in the generation of $k_i$ for the next shuttle pass, since $D_{i,predicted\ cumulative}$ is used to normalize the difference between the planned radiation fluence and the delivered radiation fluence.

Figure 11A:
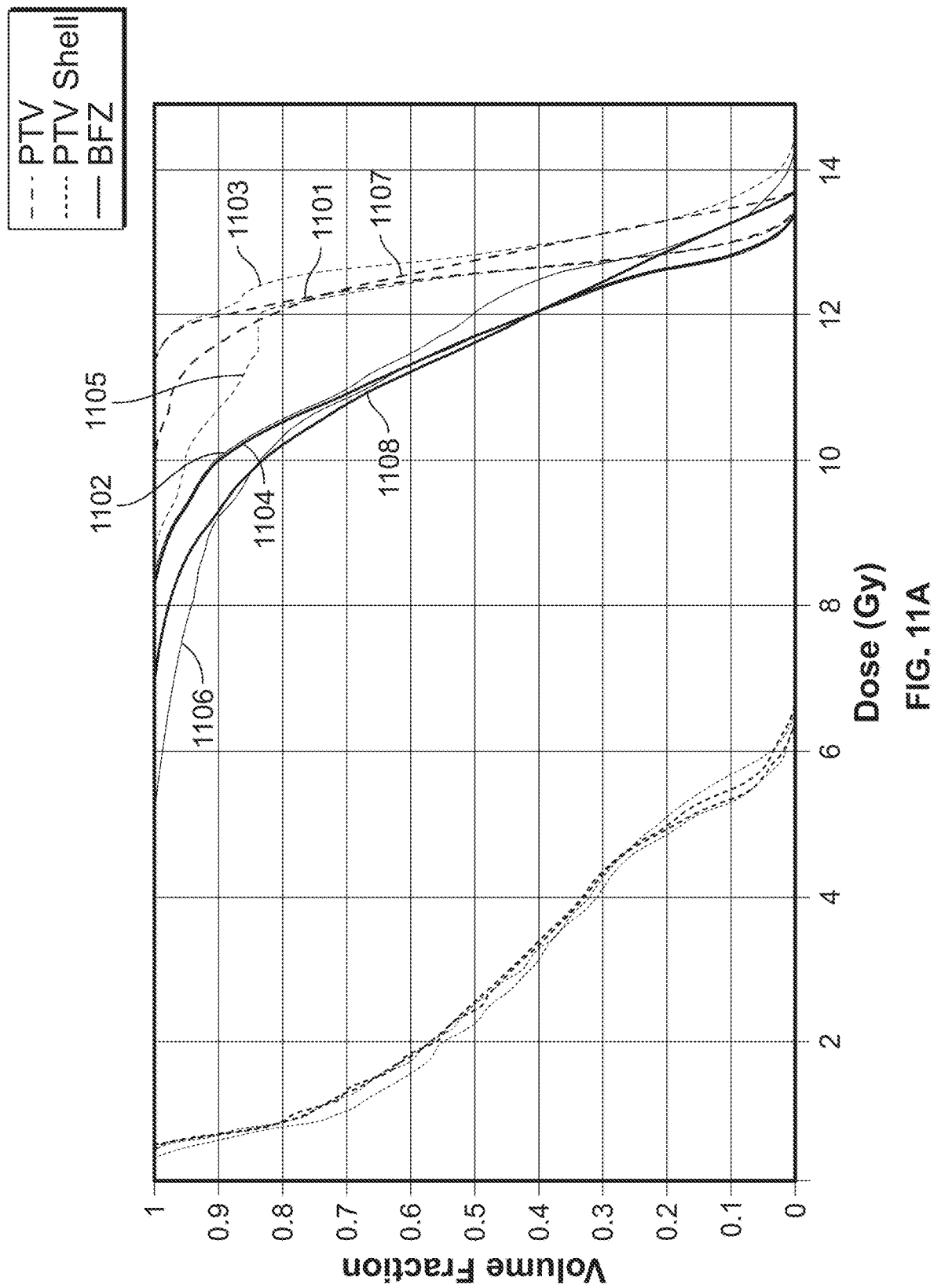
FIGS. 11A-11B are simulation DVH plots that depict the results of two methods of radiation delivery over four couch shuttle passes to a planning target region (PTV) and biological firing zone (BFZ).
Figure 11B:
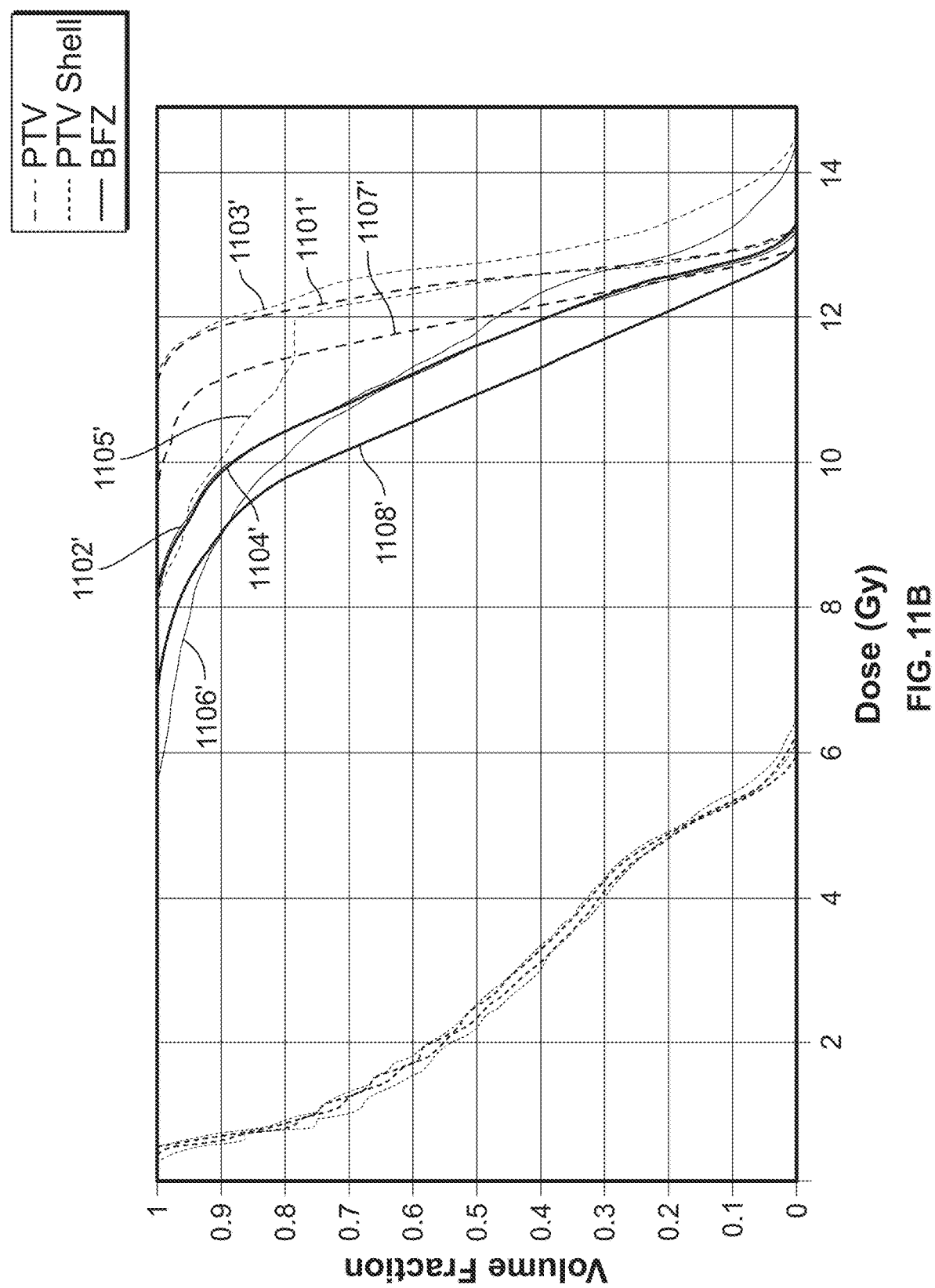

FIGS. 11A-11B are simulation DVH plots that depict the results of two methods of radiation delivery over four couch shuttle passes to a planning target region (PTV) and biological firing zone (BFZ). FIG. 11A depicts the result of radiation delivery to a PTV and BFZ region (as previously described) when negative fluence values are incorporated in the predicted cumulative fluence values and included in the calculation of the normalization factor k. The planned DVH curve for the PTV is represented by line (1101), with the maximum DVH curve represented by line (1103) and the minimum DVH curve represented by line (1105). The delivered DVH curve for the PTV is represented by line (1107), and as seen along the falling edge of the DVH curve, the delivered DVH curve for the PTV is located within the minimum and maximum DVH boundaries. Similarly, for the BFZ region, the planned DVH curve for the BFZ region is represented by line (1102), with the maximum DVH curve represented by line (1104) and the minimum DVH curve represented by line (1106). The delivered DVH curve for the BFZ region is represented by line (1108), and as seen along the falling edge of the DVH curve, the delivered DVH curve for the BFZ is located within the minimum and maximum DVH boundaries. In contrast, FIG. 11B depicts the result of radiation delivery to a PTV and BFZ region (as previously described) when negative fluence values are ignored. The planned DVH curve for the PTV is represented by line (1101'), with the maximum DVH curve represented by line (1103') and the minimum DVH curve represented by line (1105'). The delivered DVH curve for the PTV is represented by line (1107'), and as seen in the plot, the delivered DVH curve for the PTV is not located within the boundaries defined by the minimum and maximum DVH curves. Similarly, for the BFZ region, the planned DVH curve for the BFZ region is represented by line (1102'), with the maximum DVH curve represented by line (1104') and the minimum DVH curve represented by line (1106'). The delivered DVH curve for the BFZ region is represented by line (1108'), and as seen in the plot, the delivered DVH curve for the BFZ is not located within the boundaries defined by the minimum and maximum DVH curves. Including negative fluence values in the calculation of a normalization factor may be incorporated in any of the methods described herein.

Figures 12A, 12B, 12C:
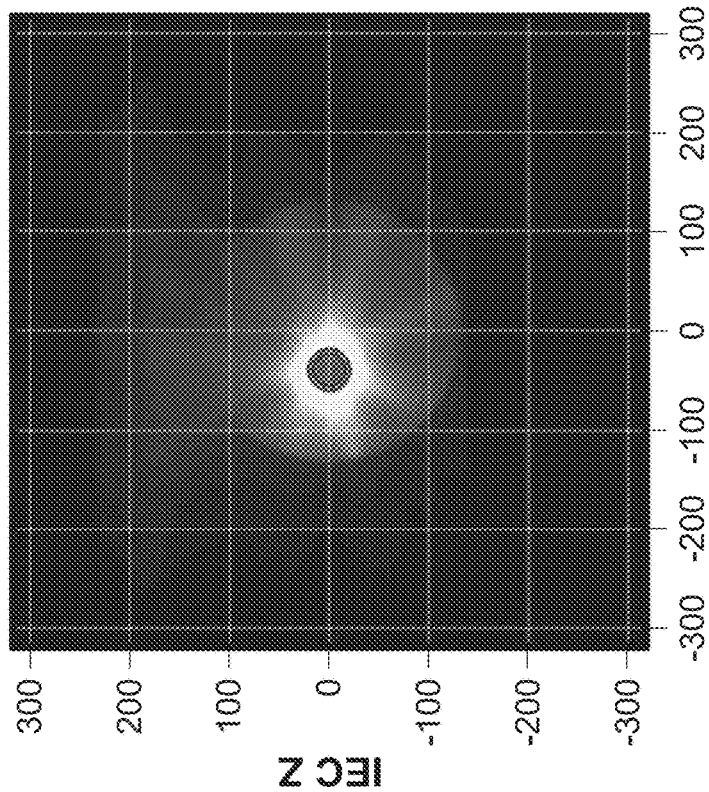
FIGS. 12A-12C depict multiple views of the planned dose distribution.
Figure 13B:
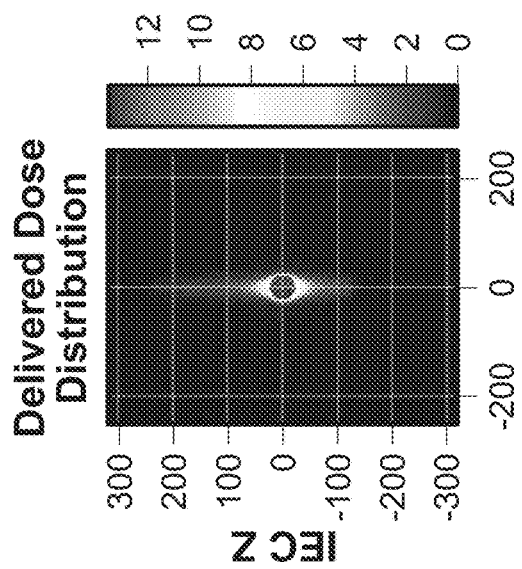
FIGS. 13A-13C depict multiple views of the planned dose distribution.
Figure 13C:
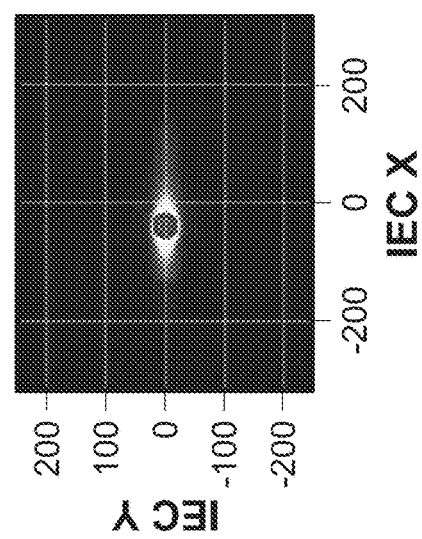
Figure 13A:
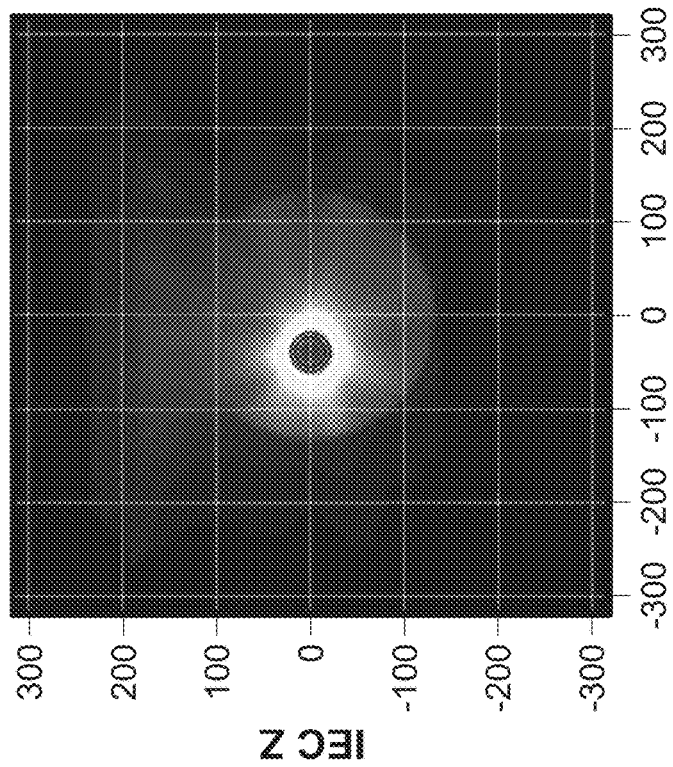
Figure 14D:
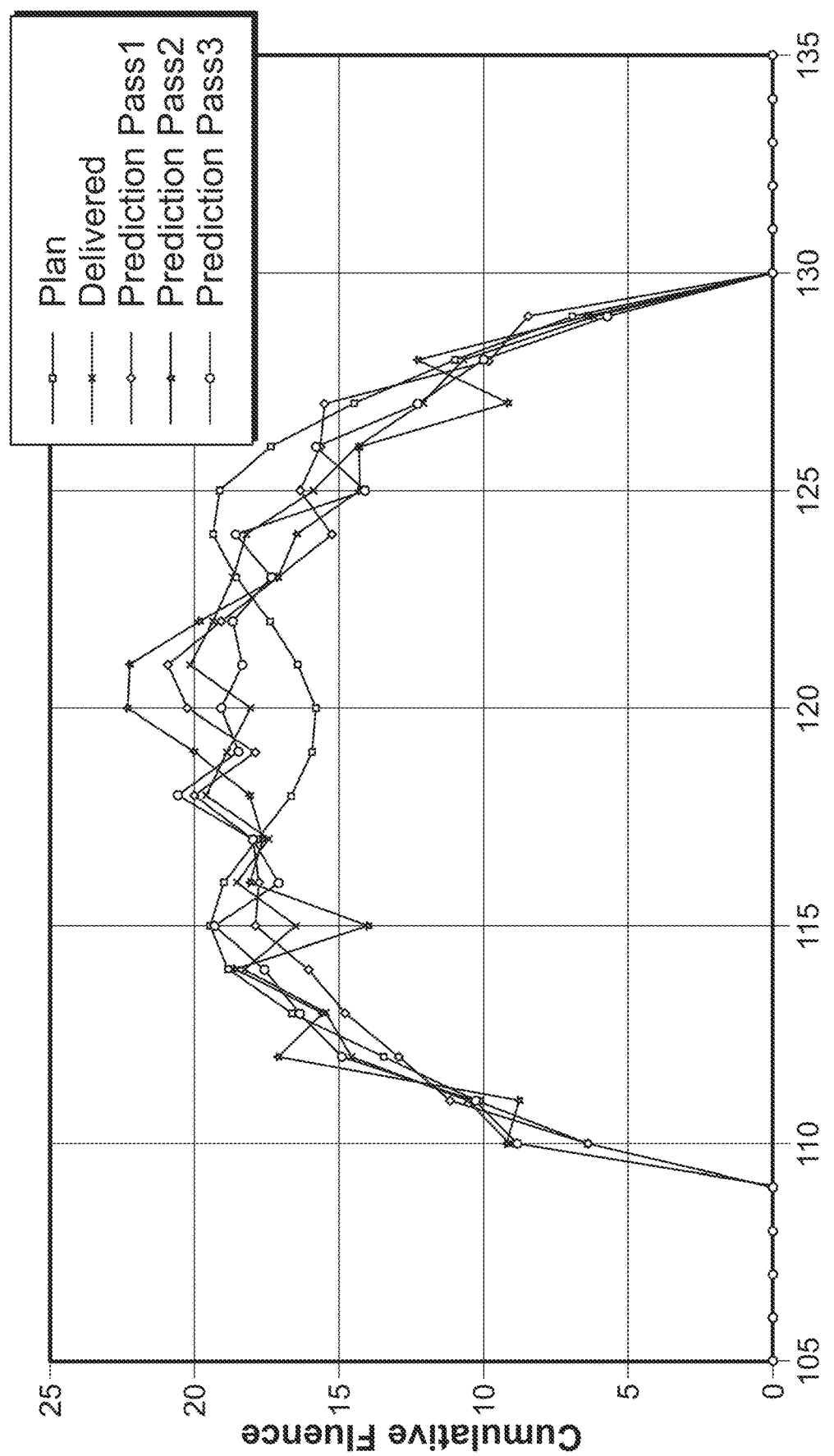
FIG. 14D depicts a plot that represents the cumulative fluence as a function of beam station for a treatment session with four shuttle passes.

The pipelined normalization methods for radiation delivery described herein may use the mean of the planned fluence (or dose) to constrain the mean of the delivered fluence (or dose). This may help the radiation therapy system to deliver radiation having a mean fluence that converges to the mean planned fluence, which may help to address motion and/or imaging artifacts encountered during the treatment session. FIGS. 12A-12C, 13A-C, and 14A-C depict multiple views of the planned dose distribution, delivered dose distribution over four shuttle passes, and the γ metric, respectively, from multiple planes. The γ (gamma) metric may be calculated as the square root of the squared sum of distance to agreement (DTA) and percentage dose difference (DD) between two dose distributions. One of the dose distribution may be defined as reference dose distribution (typically the ground truth) and the other one may be defined as evaluated dose distribution. The established values for DTA may be 3 mm and DD may be 3%. The gamma metric may be first calculated for all pair of voxels in the two dose distributions and a passing value may be defined as value of gamma <=1 and fail may be defined as value of gamma >1. The gamma passing rate may be calculated as the percentage of voxels in the treatment volume that pass the gamma evaluation. The treatment volume may typically be defined as the voxels in the reference dose distribution that receive more than 10% of the prescribed dose. FIGS. 12A, 13A, and 14A depict the projection of the dose distribution on the IEC-Z/IEC-X plane (i.c., the plane orthogonal to the direction of couch motion), FIGS. 12B, 13B, and 14B depict the projection of the dose distribution on the IEC-Z/IEC-Y plane, and FIGS. 12C, 13C, and 14C depict the projection of the dose distribution on the IEC-Y/IEC-X plane (i.e., the plane orthogonal to the treatment beam, "beam's eye view"). As may be seen in FIGS. 14A-C the y metric passing rate (i.e., gamma value less than or equal to one) is over 99% when radiation delivery based on imaging data acquired during the treatment session is adjusted or modified with a normalization factor generated using one or more of the methods described herein. Regions where the gamma metric exceed one (as indicated by arrows (1400)) make up less than 1% of the total distribution depicted in FIGS. 14A-14C. FIG. 14D is a plot that depicts the cumulative fluence as a function of beam station for a treatment session with four shuttle passes. Each of the prediction passes are calculated as the sum of predicted fluence for remaining passes and delivered fluence. The delivered is the final fluence that is delivered to the tumor site. Each beam station is a predetermined couch location or step along the IEC-Y axis where the couch may be stopped while the therapeutic radiation beam is activated and applying radiation to the patient. The therapeutic radiation beam is off (i.e., not activated) while the couch is moving between beam stations. The line with the square-shaped bullets represents the planned fluence and the line with the cross-shaped bullets represents the fluence delivered after four shuttle passes. As depicted there, the mean delivered cumulative fluence converges toward the mean of the planned fluence with each additional shuttle pass. While the examples described herein comprise applying radiation over four shuttle passes, it should be understood that the number of shuttle passes over a treatment session may vary, and may be from 2 shuttle passes to 100 shuttle passes, e.g., 4 shuttle passes, 6 shuttle passes, 7 shuttle passes, 8 shuttle passes, 10 shuttle passes, 12 shuttle passes, etc.

Treatment Interruption

If a treatment session is not completed or interrupted (e.g., due to patient discomfort or illness, system component malfunction, etc.), a "make-up" fraction may be performed. A make-up fraction can be an entirely new treatment session or fraction (e.g., requiring a new patient setup), or simply a continuation of the incomplete fraction (e.g., without requiring a new patient setup) from the point where the interruption has occurred. If the make-up fraction requires a new patient setup, the different setup error might cause a so-called field junctioning error, which may result in underdosing or overdosing part(s) of the tumor target region and/or critical structures. Junctioning errors may be mitigated using a method similar to that described above and depicted in FIG. 6. The fluence or dose delivered to the patient until the interruption occurred may be calculated. This calculated delivered fluence and/or dose may be compared to the planned fluence and/or dose. The fluence and/or dose difference between the delivered and planned fluence and/or dose Δf may be used to update the RFM. The fluence Δf may then be delivered to the patient using the updated RFM in a later treatment session or fraction.

One variation of a method for continuing radiation therapy after an interruption where the patient remains on the platform or couch before and after the interruption (i.e., a continuation of the interruption treatment session, using the same patient setup parameters and pre-scan image) may comprise continuing the interrupted shuttle pass by moving the patient platform to the beam station where the interruption occurred, and resuming radiation delivery using the same normalization factor as was used before the interruption, and calculating the normalization factor for the next shuttle pass based on imaging data acquired during before the interruption and the imaging data acquired after the interruption. The normalization factor for the shuttle pass following the interruption may be calculated by taking the difference between $D_{plan}$ and the sum of the radiation delivered during the completed shuttle passes, the partial shuttle pass before the interruption, and the resumed partial shuttle pass after the interruption, and normalizing the difference over the predicted cumulated fluence that would be delivered if each of the future shuttle passes delivered the same amount of radiation as was delivered in the interrupted pass (i.e., the radiation delivered during the partial shuttle pass before the interruption and the resumed partial shuttle pass after the interruption). For example, the normalization factor $k_i$ for a treatment session with N total shuttle passes and the interrupt occurred in the $m^{th}$ pass may be calculated as follows:

$D_{i-1,calc}$ is defined as the delivered dose for the i−1 pass as defined previously. The numerator is calculated as the difference of the $D_{plan}$ and sum of $D_{i-1,calc}$ for all previous passes.

$$k_i = \begin{cases} \dfrac{D_{plan} - D_{i-1,calc}}{D_{i-1,predicted\ cumulative}}, \text{ for } 1 \leq i \leq m \\ \dfrac{D_{plan} - (D_{i-1,calc} + D_{m,pre-interrupt} + D_{m,post-interrupt})}{D_{i-1,predicted\ cumulative}}, \text{ for } i = m+1 \\ \dfrac{D_{plan} - (D_{p-1} + D_{i-1,calc})}{D_{i-1,predicted\ cumulative}}, \text{ for } i > m+1 \end{cases}$$

Where $D_{p-1}=(D_{i-1,calc}+D_{m,pre-interrupt})$ and $D_{plan}$, $D_{i,calc}$, etc. are calculated as described previously.

Figure 15A:
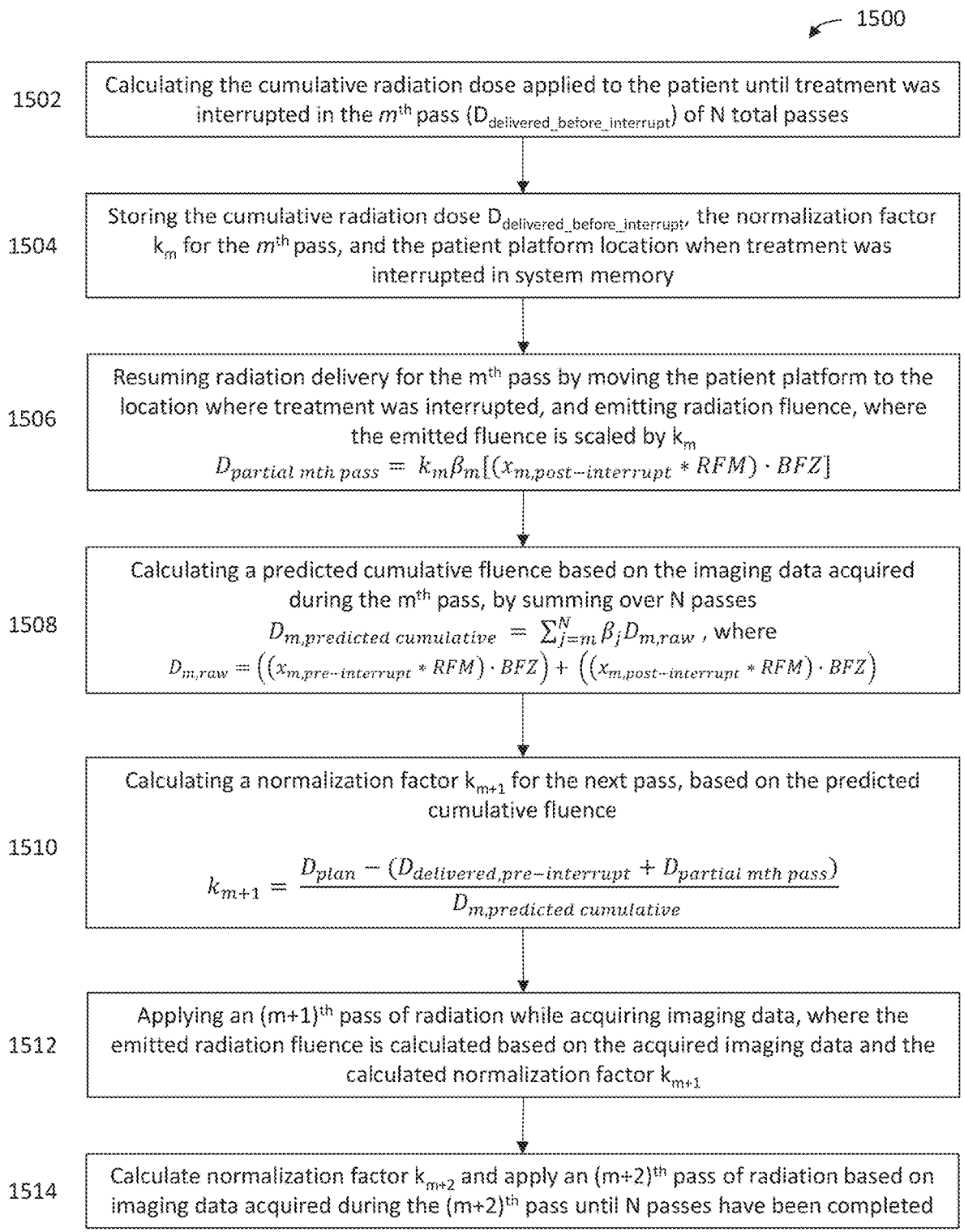
FIG. 15A depicts one variation of a method of radiation delivery when there has been an interruption during a shuttle pass, where radiation delivery is resumed without a new pre-scan image.

FIG. 15A depicts one variation of a method of radiation delivery when there has been an interruption during a shuttle pass and the patient remains on the platform to continue the interrupted treatment session (i.e., no new pre-scan image). Method (1500) may comprise calculating (1502) the cumulative radiation dose applied to the patient until treatment was interrupted in the mth pass ($D_{delivered\_before\_interrupt}$) of N total shuttle passes, storing (1504) the cumulative radiation dose $D_{delivered\_before\_interrupt}$, the normalization factor $k_m$ for the $m^{th}$ pass, and the patient platform location when treatment was interrupted in system memory, and resuming radiation delivery (1506) for the $m^{th}$ pass by moving the patient platform to the location (e.g., beam station) where treatment was interrupted, and emitting radiation fluence, where the emitted fluence is scaled by $k_m$. The radiation delivered in the resumed $m^{th}$ partial pass may be calculated as follows:

$$D_{partial\ mth\ pass}=k_m\beta_m[(x_{m,post-interrupt}*\text{RFM})\circ\text{BFZ}]$$

The method (1500) may comprise calculating (1508) a predicted cumulative fluence based on the imaging data acquired during the $m^{th}$ pass, by summing over N passes, calculating (1510) a normalization factor $k_{m+1}$ for the next pass, based on the predicted cumulative fluence, applying (1512) an $(m+1)^{th}$ pass of radiation while acquiring imaging data, where the emitted radiation fluence is calculated based on the acquired imaging data and the calculated normalization factor $k_{m+1}$, and calculating (1514) normalization factor $k_{m+2}$ and apply an $(m+2)^{th}$ pass of radiation based on imaging data acquired during the $(m+2)^{th}$ pass until N passes have been completed. The predicted cumulative fluence may be calculated (1508) as follows:

$$D_{m,predicted\ cumulative} = \sum_{j=m}^{N} \beta_j D_{m,raw}, \text{ where}$$

$$D_{m,raw} = ((x_{m,pre-interrupt}*RFM)\circ BFZ) + ((x_{m,post-interrupt}*RFM)\circ BFZ)$$

The normalization factor $k_{m+1}$ may be calculated (1510) as follows:

$$k_{m+1} = \dfrac{D_{plan} - (D_{delivered,pre-interrupt} + D_{partial\ mth\ pass})}{D_{m,predicted\ cumulative}}$$

For example, if radiation delivery is interrupted in the second shuttle pass (without a need for a new setup or new pre-scan image), the second shuttle pass may be resumed using the normalization factor $k_2$ (i.e., same as was before the interruption), and the normalization factor for subsequent shuttle passes may be calculated as follows:

$$k_i = \dfrac{D_{plan} - \left(k_1\beta_1 D_{1,raw} + \sum_{j=2}^{i-1} k_j\beta_j D_{j,raw}\right)}{\left(\sum_{j=i}^{N}\beta_j\right)D_{j,raw}}, \text{ for } i = 3{:}N$$

Figure 16:
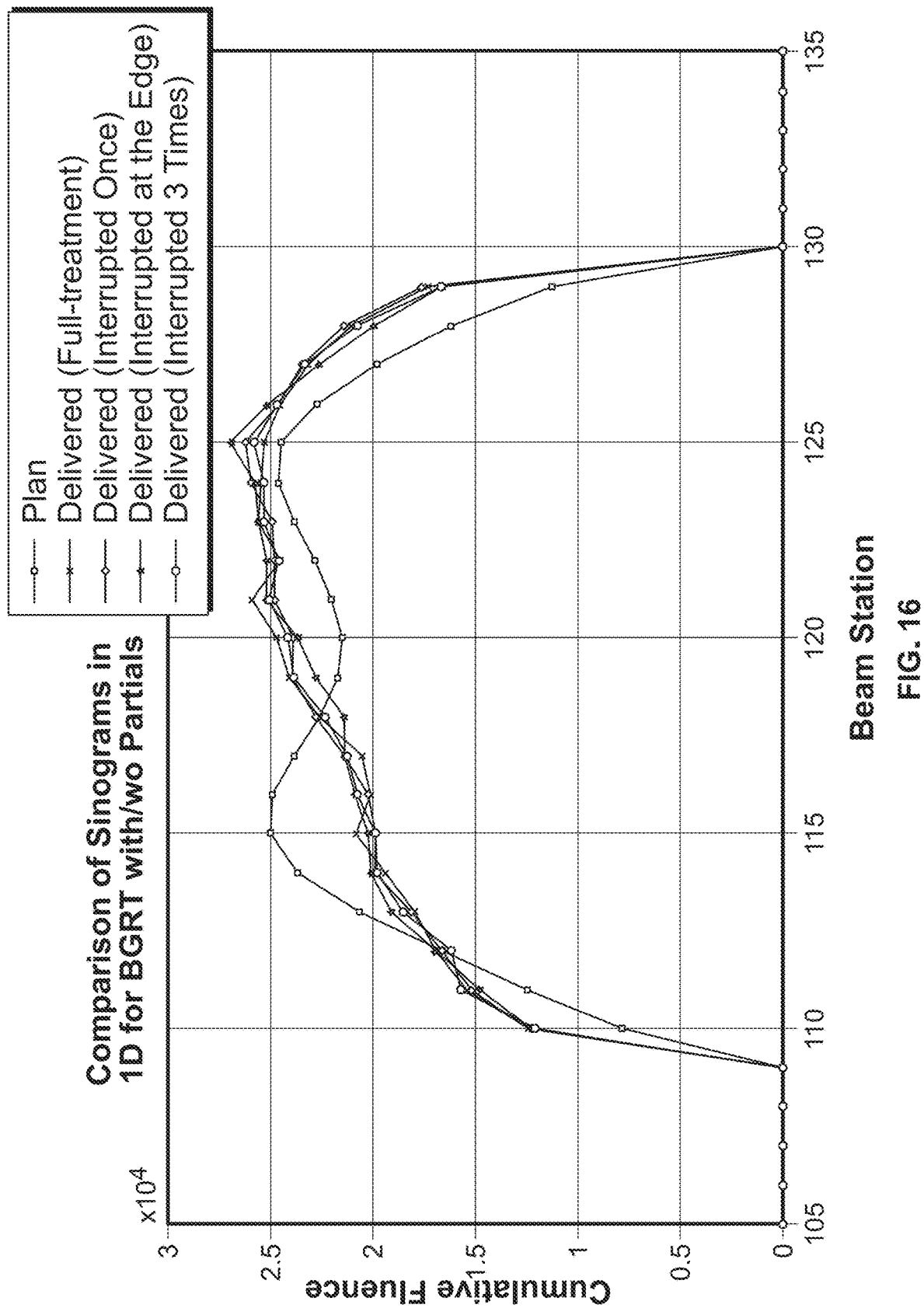
FIG. 16 is a plot that depicts the cumulative fluence as a function of beam station for a treatment session with four shuttle passes, where the treatment was interrupted at the second shuttle pass, with various interruption characteristics.

FIG. 16 is a plot that depicts the cumulative fluence as a function of beam station for a treatment session with four shuttle passes, where the treatment was interrupted at the second shuttle pass, with various interruption characteristics to evaluate and characterize the accuracy of the above-described method for handling treatment interruptions as compared with a treatment session without any interruptions (line with cross shaped bullets). The value of dampening factor used for this simulation is ($\alpha$=1/1.2). The line with the square-shaped bullets represents the planned fluence and the line with the cross-shaped bullets represents the fluence delivered after four shuttle passes without any interruptions. The line with the diamond-shaped bullets represents the fluence delivered after four shuttle passes with a single interruption in the middle of the second shuttle pass. The line with the star-shaped bullets represents the fluence delivered after four shuttle passes with a single interruption at the end of the second shuttle pass as the couch is changing directions between the second pass and the third pass. The line with the circle-shaped bullets represents the fluence delivered after four shuttle passes with a three interruptions. As depicted in the plot, updating the normalization factor with the fluence emitted before and after the interruption helps the average of the cumulative delivered radiation fluence to converge toward the average planned radiation fluence despite the interruptions in the treatment session. The fluence curves for the treatment sessions with interruptions (i.e., lines with diamond-, star-, and circle-shaped bullets) track closely with the curve for the treatment session without interruptions (i.e., line with cross-shaped bullets).

Figure 15B:
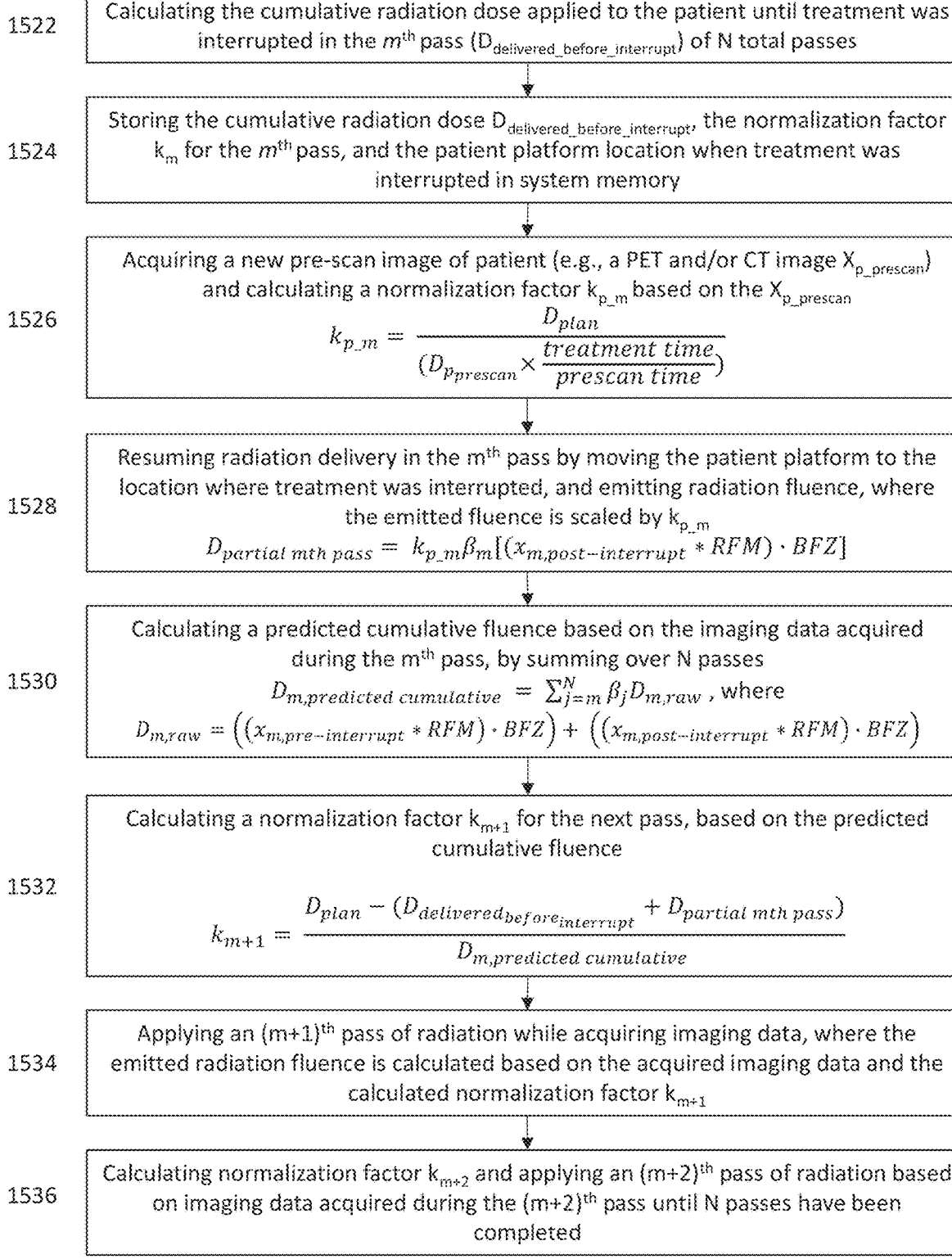
FIG. 15B depicts one variation of a method of radiation delivery when there has been an interruption during a shuttle pass, where radiation delivery is resumed using a new pre-scan image.

In some variations, radiation delivery is unable (or not desired) to be resumed in the same session and the patient may be removed from the system and scheduled to resume treatment on an another occasion. For example, the patient may feel too ill to proceed with radiation delivery on a particular day and/or radiation therapy system components may not function within specified tolerances and cannot be calibrated with the patient in the bunker. When the patient returns to resume radiation delivery, a new set up and new pre-scan image may be acquired. In some variations, the patient platform may be moved to the location and/or beam station where the interruption occurred in the previous treatment. Radiation delivery methods may account for the new setup and/or pre-scan image and the radiation fluence that was delivered in the previous, interrupted session when calculating a normalization factor for resuming radiation delivery. FIG. 15B depicts one variation of a radiation delivery method where the radiation delivered may be adjusted by a normalization factor that is derived at least in part based on the radiation fluence delivered in a prior treatment session and a pre-scan image acquired for the current session is depicted in FIG. 15B. Method (1520) may comprise calculating (1522) the cumulative radiation dose applied to the patient until treatment was interrupted in the $m^{th}$ pass ($D_{delivered\_before\_interrupt}$) of N total passes, storing (1524) the cumulative radiation dose $D_{delivered\_before\_interrupt}$, the normalization factor $k_m$ for the $m^{th}$ pass, and the patient platform location when treatment was interrupted in system memory (e.g., location along the IEC-Y axis and/or beam station index), and after the patient has returned to the radiation therapy system, acquiring (1526) a new pre-scan image of patient (e.g., a PET and/or CT image $X_{p\_prescan}$) and calculating a normalization factor $k_{p\_m}$ based on the $X_{p\_prescan}$, and resuming (1528) radiation delivery in the $m^{th}$ pass by moving the patient platform to the location where treatment was interrupted, and emitting radiation fluence, where the emitted fluence is scaled by $k_{p\_m}$. The normalization factor $k_{p\_m}$ may be calculated (1526) as follows:

$$k_{p\_m} = \frac{D_{plan}}{\left(D_{p\,prescan} \times \frac{\text{treatment time}}{\text{prescan time}}\right)}$$

Where $D_{plan}$, $\beta_j$ are as described previously, and $D_{p\,prescan}$ is the radiation fluence calculated based on the new pre-scan image $X_{p\_prescan}$. The radiation fluence delivered (1528) to resume the interrupted $m^{th}$ shuttle pass may be determined (1528) as follows:

$$D_{partial\,mth\,pass} = k_{p\_m}\beta_m[(x_{m,post-interrupt} * RFM) \circ BFZ]$$

Where $x_{m,post-interrupt}$ is the imaging data acquired in the $m^{th}$ shuttle pass after the interruption. Method (1520) may also comprise calculating (1530) a predicted cumulative fluence based on the imaging data acquired during the $m^{th}$ pass, by summing over N passes, calculating (1532) a normalization factor $k_{m+1}$ for the next pass, based on the predicted cumulative fluence, applying (1534) an $(m+1)^{th}$ pass of radiation while acquiring imaging data, where the emitted radiation fluence is calculated based on the acquired imaging data and the calculated normalization factor $k_{m+1}$, and optionally calculating (1536) a normalization factor $k_{m+2}$ and applying an $(m+2)^{th}$ pass of radiation based on imaging data acquired during the $(m+2)^{th}$ pass until N passes have been completed. The predicted cumulative fluence may be calculated (1530) as follows:

$$D_{m,predicted\,cumulative} = \sum_{j=m}^{N} \beta_j D_{m,raw}, \text{ where}$$

$$D_{m,raw} = ((x_{m,pre-interrupt} * RFM) \circ BFZ) + ((x_{m,post-interrupt} * RFM) \circ BFZ)$$

Where $x_{m,pre-interrupt}$ comprises the imaging data acquired in the $m^{th}$ shuttle pass before the interrupt, and $x_{m,post-interrupt}$ comprises the imaging data acquired in the $m^{th}$ shuttle pass after the interrupt (i.e., resuming the interrupted shuttle pass). The normalization factor $k_{m+1}$ may be calculated (1532) as follows:

$$k_{m+1} = \frac{D_{plan} - (D_{delivered\_before\_interrupt} + D_{partial\,mth\,pass})}{D_{m,predicted\,cumulative}}$$

Where $D_{delivered\_before\_interrupt}$ is the cumulative radiation fluence delivered before the interrupted shuttle pass and $D_{partial\,mth\,pass}$ is the radiation fluence delivered during the resumed interrupted pass (e.g., the portion of the $m^{th}$ pass that was undelivered due to the interruption).

Controller

A system (e.g., a treatment planning system, radiation therapy system) that may be configured to deliver therapeutic radiation to a patient may comprise a controller in communication with the imaging system of the radiation therapy system and/or the therapeutic radiation source and/or the multi-leaf collimator and/or gantry. The controller may comprise one or more processors and one or more machine-readable memories in communication with the one or more processors, which may be configured to execute or perform any of the methods described herein (e.g., the methods described and depicted in FIGS. 4, 5, 6, 7, 8A-8C, 10, 15A-15B). The controller of a radiation therapy system may be connected to or other systems by wired or wireless communication channels. In some variations, the controller of a treatment planning system may be located in the same or different room as the patient. For example, the controller may be coupled to a patient platform or disposed on a trolley or medical cart adjacent to the patient and/or operator.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smartphones, cell phones, tablet PCs, phablets (personal computing devices that are larger than a smartphone, but smaller than a tablet), and the like.

Processor

In some embodiments, a processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

Memory

In some embodiments, memory may include a database and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with the system, such as one or more treatment plans, full or high SNR images, partial or low SNR images, the calculation of fluence maps based on treatment plan and/or clinical goals, segmentation of fluence maps into radiation therapy system instructions (e.g., that may direct the operation of the gantry, therapeutic radiation source, multi-leaf collimator, and/or any other components of a radiation therapy system and/or diagnostic or treatment planning system), normalization factors, dampening factors, calculated and/or measured quantities of delivered or emitted radiation fluence or dose, patient platform or couch positions, and image and/or data processing associated with treatment planning and/or delivery.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

A user interface may serve as a communication interface between an operator or clinician and the radiation therapy system. The user interface may comprise an input device and output device (e.g., touch screen and display) and be configured to receive input data and output data from one or more of the support arm, external magnet, sensor, delivery device, input device, output device, network, database, and server. Sensor data from one or more sensors may be received by user interface and output visually, audibly, and/or through haptic feedback by one or more output devices. As another example, operator control of an input device (e.g., joystick, keyboard, touch screen) may be received by user and then processed by processor and memory for user interface to output a control signal to the radiation therapy system components (e.g., gantry, MLC, therapeutic radiation source, imaging systems, PET detectors, etc.).

Some variations of a radiation therapy system for delivering therapeutic radiation may comprise a display device that may allow an operator to view graphical and/or textual representations of fluence maps, and/or dose distributions, and/or regions of interest, and/or volumes of interest, and/or patient anatomical images, and/or patient data (e.g., physiological and/or biological), DVH curves, dose plots, and the like. In some variations, an output device may comprise a display device including at least one of a light emitting diode (LED), liquid crystal display (LCD), electroluminescent display (ELD), plasma display panel (PDP), thin film transistor (TFT), organic light emitting diodes (OLED), electronic paper/e-ink display, laser display, and/or holographic display.

Communication

In some embodiments, a treatment planning system and/or radiation therapy system may be in communication with other computing devices via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

While various inventive variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive variations described herein. It is, therefore, to be understood that the foregoing variations are presented by way of example only and that, within the scope of the appended claims and equivalents thereto, inventive variations may be practiced otherwise than as specifically described and claimed. Inventive variations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for updating a treatment plan fluence map, the method comprising:
   acquiring PET imaging data originating from a target region using PET detectors;
   identifying a location of the target region from the acquired PET imaging data; and
   updating a treatment plan fluence map for irradiating the target region using the identified location, wherein updating the treatment plan fluence map comprises scaling a planned fluence using one or more of a normalization factor, a dampening factor, and a weighting factor.

2. The method of claim 1, wherein the PET detectors comprise time-of-flight PET detectors.

3. The method of claim 1, further comprising acquiring MV detector data, and wherein updating the treatment plan fluence map uses the acquired MV detector data.

4. The method of claim 1, further comprising delivering radiation to the target region according to the updated treatment plan fluence map using a therapeutic radiation source.

5. The method of claim 4, wherein delivering radiation to the target region comprises adjusting a speed of a couch while the therapeutic radiation source is emitting radiation.

6. The method of claim 1, wherein delivering radiation occurs in at least two separate passes of a couch through radiation emitted by a therapeutic radiation source.

7. The method of claim 6, wherein updating the treatment plan fluence map comprises updating the treatment plan fluence map after a first couch pass and updating the treatment plan fluence map after a second couch pass.

8. The method of claim 7, wherein the normalization factor is dynamically updated for the second couch pass based on radiation delivered during the first couch pass.

9. The method of claim 1, wherein updating the treatment plan fluence map comprises updating radiotherapy system instructions, wherein radiotherapy system instructions comprise one or more of jaw, multi-leaf collimator, couch, and/or gantry instructions.

10. The method of claim 1, further comprising calculating a fluence previously delivered to the target region and comparing the previously delivered fluence to the treatment plan fluence map to calculate a fluence difference, and wherein updating the treatment plan fluence map comprises adjusting radiation delivery to deliver the calculated fluence difference.

11. The method of claim 10, further comprising determining dose artifacts in the previously delivered fluence, and wherein updating the treatment plan fluence map comprises adjusting radiation delivery to correct the dose artifacts.

12. The method of claim 1, wherein acquiring PET data, identifying the location of the target region, and updating the treatment plan fluence map occur during a single treatment session.

13. The method of claim 1, wherein the normalization factor and/or dampening factor and/or weighting factor are determined based on an intensity of the PET imaging data originating from the target region.

14. A method for updating a treatment plan fluence map, the method comprising:
   acquiring PET imaging data originating from a target region using PET detectors;
   calculating a fluence previously delivered to the target region;
   comparing the previously delivered fluence to a treatment plan fluence map to determine dose artifacts in the previously delivered fluence; and
   updating the treatment plan fluence map by adjusting radiation delivery to correct the dose artifacts.

15. The method of claim 14, wherein the PET detectors comprise time-of-flight PET detectors.

16. The method of claim 14, further comprising acquiring MV detector data, and wherein updating the treatment plan fluence map uses the acquired MV detector data.

17. The method of claim 14, further comprising delivering radiation to the target region according to the updated treatment plan fluence map using a therapeutic radiation source.

18. The method of claim 17, wherein delivering radiation to the target region comprises adjusting a speed of a couch while the therapeutic radiation source is emitting radiation.

19. The method of claim 17, wherein delivering radiation occurs in at least two separate passes of a couch through radiation emitted by the therapeutic radiation source.

20. The method of claim 19, wherein updating the treatment plan fluence map comprises updating the treatment plan fluence map after a first couch pass and updating the treatment plan fluence map after a second couch pass.

* * * * *